United States Patent [19]
Pang et al.

[11] Patent Number: 6,060,022
[45] Date of Patent: May 9, 2000

[54] AUTOMATED SAMPLE PROCESSING SYSTEM INCLUDING AUTOMATIC CENTRIFUGE DEVICE

[75] Inventors: Wing S. Pang, Hacienda Hts; Mark Gross, Mission Viejo; Hendra Tanumihardja, West Covina; Ruediger F. Rauskolb, Palo Alto, all of Calif.; G. Andrea Pedrazzini, Segrate, Italy; Santiago F. Allen, Yorba Linda, Calif.

[73] Assignee: Beckman Coulter, Inc., Fullerton, Calif.

[21] Appl. No.: 08/887,601

[22] Filed: Jul. 3, 1997

Related U.S. Application Data

[63] Continuation-in-part of application No. 08/675,901, Jul. 5, 1996, abandoned.

[51] Int. Cl.[7] ................................................. G01N 35/02
[52] U.S. Cl. ........................... 422/65; 422/63; 422/67; 422/72; 436/43; 436/45; 436/47; 436/48; 436/50; 494/10
[58] Field of Search ........................ 422/63, 64, 65, 422/67, 100, 103, 104, 72; 436/43, 45, 47, 48, 49, 50, 174, 180; 494/1, 10; 210/143, 144

[56] References Cited

U.S. PATENT DOCUMENTS

| | | | |
|---|---|---|---|
| 4,039,286 | 8/1977 | Keller et al. | 23/23 OR |
| 4,078,895 | 3/1978 | Moran | 23/253 R |

(List continued on next page.)

FOREIGN PATENT DOCUMENTS

| | | |
|---|---|---|
| 0 136 002 A2 | 4/1985 | European Pat. Off. . |
| 0 138 205 A1 | 4/1985 | European Pat. Off. . |
| 0 143 097 A1 | 5/1985 | European Pat. Off. . |
| 0 180511 A1 | 5/1986 | European Pat. Off. . |
| 0 403905 A1 | 12/1990 | European Pat. Off. . |
| 0 438136 A2 | 7/1991 | European Pat. Off. . |
| 0 487 492 A1 | 5/1992 | European Pat. Off. . |
| 0 500506 A1 | 8/1992 | European Pat. Off. . |
| 0 557 828 A1 | 9/1993 | European Pat. Off. . |
| 0 629 858 A1 | 12/1994 | European Pat. Off. . |
| 0 700 719 A1 | 3/1996 | European Pat. Off. . |
| 2129254 | 10/1972 | France . |
| 4110389 | 10/1991 | Germany . |
| 60-188849 | 9/1985 | Japan . |
| 61-189457 | 8/1986 | Japan . |
| 63-85457 | 4/1988 | Japan . |
| 63-286769 | 11/1988 | Japan . |
| 01189562 | 7/1989 | Japan . |

(List continued on next page.)

OTHER PUBLICATIONS

T. Ikeda et al.; "Total Clinical Laboratory Testing System for Laboratory Automation"; Hitachi Review vol. 41, No. 4; pp. 167–172; Sep. 1992.

(List continued on next page.)

*Primary Examiner*—Long V. Le
*Attorney, Agent, or Firm*—William H. May; Margaret A. Kivinski; Sheldon & Mak

[57] ABSTRACT

A system for a clinical lab that is capable of automatically processing, including sorting, of multiple specimen containers. The system comprises a central controller, a workstation, one or more analyzers, and an automated centrifuge. The workstation has automatic detectors for detecting the presence of a holder holding specimen containers. The workstation has a bar code reader for reading bar codes on the containers. The system has a transport subsystem, preferably a workstation robotic arm and an analyzer robotic arm for transporting the specimen containers, moving them to and from the workstation, to and from the analyzers, and to and from the centrifuge. The centrifuge is loaded with buckets containing specimen containers. The workstation can be provided with a balance system for balancing the weight of the buckets used. The workstation can also have a decapper for automatically removing caps from the specimen containers.

20 Claims, 30 Drawing Sheets

U.S. PATENT DOCUMENTS

| | | | |
|---|---|---|---|
| 4,140,488 | 2/1979 | Mack et al. | 422/100 |
| 4,325,910 | 4/1982 | Jordan | 422/64 |
| 4,459,265 | 7/1984 | Berglund | 422/64 |
| 4,533,641 | 8/1985 | Holt | 436/43 |
| 4,595,562 | 6/1986 | Liston et al. | 422/65 |
| 4,609,017 | 9/1986 | Coulter et al. | 141/1 |
| 4,731,225 | 3/1988 | Wakatake | 422/65 |
| 4,735,776 | 4/1988 | Yamamoto et al. | 422/65 |
| 4,738,825 | 4/1988 | Kelln et al. | 422/72 |
| 4,740,025 | 4/1988 | Nelson | 294/99.1 |
| 4,761,268 | 8/1988 | Andersen et al. | 422/72 |
| 4,816,418 | 3/1989 | Mack et al. | 422/69 |
| 4,828,716 | 5/1989 | McEwen et al. | 210/740 |
| 4,835,707 | 5/1989 | Amano et al. | 364/497 |
| 4,857,471 | 8/1989 | Salzman et al. | 436/43 |
| 4,876,926 | 10/1989 | Muszak | 81/3.2 |
| 4,890,484 | 1/1990 | Telfer et al. | 73/61 R |
| 4,965,049 | 10/1990 | Lillig et al. | 422/68.1 |
| 5,008,082 | 4/1991 | Shaw | 422/65 |
| 5,061,639 | 10/1991 | Lung et al. | 436/164 |
| 5,084,242 | 1/1992 | Sakuma et al. | 422/100 |
| 5,104,621 | 4/1992 | Pfost et al. | 422/67 |
| 5,108,703 | 4/1992 | Pfost et al. | 422/65 |
| 5,122,342 | 6/1992 | McCulloch et al. | 422/65 |
| 5,125,748 | 6/1992 | Bjornson et al. | 356/414 |
| 5,139,744 | 8/1992 | Kowalski | 422/67 |
| 5,145,646 | 9/1992 | Tyranski | 422/102 |
| 5,166,889 | 11/1992 | Cloyd | 364/510 |
| 5,178,834 | 1/1993 | Kagayama et al. | 422/65 |
| 5,206,171 | 4/1993 | Dillon et al. | 435/293 |
| 5,209,903 | 5/1993 | Kanamori et al. | 422/65 |
| 5,229,074 | 7/1993 | Heath et al. | 422/64 |
| 5,232,081 | 8/1993 | Kanamori | 198/465.2 |
| 5,246,665 | 9/1993 | Tyranski et al. | 422/64 |
| 5,250,440 | 10/1993 | Kelln et al. | 436/48 |
| 5,260,872 | 11/1993 | Copeland et al. | 364/413.07 |
| 5,270,012 | 12/1993 | Kanamori et al. | 422/102 |
| 5,271,899 | 12/1993 | Carbonari | 422/67 |
| 5,282,149 | 1/1994 | Grandone et al. | 364/497 |
| 5,289,385 | 2/1994 | Grandone | 364/497 |
| 5,314,825 | 5/1994 | Weyrauch et al. | 436/43 |
| 5,324,481 | 6/1994 | Dunn et al. | 422/64 |
| 5,332,549 | 7/1994 | MacIndoe, Jr. | 422/63 |
| 5,348,705 | 9/1994 | Koreyasu et al. | 422/67 |
| 5,350,564 | 9/1994 | Mazza et al. | 422/63 |
| 5,352,612 | 10/1994 | Huber et al. | 436/47 |
| 5,355,304 | 10/1994 | DeMoranville et al. | 364/413.02 |
| 5,355,439 | 10/1994 | Bernstein et al. | 395/82 |
| 5,358,691 | 10/1994 | Clark et al. | 422/64 |
| 5,362,648 | 11/1994 | Koreyasu et al. | 436/48 |
| 5,363,885 | 11/1994 | McConnell et al. | 141/1 |
| 5,366,062 | 11/1994 | Markin et al. | 198/345.3 |
| 5,366,896 | 11/1994 | Margrey et al. | 436/48 |
| 5,369,566 | 11/1994 | Pfost et al. | 364/147 |
| 5,370,215 | 12/1994 | Markin et al. | 198/346.1 |
| 5,377,813 | 1/1995 | Markin et al. | 198/465.1 |
| 5,380,487 | 1/1995 | Choperena et al. | 422/63 |
| 5,380,488 | 1/1995 | Wakatake | 422/65 |
| 5,402,875 | 4/1995 | Markin et al. | 198/346.1 |
| 5,417,124 | 5/1995 | Marteau D'Autry | 73/864.25 |
| 5,417,922 | 5/1995 | Markin et al. | 422/65 |
| 5,419,871 | 5/1995 | Muszak et al. | 422/63 |
| 5,424,212 | 6/1995 | Pinsl-Ober et al. | 436/50 |
| 5,427,743 | 6/1995 | Markin | 422/104 |
| 5,428,470 | 6/1995 | Labriola, II | 359/119 |
| 5,437,838 | 8/1995 | DeMoranville et al. | 422/67 |
| 5,439,647 | 8/1995 | Tanimizu et al. | 422/64 |
| 5,443,791 | 8/1995 | Cathcart et al. | 422/65 |
| 5,455,008 | 10/1995 | Earley et al. | 422/100 |
| 5,479,969 | 1/1996 | Hardie et al. | 141/130 |
| 5,482,861 | 1/1996 | Clark et al. | 436/48 |
| 5,578,269 | 11/1996 | Yaremko et al. | 422/64 |
| 5,814,276 | 9/1998 | Riggs | 422/65 |
| 5,855,847 | 1/1999 | Oonuma et al. | 422/64 |

FOREIGN PATENT DOCUMENTS

| | | |
|---|---|---|
| 06094729 | 4/1994 | Japan. |
| 06347466 | 12/1994 | Japan. |
| 07120473 | 5/1995 | Japan. |
| 2089034 | 6/1989 | United Kingdom. |
| WO 91/16675 | 10/1991 | WIPO. |
| WO 93/154071 | 8/1993 | WIPO. |
| WO 94/15219 | 7/1994 | WIPO. |

OTHER PUBLICATIONS

J. Lindsey; "A Retrospective on the Automation of Laboratory Synthetic Chemistry"; Chemometrics and Intelligent Laboratory Systems vol. 17, No. 1; pp. 15–45; Oct. 1992.

J. Little; "Advances in Laboratory Robotics for Automated Sample Preparation"; Chemometrics and Intelligent Laboratory Systems vol. 21, Nos. 2/3; pp. 199–205; Dec. 1993.

J. Gentsch; "Flexible Laboratory Automation to Meet the Challenge of the 90's"; Chemometrics and Intelligent Laboratory Systems vol. 21, Nos. 2/3; pp. 229–233; Dec. 1993.

International Search Report; PCT/US 97/11718; Mar. 27, 1998; 9 pp.

Technical Brief, *Automated ELISA Assays*, Zymark Corporation, Hopkinton, MA (1985), 5 pages.

Hamilton, *Fermentation Products*, Advances in Laboratory Automation Robotics, Zymark Corporation, Hopkinton, MA (1986), pp. 3–21.

Hahn, *Automated EIA Microplate Management System Applications of a Monoclona Antibody Development Laboratory*, Zymark Corporation, Hopkinton, MA (1986), pp. 169–179.

Beckman BIOMEK 1000 (1986), 8 pages.

PK268, Product Sheet (1994), Oriental Motor U.S.A. Corp., Los Angeles, CA.

*The Intelligent Actuator*, Robotic Positioning Systems, Automation Controls Group Inc., Torrance, CA, 4 pages.

Booklet entitled Series SGM/SGD, Campbell & George Co., San Carlos, CA, 19 pages.

Price List & Ordering Information, Intelligent Motion Systems, Inc. (IMS), Taftville, CT (Sep. 1, 1994), pages.

Product Sheet, A255—Industrial robot Asystem, CRS Robotics, 1 page.

DSP–Series Motion Controller Installation, Version 2.1c, Jun. 1994, Motion Engineering, Inc. (MEI), Santa Barbara, CA, 7 pages.

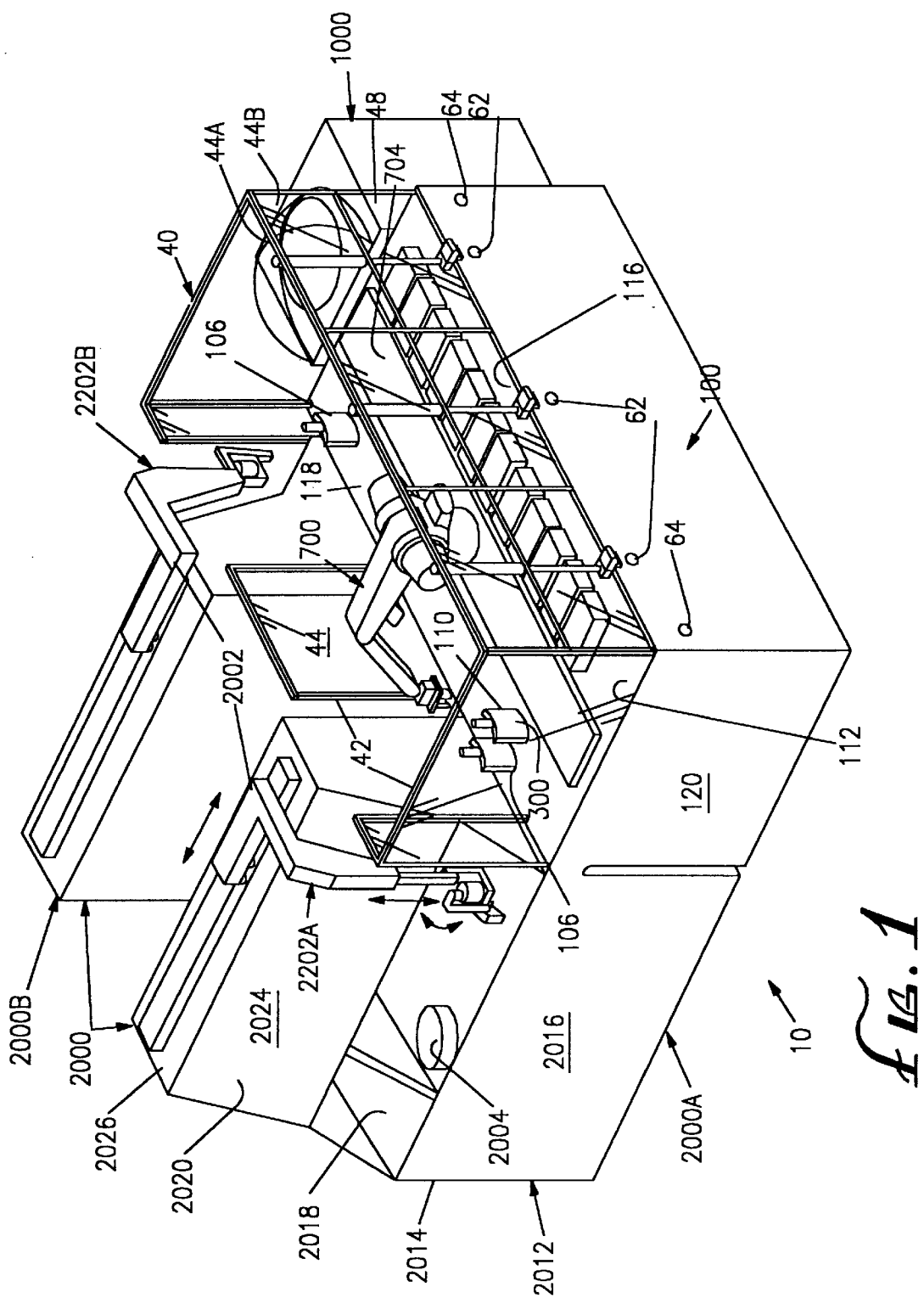

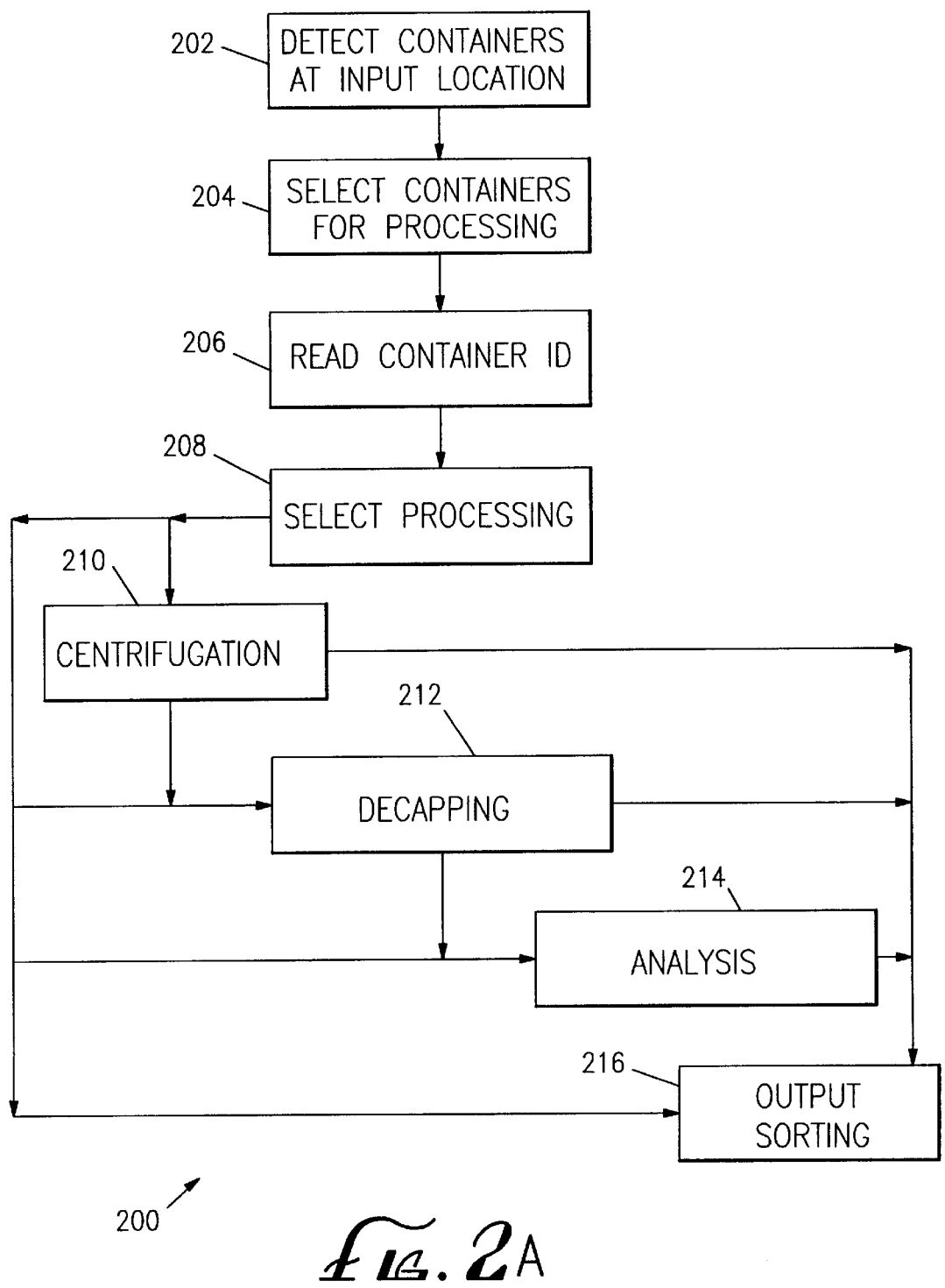

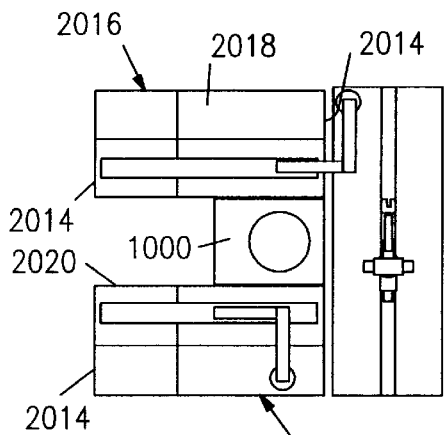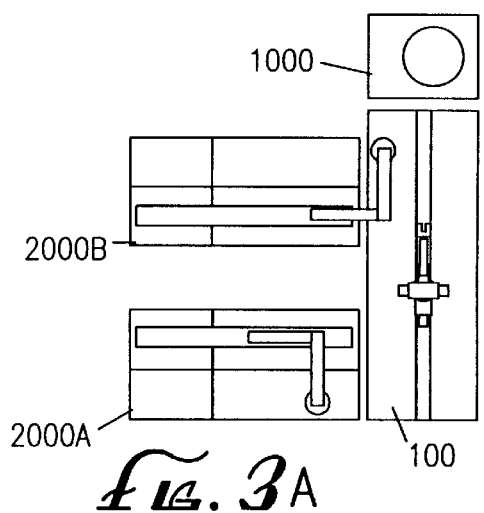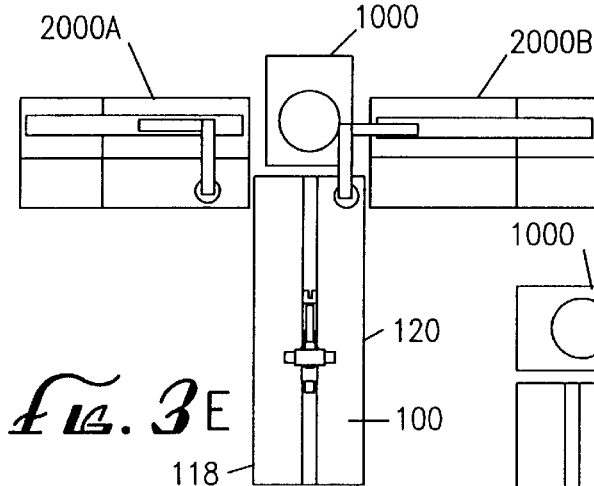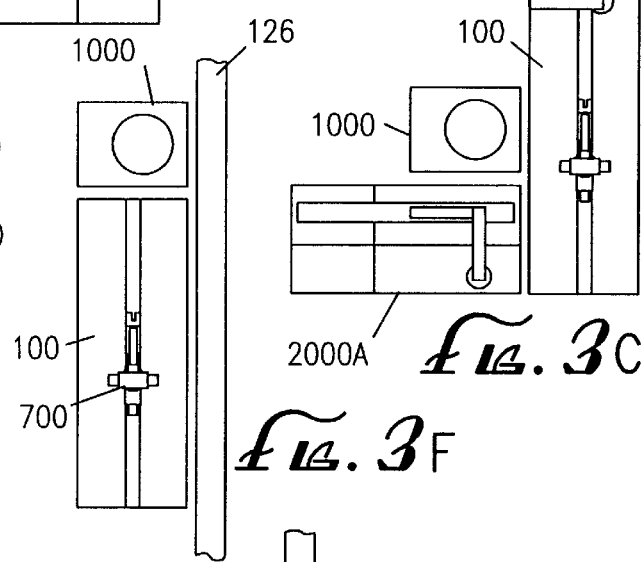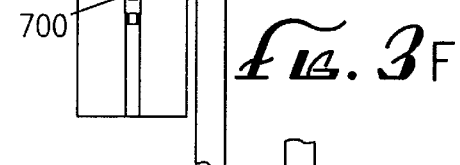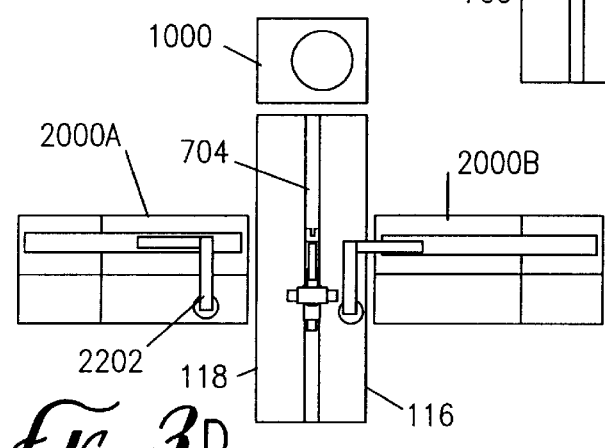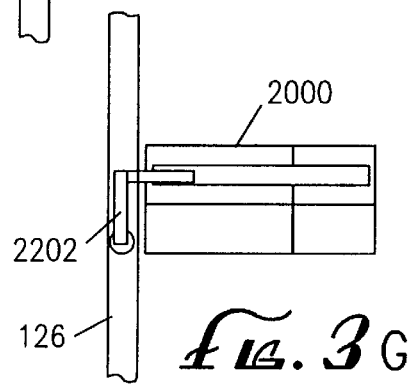

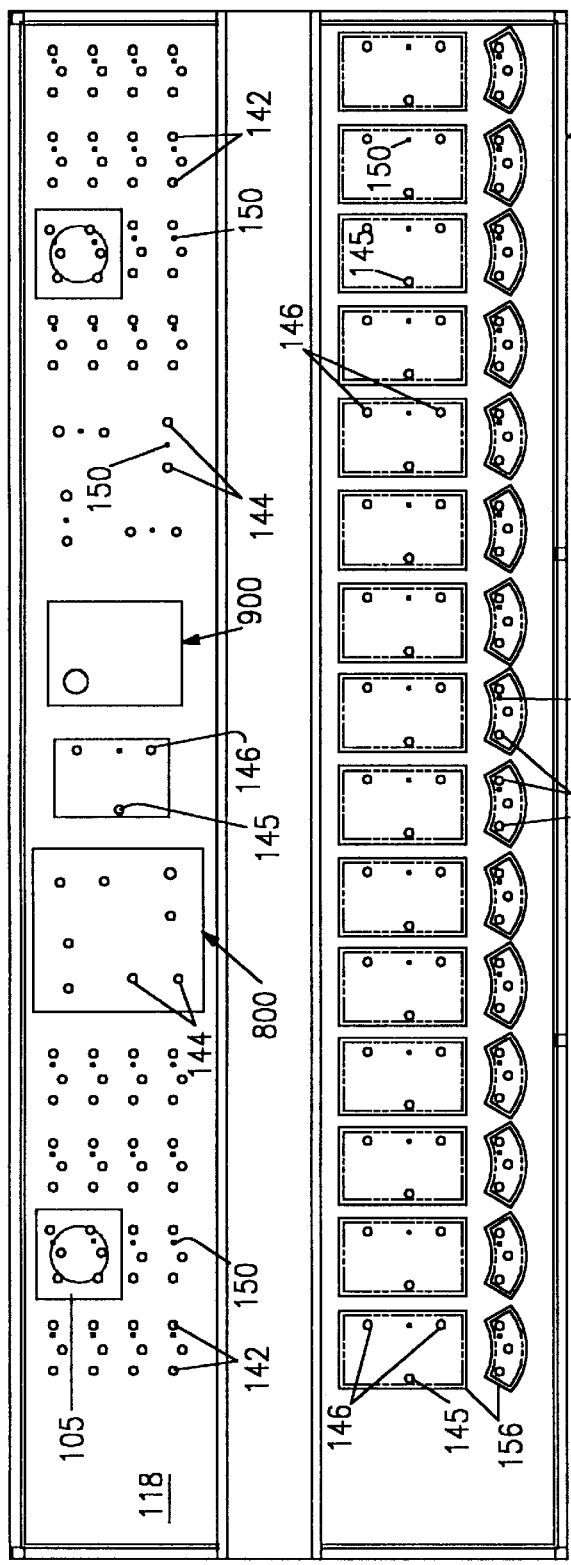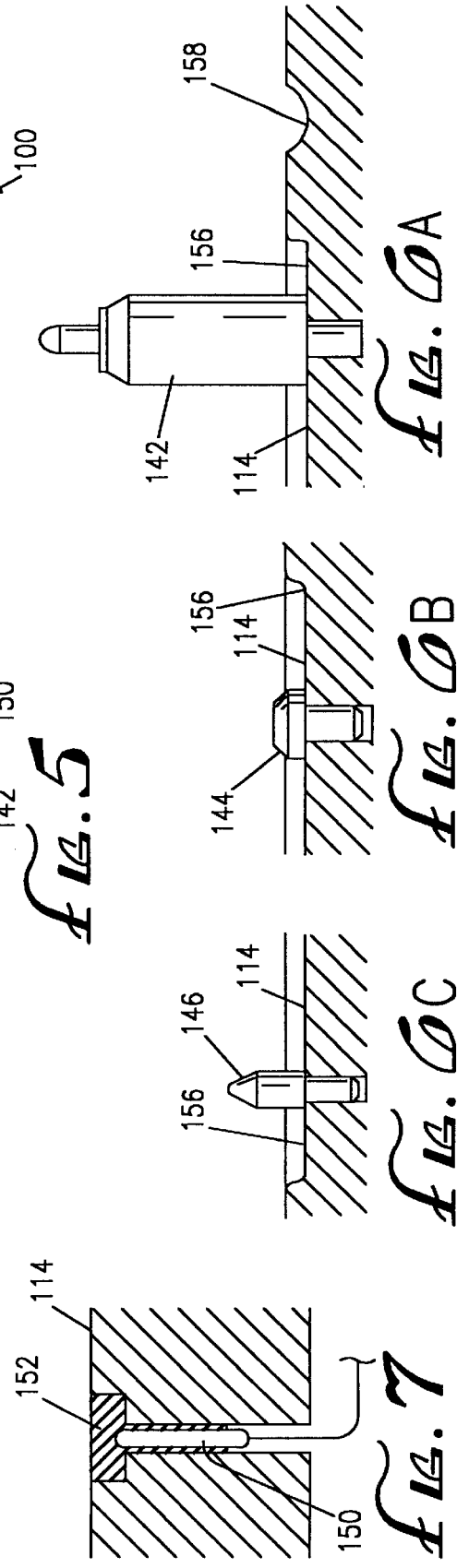

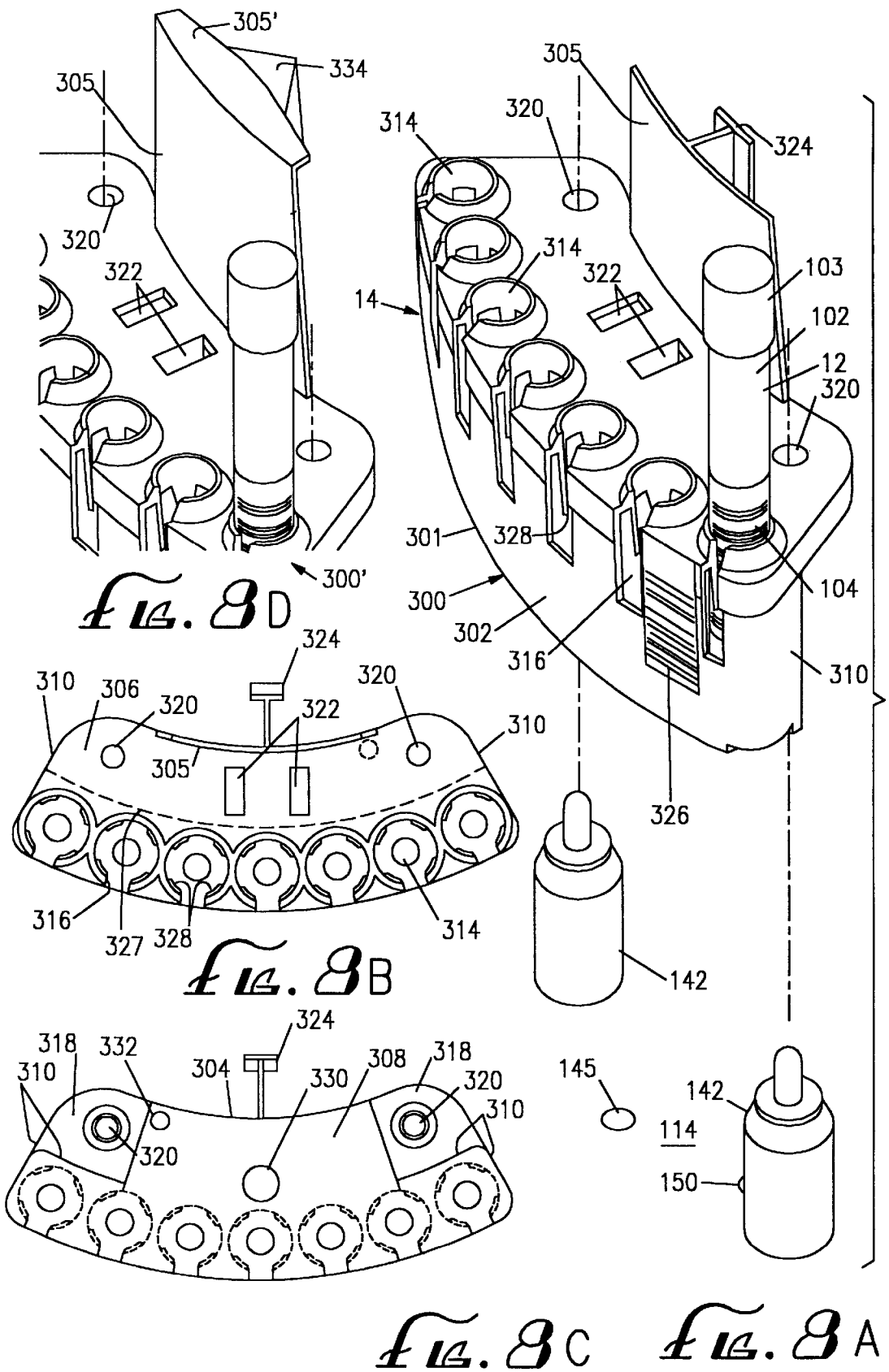

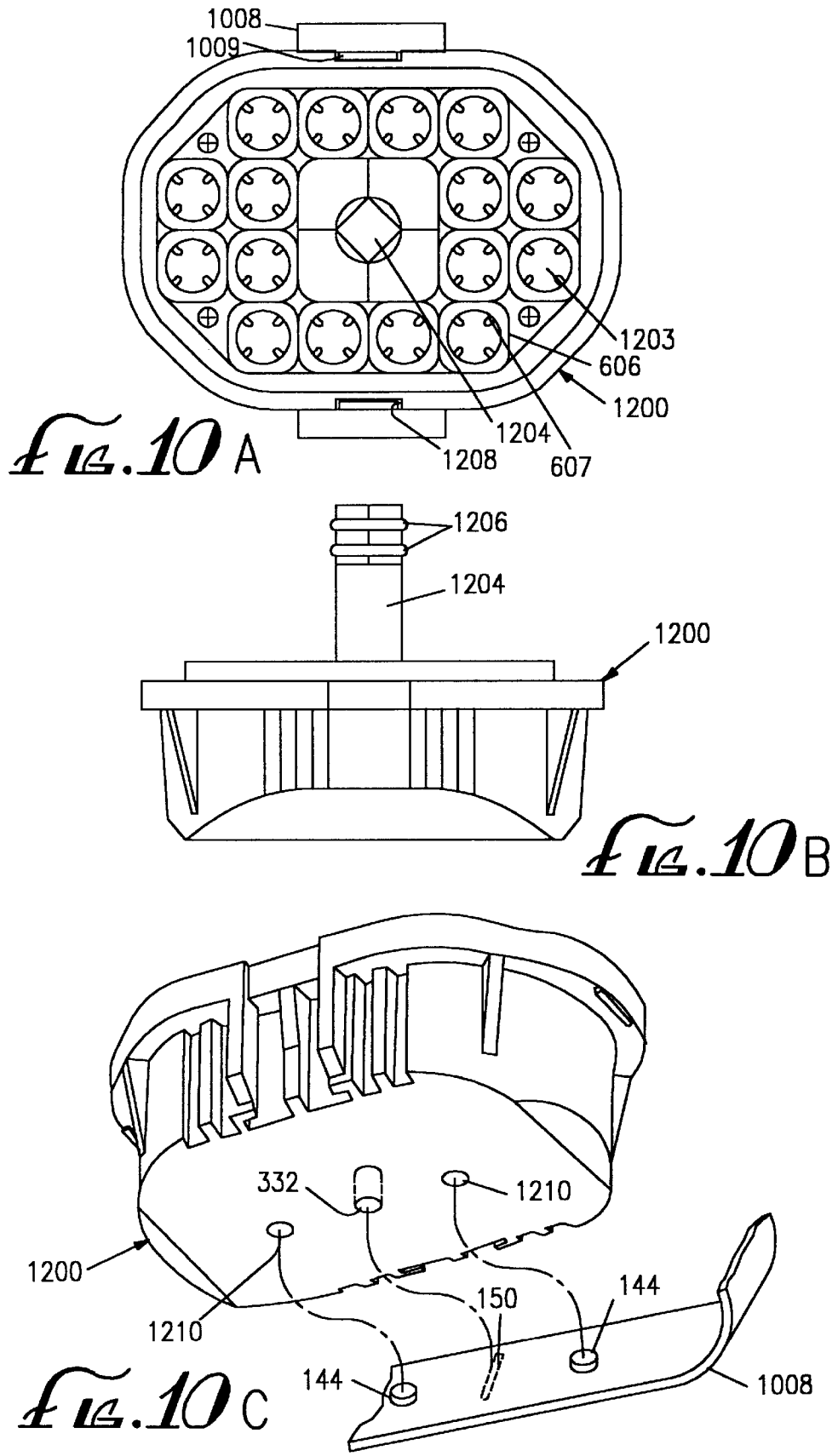

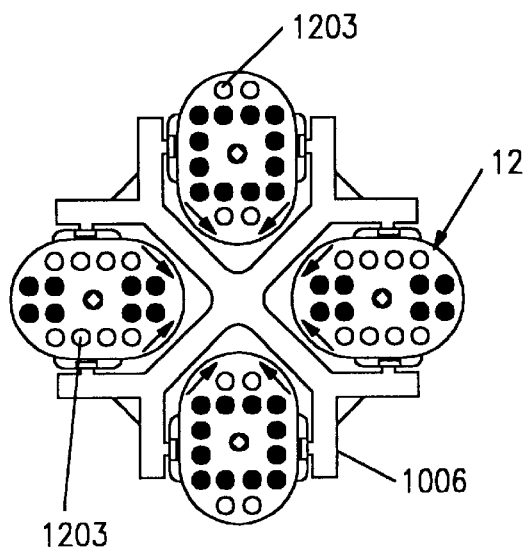
*Fig. 11*A
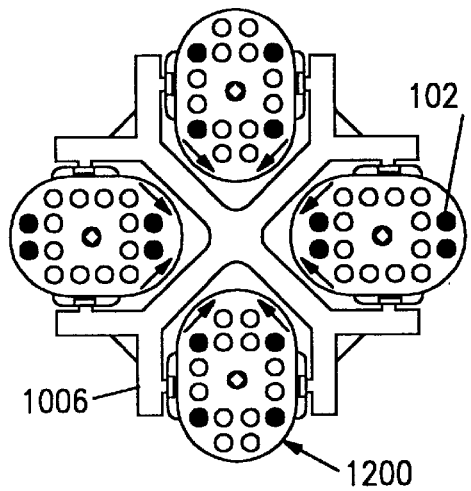
*Fig. 11*B
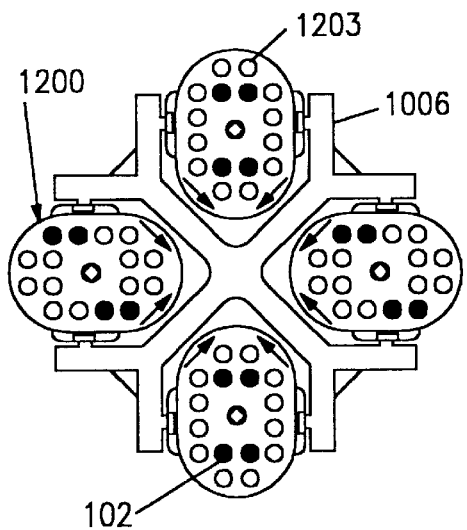
*Fig. 11*C
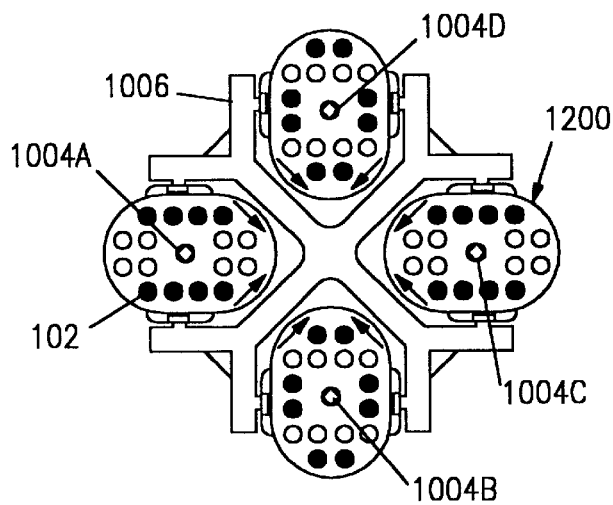
*Fig. 11*D

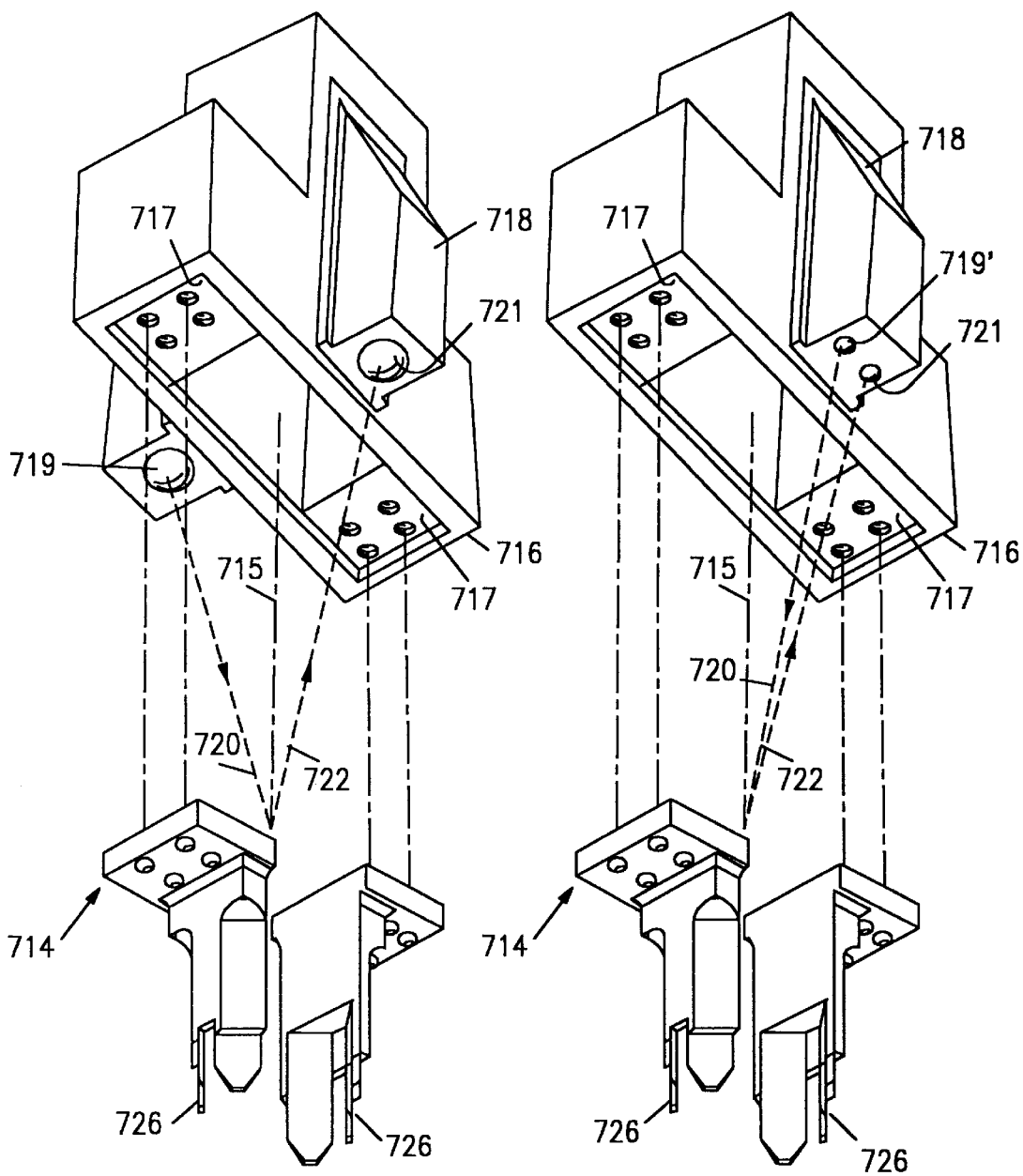
_Fig. 13_C    _Fig. 13_D

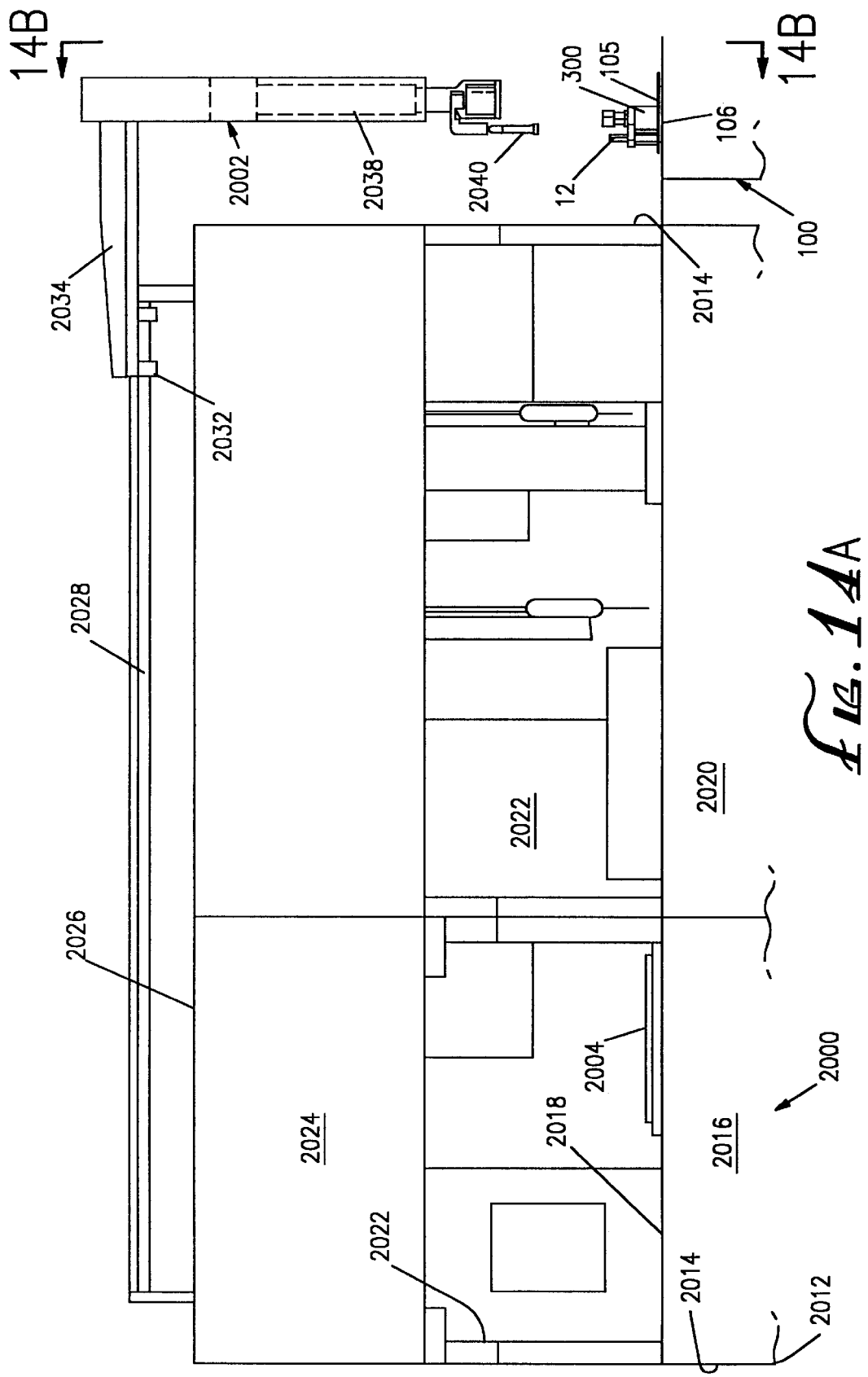

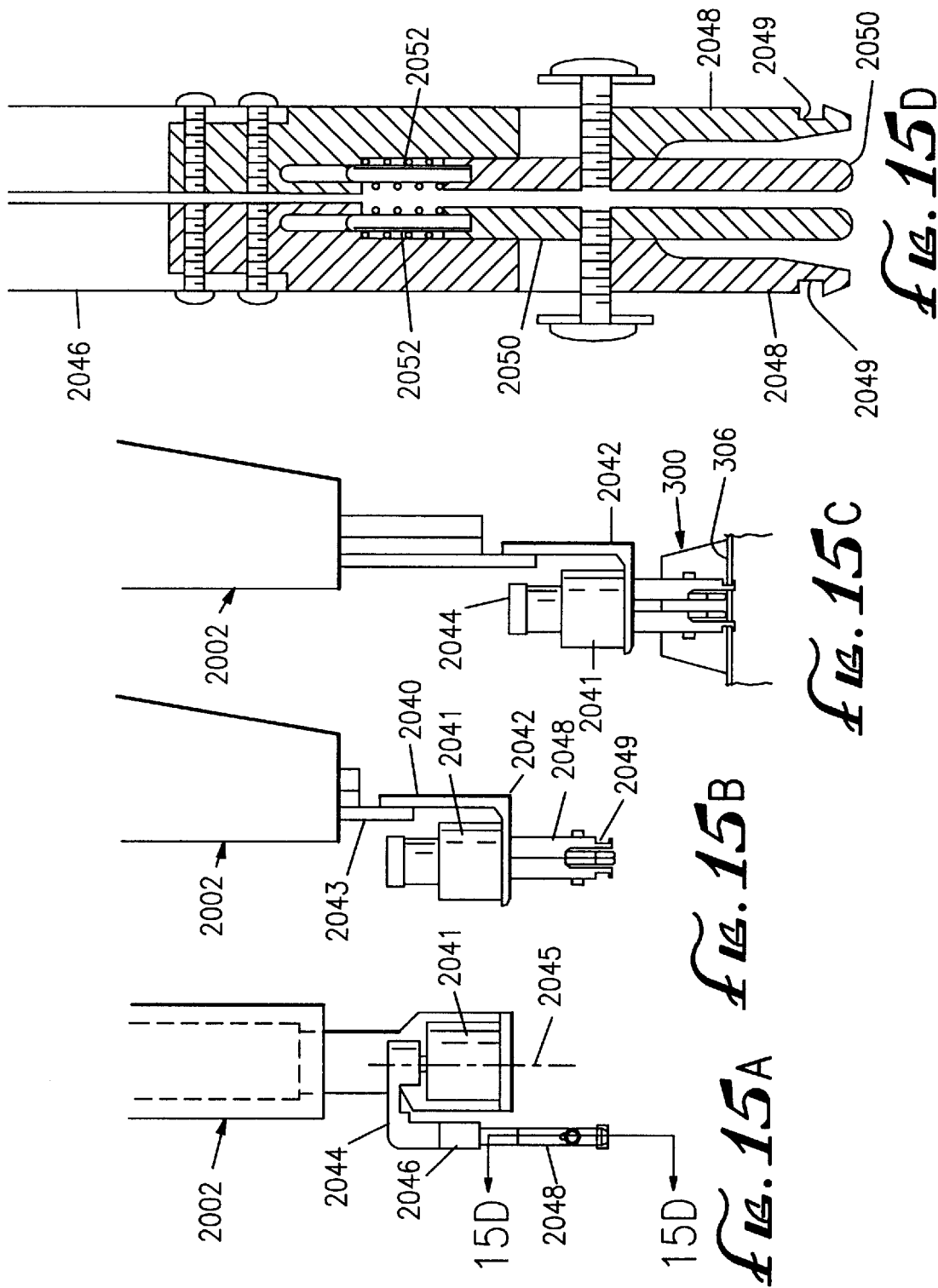

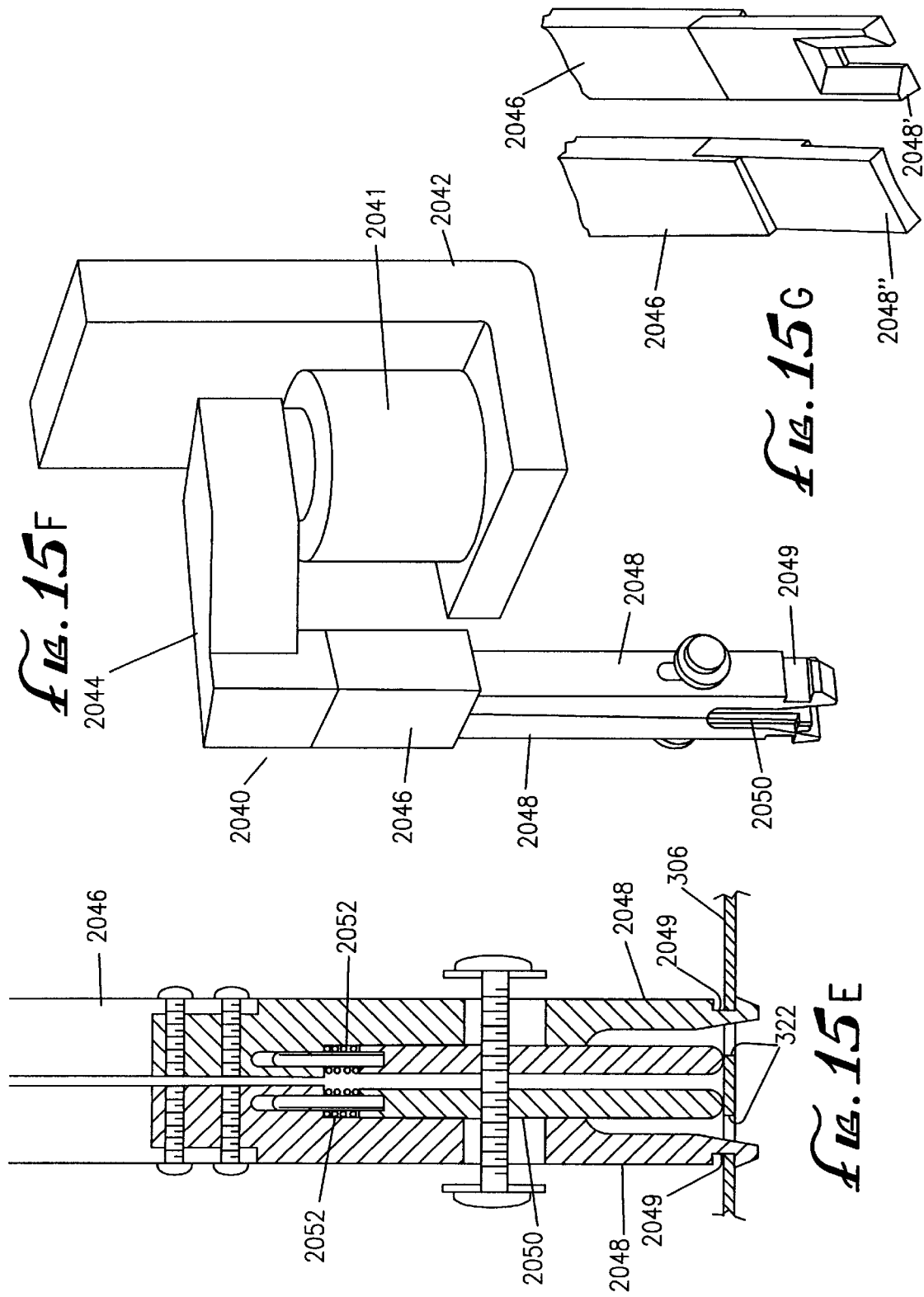

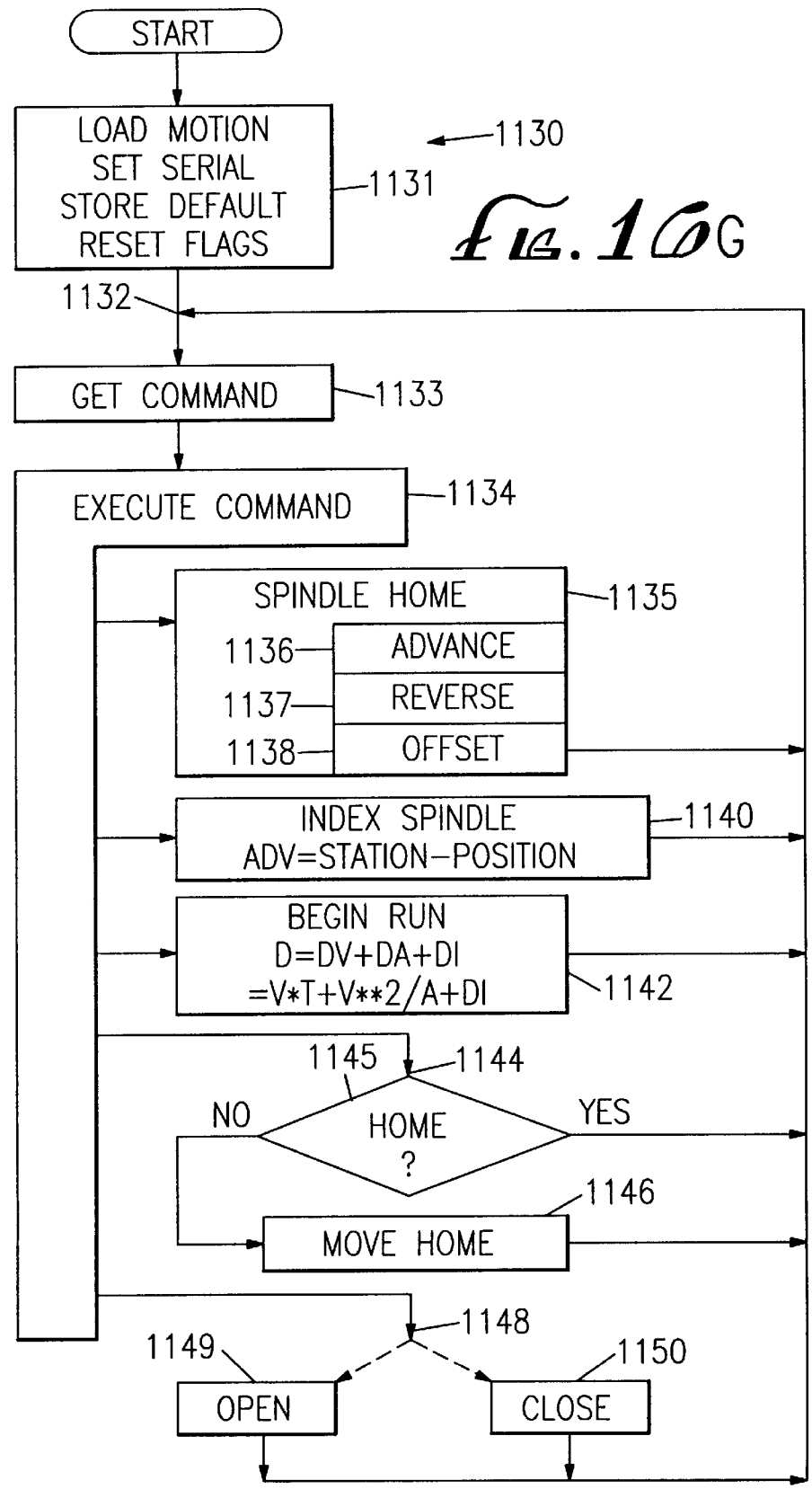

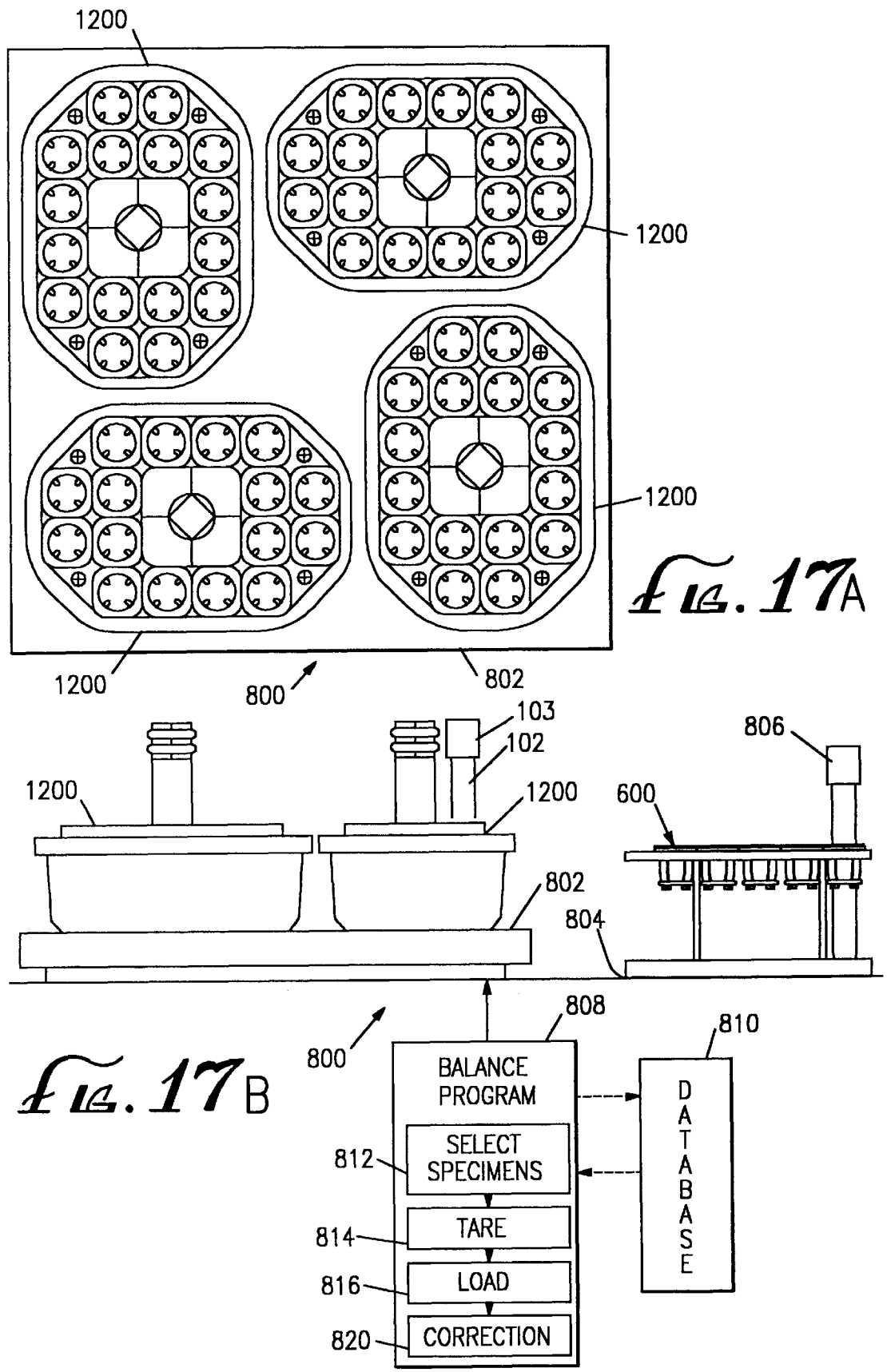

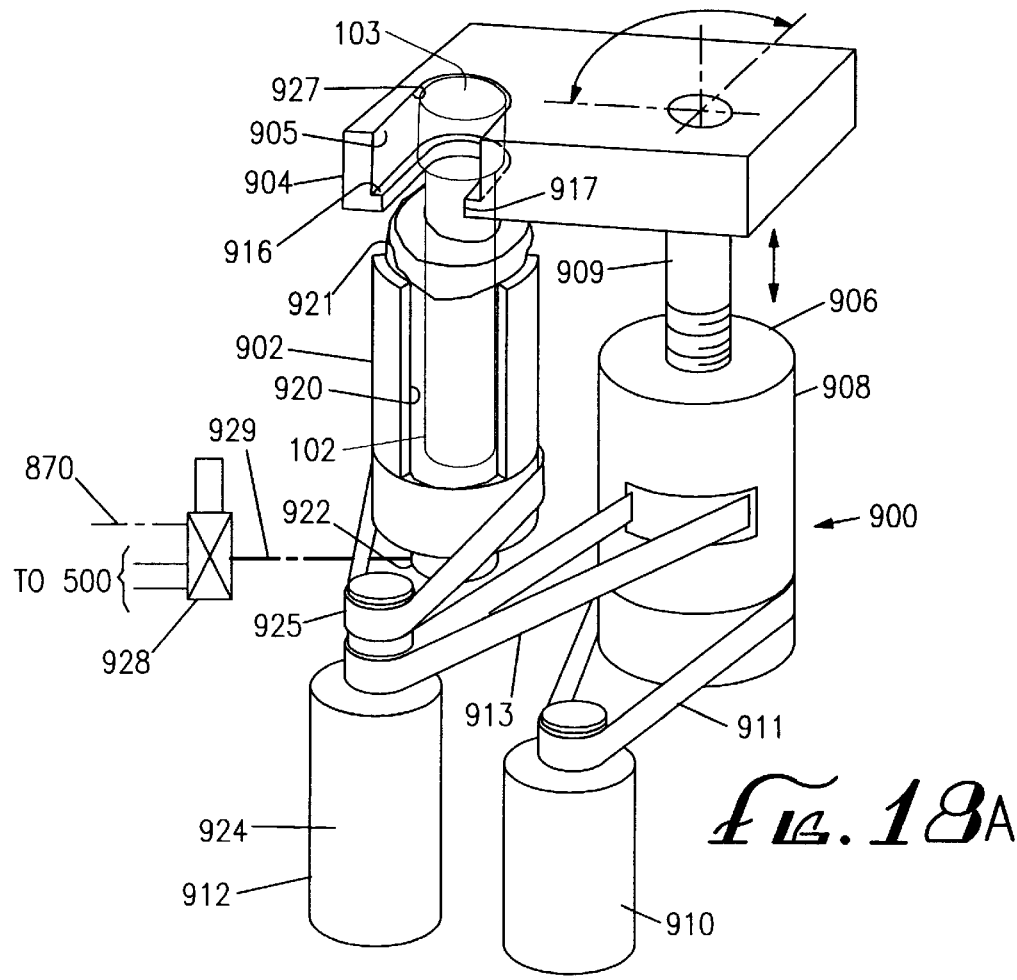
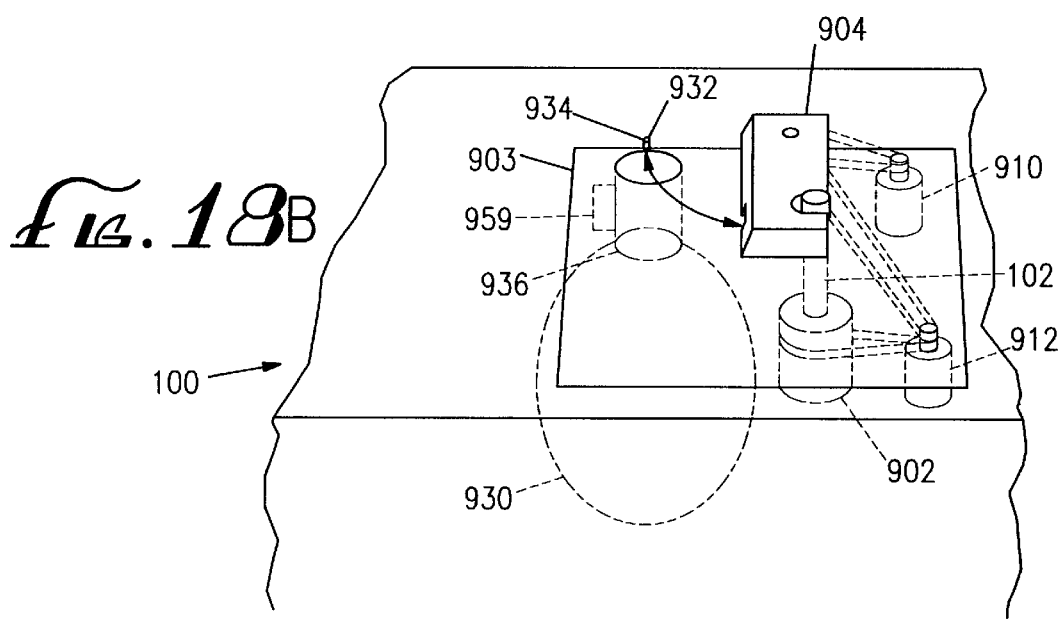

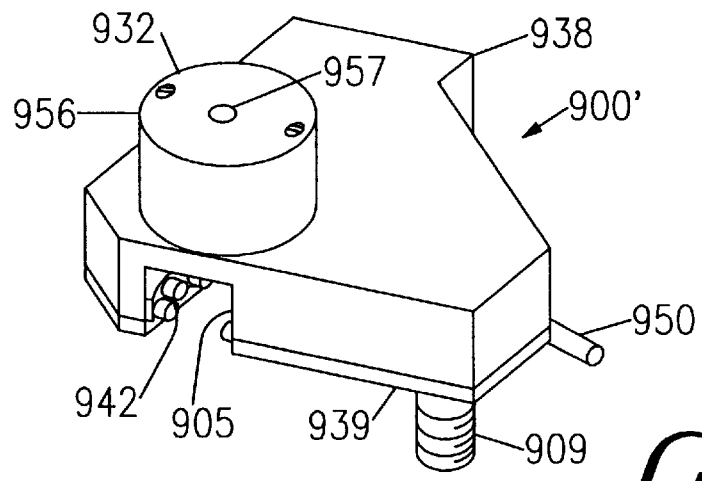
*fig.18*C
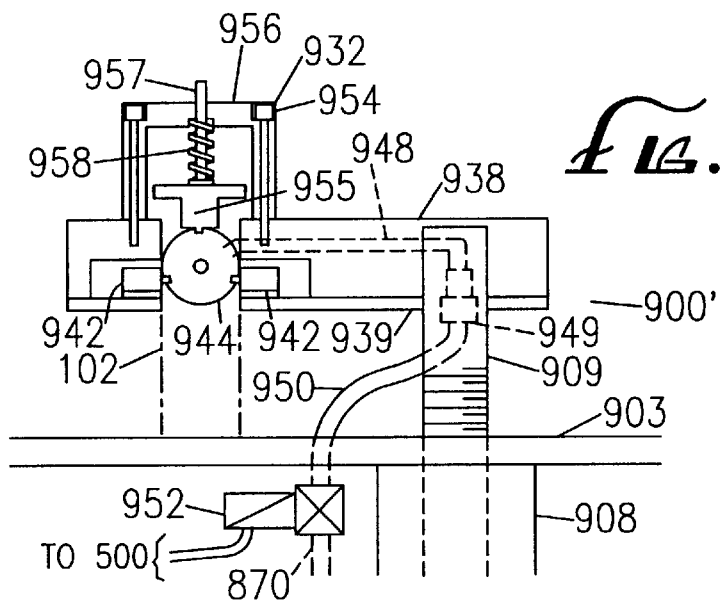
*fig.18*D
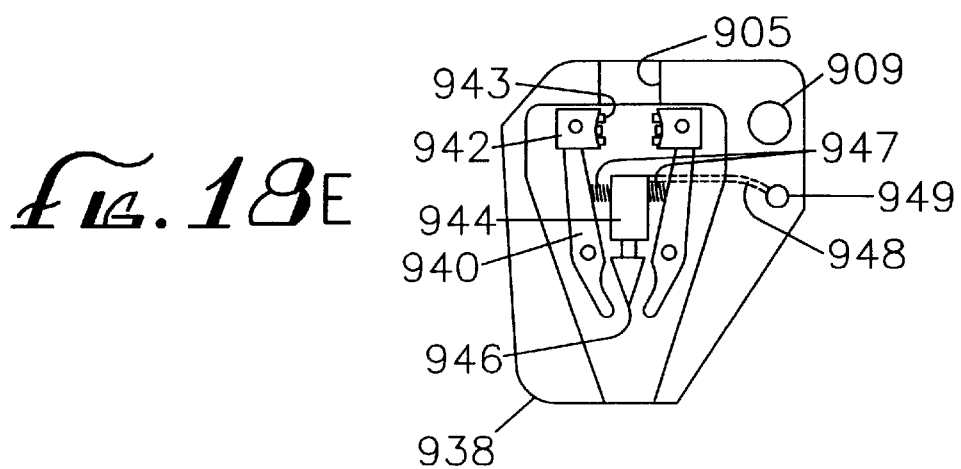
*fig.18*E

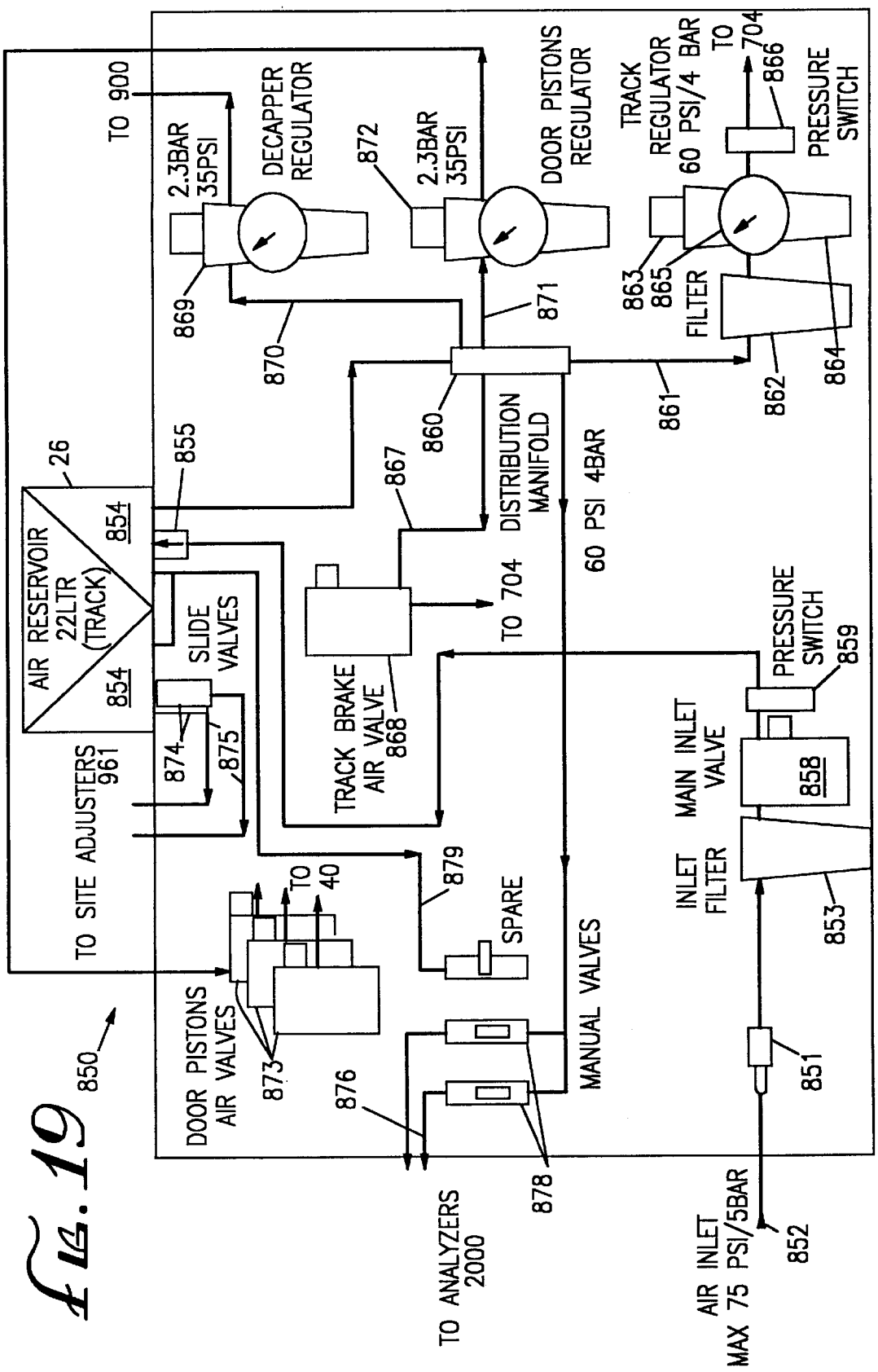

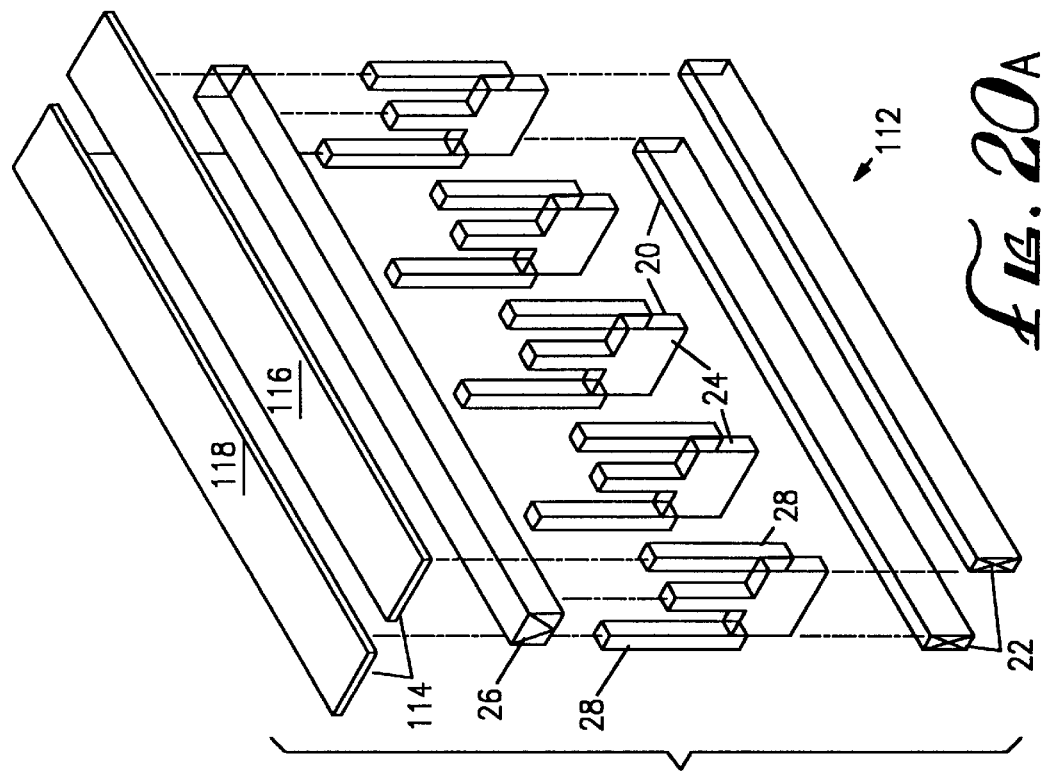
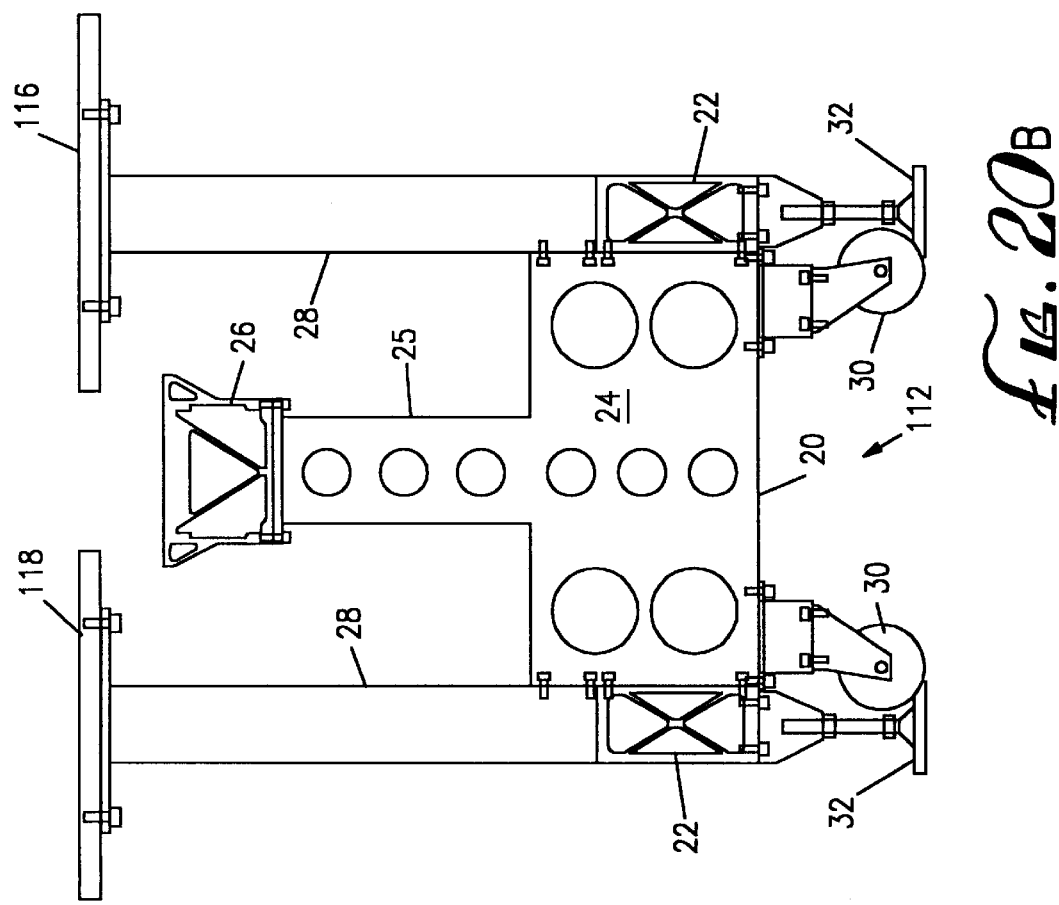

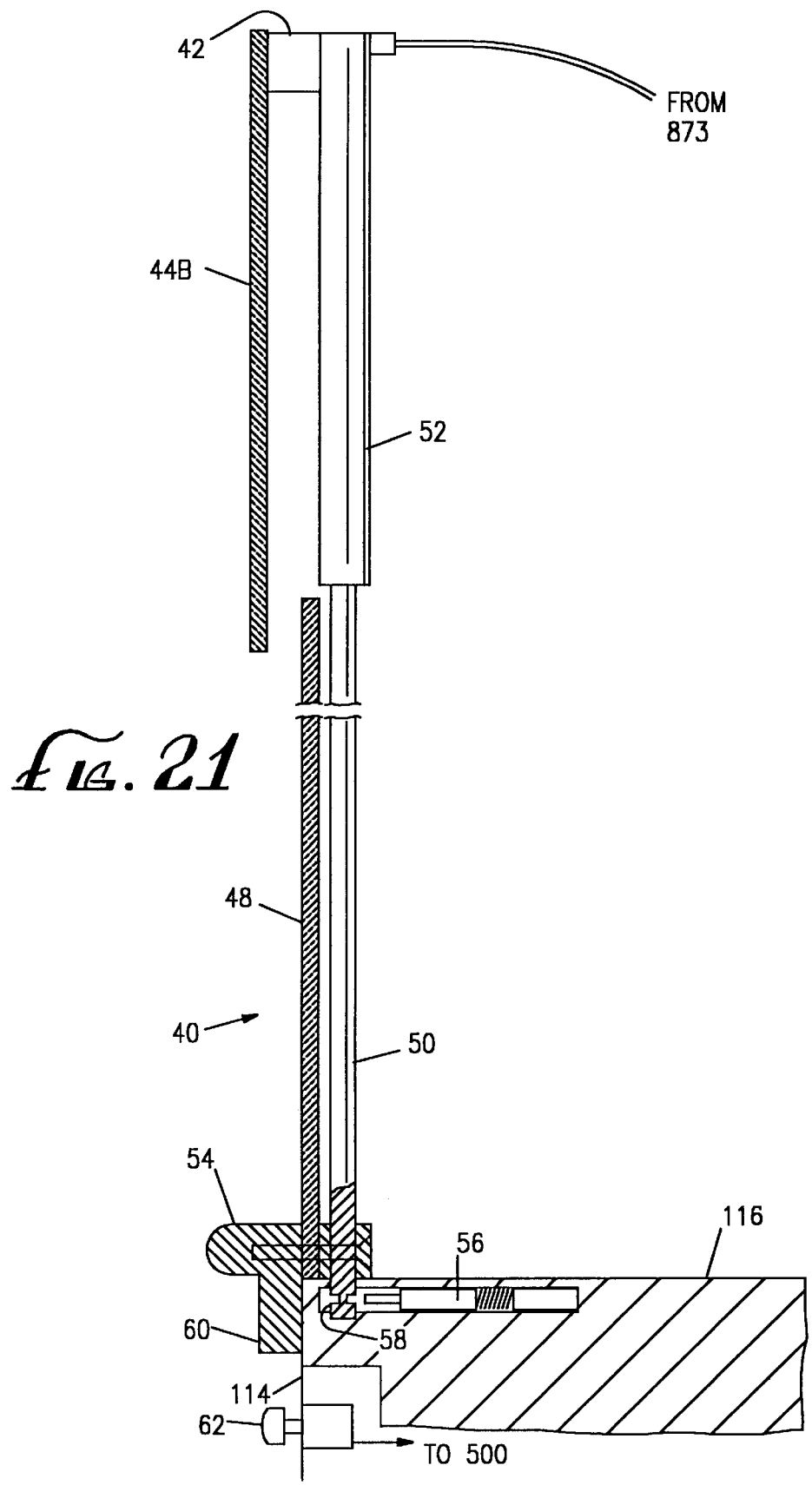

AUTOMATED SAMPLE PROCESSING SYSTEM INCLUDING AUTOMATIC CENTRIFUGE DEVICE

RELATED APPLICATION

This application is a continuation-in-part of application Ser. No. 08/675,901 that was filed on Jul. 5, 1996, now abandoned, being incorporated herein by this reference.

BACKGROUND

The present invention relates generally to systems for the automation of laboratory tests, and particularly testing of biological specimens.

Laboratory testing has changed and improved remarkably over the past 70 years. Initially, tests or assays were performed manually, and generally utilized large quantities of serum, blood, or other biological fluids. However, as mechanical technology developed in the industrial workplace, similar technology was introduced into the clinical laboratory. With the introduction of new technology, methodologies were also improved resulting in improved quality of the results produced by the individual instruments, and a decrease in the amount of specimen required to perform each test.

Instruments have been developed to increase the efficiency of testing procedures by reducing turnaround time and decreasing the volumes necessary to perform various assays. Exemplary of such instruments are the Synchron™ line of automated analyzers available from Beckman Instruments of Fullerton, Calif. Such instruments are capable of automatically analyzing a large number of blood specimens and a large number of analytes, providing reliable, accurate, and fast analysis of specimens.

There remains room for improvement in the operations of clinical laboratories, in spite of the advances that have been made. For example, significant labor is still required for sample preparation. Sample preparation can include the sorting of specimens for processing, centrifugation, and removal of the caps of containers containing the specimens. Centrifugation requires loading multiple specimen containers, which are typically test tubes, into centrifuge buckets, balancing the weight of the buckets so the centrifuge is balanced, loading the buckets into the centrifuge, closing the centrifuge lid, centrifuging, opening the lid, removing the buckets, and then removing the test tubes from the buckets. All these operations are labor intensive, increasing the cost of laboratory analysis. Moreover, these labor intensive steps can lead to operator error. Also, human involvement always involves the risk of contamination of specimens by the operator, and exposure of the operator to dangerous biological substances.

There have been attempts to improve automation include the use of conveyor systems for conveying specimens to analyzers, such as those described in U.S. Pat. Nos. 5,178, 834 and 5,209,903. A difficulty with using conveyor systems is that they generally are part of a total integrated system, which system includes special analyzers and other handling equipment. Thus a clinical laboratory that wishes to switch to a conveyor system may need to replace its entire existing system, with attendant high capital investment and significant training expense for the operators.

Another common problem in clinical laboratory systems is how to deal with "STAT" specimens. These are specimens that need immediate attention. For example, specimens from patients in the emergency room often require "STAT" analysis so attending physicians can determine the cause of the medical emergency. Present clinical systems currently depend on operator intervention to interrupt the normal flow of work to be certain that the STAT samples get immediate attention. However, in the hustle and bustle of a clinical laboratory these STAT samples and specimens do not always get the immediate attention they need.

Laboratory centrifuges of the prior art typically have a high-speed motor-driven spindle, a plurality of holders for test-tubes, test-tube racks and/or vials being provided at respective angularly spaced stations of a head assembly of the spindle, the head assembly being located within a tub-shaped cavity and surrounded by a safety ring, the centrifuge also having a safety-latched door for covering the cavity during operation of the spindle. The spindle is driven at a selected speed which can be as high as from about 3600 RPM up to about 100,000 RPM.

A number of challenges are associated with automation of centrifugation. For example:

1. It is desired to bypass centrifuging in some cases;
2. Access to the centrifuge is impeded by the presence of a protective cover, which typically swings vertically between open and closed positions;
3. Inordinate expense is associated with automating the cover and protecting against persons being injured during movement thereof;
4. It is necessary to have the centrifuge balanced within approximately 10 grams before high-speed operation can commence; and
5. Many processes are inordinately burdened by the time required for spinning the samples, particularly when lengthy periods are needed for loading and unloading the centrifuge, for programming spin cycles, and for accelerating and decelerating the centrifuge.

In some centrifuges of the prior art, a spindle head can be indexed to one of a plurality of rest positions for facilitating loading and unloading at corresponding angularly spaced receptacle stations of the spindle head assembly. However, these centrifuges are undesirably complex and expensive to provide in that separate motors and controls are used for the indexing and for high-speed operation; a further consequence being degraded high-speed performance resulting from added inertia that is associated with the indexing motor.

Accordingly, there is a need for a system that can automate the sample handling and sample preparation process, including the centrifugation for analytical procedures, including in particular, clinical laboratories. It is desirable that the system can be used with existing equipment, i.e., existing equipment does not need to be replaced, and can be used with a wide variety of existing analytical equipment. Further, system throughput should be only minimally affected by specimens requiring centrifugation. Moreover, it is desirable that the system recognize and expeditiously handle STAT samples, minimize the health risks associated with contacting biological samples, and minimize the chance that specimens will be inadvertently contaminated by operator error.

SUMMARY

The present invention provides a system that meets these needs. The present system is based upon a modular workstation that can automatically prepare biological specimens for further processing by a large variety of analytical equipment, without having to replace existing analytical equipment. The system can sort incoming samples, and prioritize STAT samples. As needed, incoming samples can be automatically centrifuged, decapped, and transported to selected analytical equipment. The system can be automatically controlled through the use of a central controller. The system provides efficient, high throughput and fast turn-around analytical results, with decreased chance for operator error and decreased exposure of operators to biological substances.

Typically, specimens to be automatically processed are in multiple containers, such as test tubes, which can be capped. Each of the containers is provided with container identification indicia, such as a bar code. The containers are in one or more holders such as sectors and/or racks that can have identification indicia thereon.

In accordance with one aspect of the present invention, a processing system includes (i) the central controller, (ii) a workstation having subsystems for sorting, preparing, and transporting the containers, (iii) a centrifugation system for centrifugation of selected specimens, and (iv) at least one analyzer for selectively analyzing specimens. Not only is this overall system believed to be novel and inventive, it is also believed that the subsystems of the overall system, as well as particular mechanical components of the system, are novel and inventive.

Central Controller

The central controller, which can be provided as part of the workstation, comprises memory storage and a data input element for inputting processing instructions into the memory storage for the processing of each container according to the container identification indicia. Based on instructions in the central controller, each container can preferably be processed as follows:

(a) Sorting only, i.e., the workstation is used only for sorting containers for further processing;
(b) Sorting and centrifugation;
(c) Sorting, centrifugation, and decapping;
(d) Sorting, centrifugation, decapping and analysis;
(e) Sorting, decapping and analysis (for samples not requiring centrifugation); and
(f) Sorting and analysis (for samples not requiring centrifugation and automated decapping).

The central controller can be provided with a process supervisor having a programmed detect input step for determining introduction of containers at an input location on the workstation, a container select step in which detected containers are selected for processing, an identification step for defining process components for each selected container according to the container identification indicia, and a process select step for initiating the defined process components being one or more of sorting, centrifugation, decapping, and analysis.

Workstation

The workstation is provided with detectors for detecting the presence of a holder in the system. The detectors have an output element for signaling the presence of a holder to the central controller. The workstation has an indicia reader, such as a bar code reader, for reading the container identification indicia. The indicia reader is provided with an output element for providing container identification indicia to the central controller. Preferably the indicia reader is also effective for signaling holder identification indicia to the central controller.

The workstation also includes a container sorting subsystem which has a data input element in communication with the central controller for receiving instructions from the central controller for sorting containers for selective processing according to the processing instructions stored in the central controller memory storage. The container sorting system also includes a plurality of sort sites for placement of containers according to their processing instructions.

Typically the workstation includes multiple input locations for initial placement of the containers by an operator, each of the input locations having one of the detectors. Preferably at least one of the locations is selected for priority containers, i.e., STAT specimens, so that the central processor, when signaled by the detector output element about the presence of a priority container, provides instructions for priority processing of priority containers.

The workstation typically comprises a table with positioners, such as posts, for positioning the holders and centrifuge receptacles in predetermined locations. The table can be provided with below surface detectors, such as reed switches, for detecting the presence of a holder on the table. A workstation robotic arm is supported on the table, and is generally provided with the indicia reader, which can be a bar code reader. The table has an analyzer delivery site for placement of holders for analysis by the analyzer, and an analyzer receiving site for receiving analyzed samples from the analyzer. Preferably the workstation is provided with a shield system for selectively blocking operator access such as would interfere with system operation. The shield system can include a partition that encloses the top of the workstation and having openings for passage of the analyzer robotic arms, an enlargement for passage of receptacles to the centrifuge, and an interlocked access door. The access door can be a sash door having an actuator being responsive to the central controller, and an operator input device for signaling access requests to the central controller, the controller being operative for appropriately inhibiting operation of the workstation robotic arm and then activating the actuator for opening the door. Preferably a base of the table has a modular plurality of bulkheads that are connected by a pair of beams and a rail of the robotic arm track. Preferably the rail provides a high capacity air reservoir for the system.

Two different types of holders can be used, and different types of positioners for the different types of holders can be used. For example, a first holder, such as a sector, can be used for containers to undergo processing, wherein the first holders are transported by the transport system. Second holders, such as racks, can be used where the containers of the second holder are transported by the transport system individually for sorting. It is preferred that the holder positioners for the second holders are closer to the transport system than are the holder positioners for the first holders for minimal movement of the transport system.

Typically the table is located proximate to one of the analyzers. Preferably the section of the table closest to the analyzer is used for holding containers for delivery to the analyzer. The table can have an input side for receiving containers for processing, the input side being opposed from the analyzer side, with a transport path for the workstation robotic arm located between the input side and the analyzer side.

Centrifugation System

The centrifugation system includes an automated centrifuge which is loaded with multiple receptacles, also known as baskets or buckets, each bucket receiving multiple containers. The centrifuge includes a motor coupled to a spindle that receives the buckets, a controller, and optionally, a lid, and a lid drive. The centrifuge controller indexes or stops the spindle at selected positions for automated placement and removal of the buckets in response to signals from the central controller. The lid has a closed position and an open position, and the lid drive opens and closes in response to instructions from the centrifuge controller.

Before the loaded receptacles are placed in the centrifuge, preferably they are balanced in a balance system. The balance system, which can be an included part of the workstation, comprises a scale having sites for receiving and holding a plurality of container receptacles, and a balance controller for selectively depositing containers in cavities of the receptacles while correlating incremental weight changes with the locations of each deposit for equalizing weight in pairs of the receptacles. The balance controller can be implemented as a balance program within the central controller, the balance program maintaining a database of container locations and associated weights, and directing the robotic arm for depositing the containers. Preferably the balance system also includes a supply of dummy loads, i.e., dummy test tubes, the balance controller being operative for selectively depositing selected dummy loads in receptacles for limiting weight variations between receptacles. Preferably the dummy loads are weighted for limiting the weight variations to not greater than 10 grams between members of each pair of receptacles.

A preferred centrifuge according to the present invention includes a base; a spindle head supported relative to the base for supporting and spinning an angularly spaced plurality of fluid receptacles about a vertical axis; a spindle motor coupled to the spindle head; a rotary encoder associated with the motor for producing an index signal and a plurality of position signals for each revolution of the spindle shaft; a driver for powering the spindle motor in response to an external signal; an enclosure supported by the base for enclosing the head means during the spinning, an upper portion of the enclosure having an openable access lid therein for accessing the fluid samples; a positioner coupled to the access lid for horizontal translation thereof between open and closed positions; a lid position sensor for signalling the closed position of the lid; and a controller for signalling the driver and the door positioner in response to the encoder, the door position sensor, and external signals.

Centrifuge Controller

Preferably the centrifuge controller is operative for (a) receiving an storing a centrifuge spin profile including a rotor spindle speed and duration; (b) indexing the rotor for advancing a selected one of the sample stations into an access position; (c) spinning the rotor in accordance with the cycle profile; and (d) stopping the rotor with a predetermined sample station at the access position. Preferably the same spindle motor is operative for both indexing and spinning the rotor for avoiding deleterious addition of inertia to the spindle head. Preferably the controller is further operative for implementing programmed acceleration and velocity of the spin profile together with a distance of rotation, the distance of rotation including a first distance corresponding to spin rate and duration, and a second distance corresponding to acceleration to the spin rate and deceleration to rest. Preferably the distance of rotation further includes a distance interval from the indexed position to the predetermined sample station for smooth deceleration from the spin rate to rest with the sample station at the access position.

Preferably the lid positioner is frictionally coupled to the lid for preventing injury in case if inadvertent contact with the lid during movement thereof. The lid positioner can include a drive wheel biasingly contacting the lid for movement thereof while limiting application of driving force thereto.

Decapper System

Before centrifuged containers are analyzed, they can be decapped in the decapper system, which can also be an included part of the workstation. The decapper system includes a receiver for clampingly holding a container, a yoke member movably mounted relative to the receiver and having means for holding a cap seated in the container, a translator for laterally moving the yoke member between open and closed positions thereof, and an elevator for raising the yoke member, in the closed position thereof, relative to the receiver to thereby remove the cap.

Preferably the decapper system also includes a collector for receiving caps from the yoke member, and an unloader for transferring removed caps from the yoke member to the collector. The means for holding the cap can include an upwardly facing ledge portion of the yoke for engaging an outwardly extending shoulder surface of the cap, the ledge portion extending under the cap in the closed position. The unloader can be implemented by a post fixedly located relative to the receiver, in combination with programmed operation of the translator and the elevator for locating the yoke member in the open position thereof with the removed cap aligned above the post, and lowering the yoke member for engagement of the cap with the post, thereby stripping the cap from the yoke member. In a preferred alternative to the ledge portion, the yoke member has a powered clamp mechanism for gripping the cap, and the unloader can be a plunger biasingly supported on the yoke, in combination with programmed operation of the translator for loading the plunger by the cap prior to activation of the gripping mechanism, the cap being ejected by the plunger upon release of the clamping mechanism.

Preferably, the decapper further includes a guide for directing the stripped caps into the receiver. Also, the decapper further includes a cap sensor for detecting and signalling the passage of caps into the receiver for verifying proper decapping.

Preferably the receiver is controllably rotatable for removal of threaded caps. The receiver can include an inflatable bladder within a rigid member and fluid-connected through a control valve to a pressure source for selectively gripping the container. In a preferred alternative, a flexible sleeve having a closed bottom encloses a portion of the container within a rigid member, a jaw mechanism in the rigid member selectively damping the container through the sleeve, the sleeve advantageously preventing spillage in case of a broken container.

The system of the present invention is useful with a wide variety of specimens, and generally is used with biological specimens such as human blood samples. However, it can also be used for non-biological specimens.

Analyzer

Typically the system comprises two analyzers, i.e., a single workstation centrifuge can serve two analyzers. However, the system can be used with one analyzer or more than two analyzers. Typically each analyzer comprises a mechanism for selectively performing at least two different analyses on a specimen, and an analyzer controller in communication with the central controller, so the central controller can instruct the analyzer controller as to what analysis to perform for each specimen. Each analyzer also includes an output system for providing analysis results to memory of the central controller. Typically each analyzer output system has an output element for providing analyzer availability information to the central controller, and the central controller has means for selectively determining which analyzer each specimen that is to undergo analysis is analyzed by.

A typical analyzer has opposed sides, a front, a top, and a back, the top having analytical equipment thereon and being accessible from the front by a user. Preferably the workstation is proximate to one of the sides of the analyzer without any obstruction of the front of the analyzer. The workstation has a front, a back, and opposed sides, and preferably the back of the workstation is proximate to the side of the analyzer. When a centrifuge is used, preferably it is proximate to one of the sides of the workstation. When two analyzers are used, preferably they are back-to-back, the back of the workstation being proximate to one of the sides of each analyzer.

In a typical analyzer, the analyzer has a base, and a pedestal sitting on the base, the pedestal having a roof. Preferably the analyzer robotic arm is on top of the roof so that it is out of the way when it is in a rest position. There can be a robotic path along the roof, and a drive for moving the robotic arm along the path, the robotic arm having a track engaging element. An extension arm can extend from the track engaging element in the same direction the path extends, with container grippers being connected to the extension arm. Preferably the extension arm is sufficiently long that when the track engaging element is at the end of the path, the robotic arm does not obstruct the top of the base of the front work area of the pedestal.

Preferably the grippers of the analyzer robotic arm are adapted for engaging container holders for lifting and transporting the holders between the analyzer receiving site and the analyzer. The holders can be sectors having a spaced pair of gripper openings in an upwardly facing wall portion thereof, the grippers having oppositely extending hook extremities for engaging a bottom surface of the wall portion through respective ones of the gripper openings. In a preferred alternative, the holders have an upstanding handle portion including a resilient member and having a cylindrical shape for facilitating effective gripping by the grippers over a range of vertical positions of the grippers relative to the holders. As used herein, "cylindrical" means having a surface that is generated by a straight line that moves parallel to a reference axis.

Transport System

The transport system (i) transports containers to and from the centrifuge receptacles, the analyzers and the decapper system; (ii) transports receptacles to and from the balance system and the centrifugation system; and (iii) transports containers in the sorting system. The transport system has a controller in communication with the central controller so the central controller can direct the transport system.

In a preferred system, the transport system includes at least two robotic arms. Each analyzer has a robotic arm for transporting the containers to and from the analyzer, and the workstation has a robotic arm for the other transport functions.

Preferably the workstation robotic arm comprises (i) a longitudinal track on the workstation, (ii) a base carriage positionable along the workstation track, the track extending proximately between opposite ends of the workstation and approximately centered laterally, (iii) a panning head controllably rotatably supported, (iv) an upper arm controllably rotatably supported on the panning head, (v) a lower arm controllably rotatably supported on an extremity of the upper arm, (vi) a wrist head controllably rotatably supported on an extremity of the lower arm, and (vii) a gripper head controllably rotatably supported therefrom on a gripper axis. The gripper head has a pair of gripper fingers extending therefrom, being controllably movable with tactile feedback toward and away from opposite sides of the gripper axis for selectively grasping and transporting containers, and holders thereof. Preferably the gripper head also includes an optical head sensor for sensing objects located proximate the gripper fingers. The head sensor can include a light source portion and a light receiver portion, and having respective source and receiver axes converging proximate the gripper axis, preferably in approximate orthogonal relation to the gripper fingers relative to the gripper axis for sensing entry of a container portion or holder extremity between the gripper fingers.

Preferably the robotic arm is provided with an indicia scanner for reading indicia of the containers and of holders of the containers, for identification of same. The indicia scanner is operative relative to a scan axis thereof, the scanner being preferably mounted to the upper arm of the robotic arm with the scan axis oriented downwardly and outwardly from proximate an upper portion of the pan head for reading indicia being both horizontally and vertically oriented when the gripper fingers are near the indicia.

Preferably the pan head is movable about the pan axis throughout an angle of greater than 180°, and the base carriage is movable to proximate opposite ends of the work station for facilitating transport of containers and holders substantially anywhere on the workstation. Further, the gripper head is preferably locatable in overhanging relation to the workstation for accessing an external process station.

It is desirable that the central controller track containers by the holders in which they are located. Accordingly, preferably the indicia reader can read the holder identification indicia, the reader output element providing holder identification indicia to the central controller for tracking containers according to the respective holders.

In other aspects of the invention, a centrifuge system includes the plurality of receptacles; the centrifuge having the spindle, centrifuge controller that indexes the spindle for automatic loading and unloading of the receptacles, and the powered lid; the balance system; and the transport system for transporting the containers and the receptacles between the balance system and the centrifuge.

A preferred balance system for the centrifuge receptacles comprises the above-identified balance system wherein the locations of containers in receptacles are correlated with weights thereof for symmetrical loading of each receptacle.

A preferred decapper according to the present invention comprises the above-identified decapper systems, including the capability of unscrewing the caps.

Test tubes containing specimens to be analyzed come in different heights and different diameters. Accordingly, the holders and centrifuge receptacles are preferably provided with spring fingers.

During use of the workstation, it is possible that the workstation becomes misaligned with the analyzer so that the analyzer robotic arm does not adequately grip holders containing containers for analysis, and/or improperly delivers holders containing analyzed specimens to the workstation. Accordingly, preferably the sites at which holders are maintained by the workstation for delivery to the analyzer or for receipt by the analyzer are provided with an adjustment mechanism for independently aligning the sites, without moving either the analyzer or the workstation. The adjustment mechanism includes a rotatable and translatable platform having at least one holder site thereon, and a clamp activator for selectively holding the platform in a fixed position on the workstation.

Method of using the System

A method according to the present invention makes uses of this system. In the method of the present invention, instructions for the processing of each container according to the container identification indicia are stored in the memory of the central controller. The presence of a holder in the system is detected and signaled to the central controller. Container identification indicia are read and also signaled to the central controller. The containers are transported with the robotic arm to a plurality of sort sites according to the processing instructions that are in the memory storage. Selected specimens are sorted, and optionally centrifuged, decapped, and analyzed.

For centrifugation of selected specimens, containers containing the selected specimens are transported to the centrifuge receptacles and loaded into a selected receptacle with the workstation robotic arm according to processing instructions. The loaded receptacles are then balanced, such as by loading pairs of the receptacles using symmetrical loading patterns having equal numbers of loaded positions, and/or putting in "dummy" test tubes in the receptacles that need extra weight. The balanced receptacles are placed in the centrifuge, and containers are centrifuged for a time and rate according to instructions from the central controller. The centrifuge is unloaded by stopping the centrifuge, indexing the centrifuge to selected unloading positions, and removing the receptacles from the centrifuge with the robotic arm in response to signals from the central controller.

In the analysis operation, each analyzer provides analyzer availability information to the central controller, and the central controller determines which analyzer each specimen that is to undergo analysis is analyzed by.

Accordingly, in the system and method of the present invention, sample preparation for analysis of specimens is automated. Moreover, the system can be used with existing equipment, i.e., existing analyzers can be utilized by retrofitting them with a robotic arm and data communication with a central controller. Moreover, the system can recognize and expeditiously handle STAT samples. Further, the system minimizes human handling of specimens. This reduces health risks associated with contacting biological samples and the risk of contaminating specimens.

DRAWINGS

These and other features, aspects and advantages of the present invention will become better understood from the following description, appended claims, and accompanying drawings where:

FIG. 1 is a perspective view of a system according to the present invention, comprising a workstation, a centrifuge, and two analyzers;

FIG. 2C being for an analysis subsystem of the supervisor of FIG. 2A;

Figure 2B:
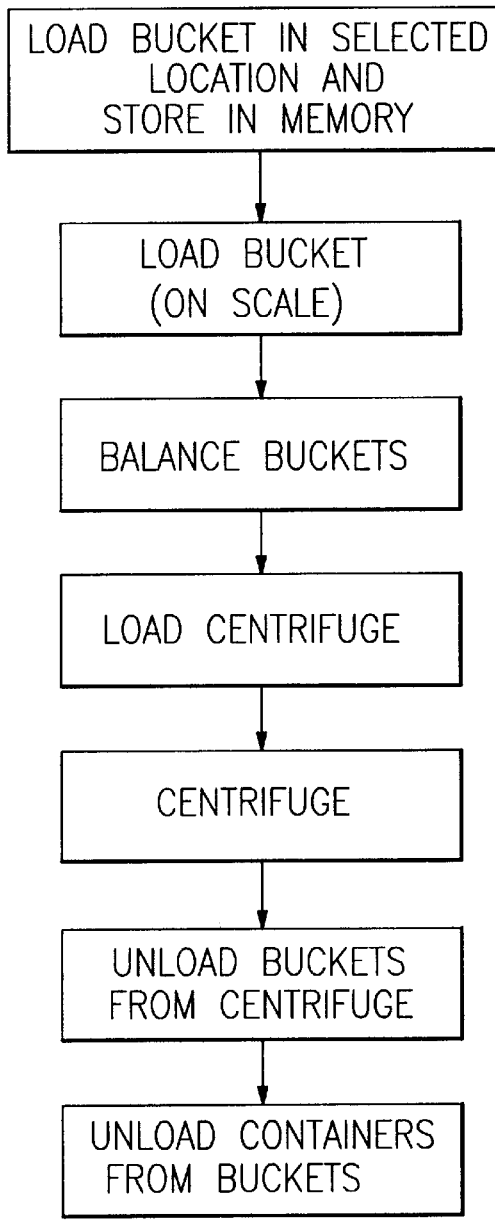
FIGS. 2A–2C are flow charts of the steps of processing containers using the system of FIG. 1, FIG. 2A being for a process supervisor, FIG. 2B being for a centrifugation subsystem of the supervisor of FIG. 2A.
Figure 2C:
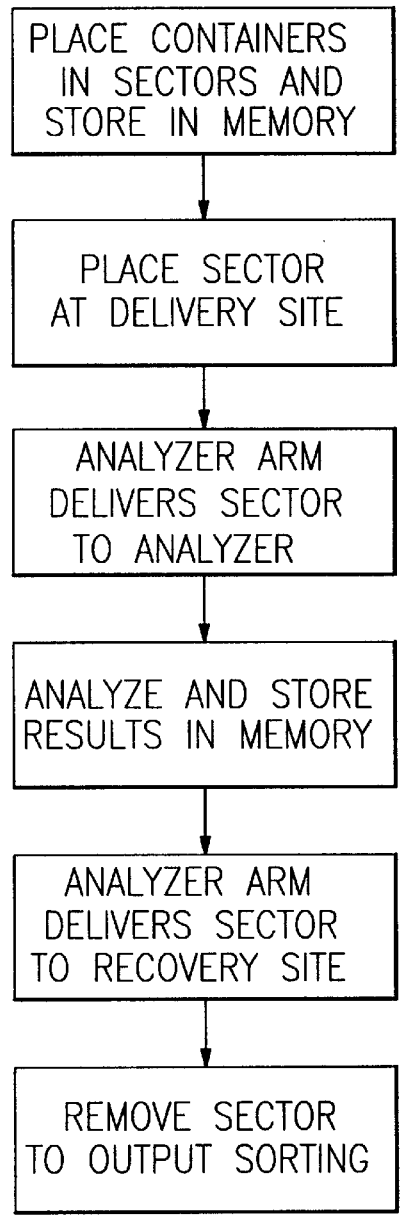
Figure 2D:
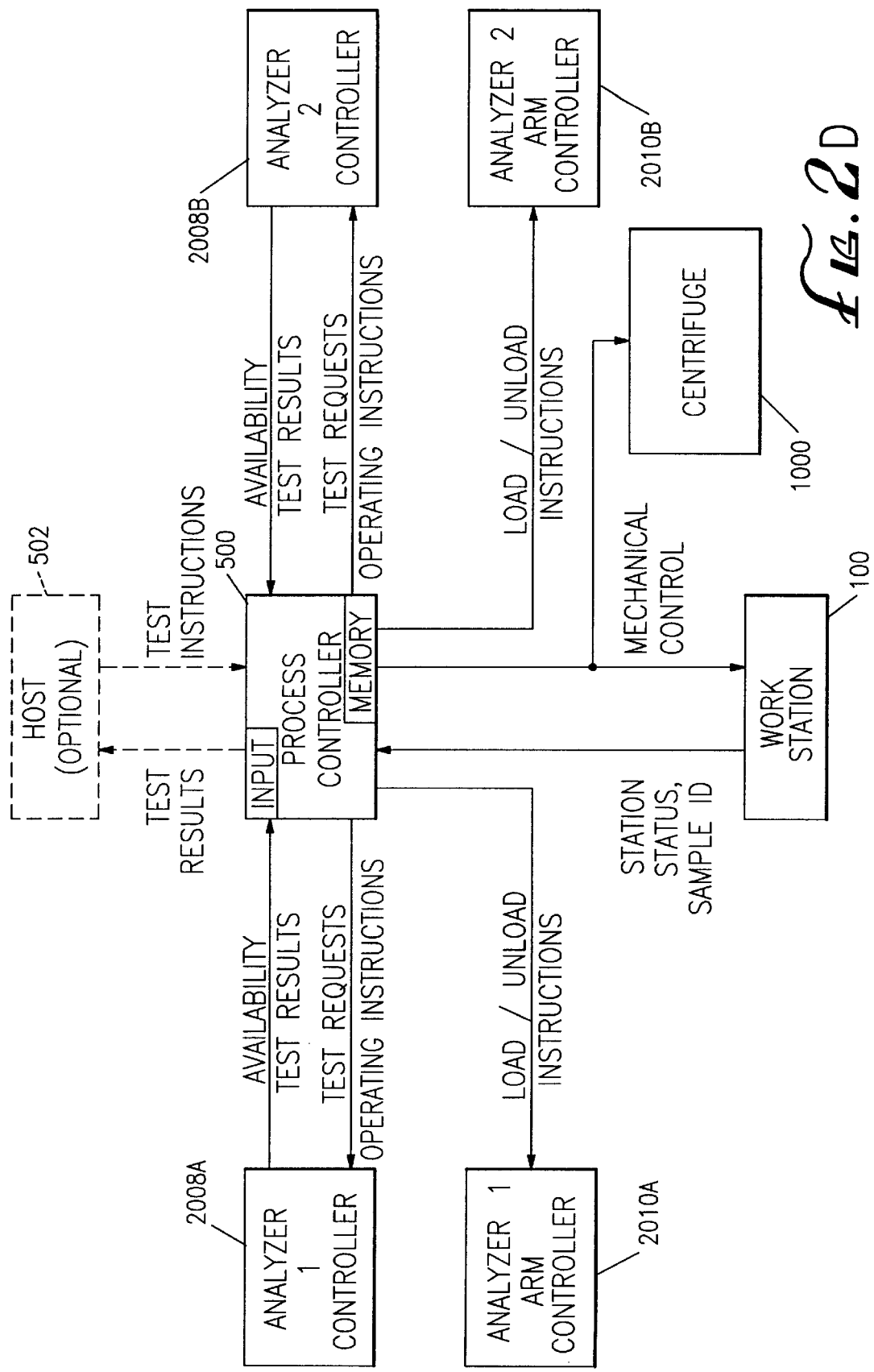
Figure 4:
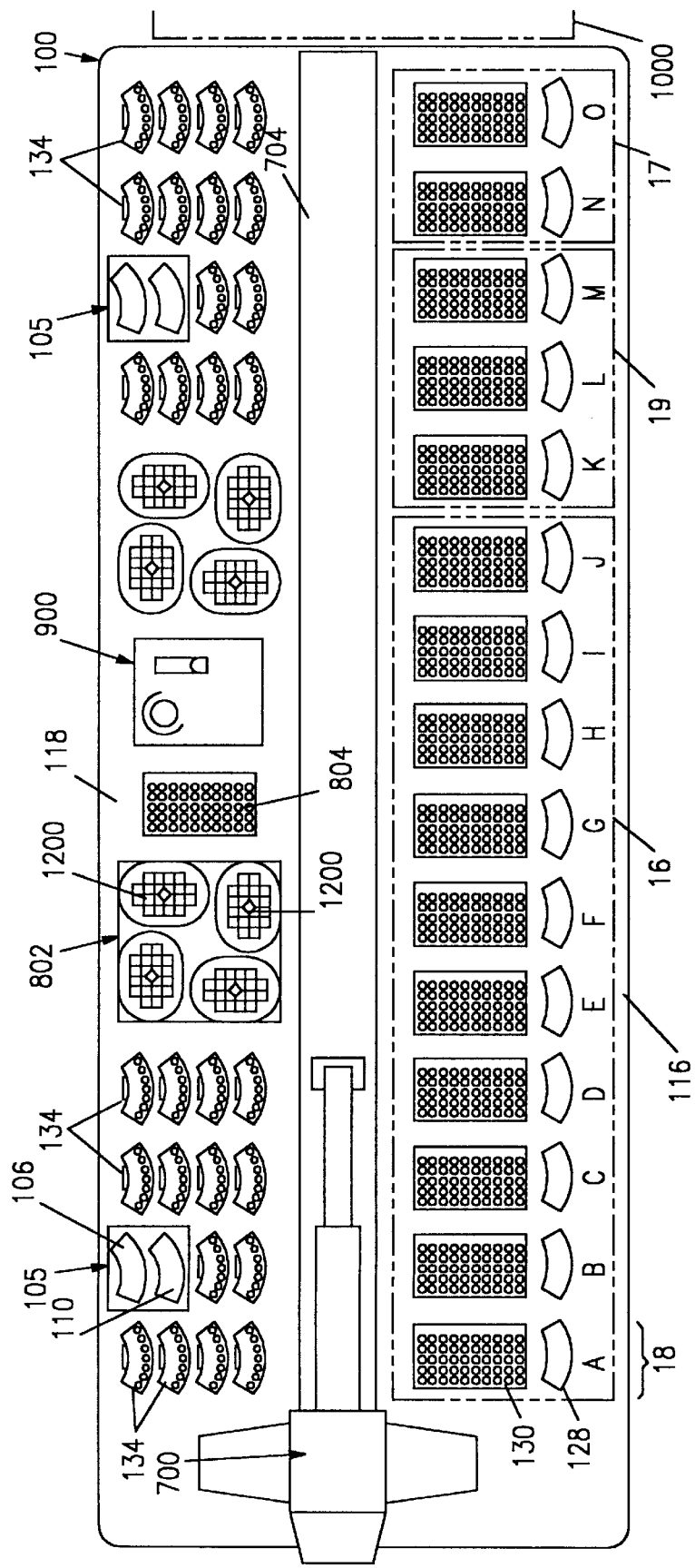
Figure 9A:
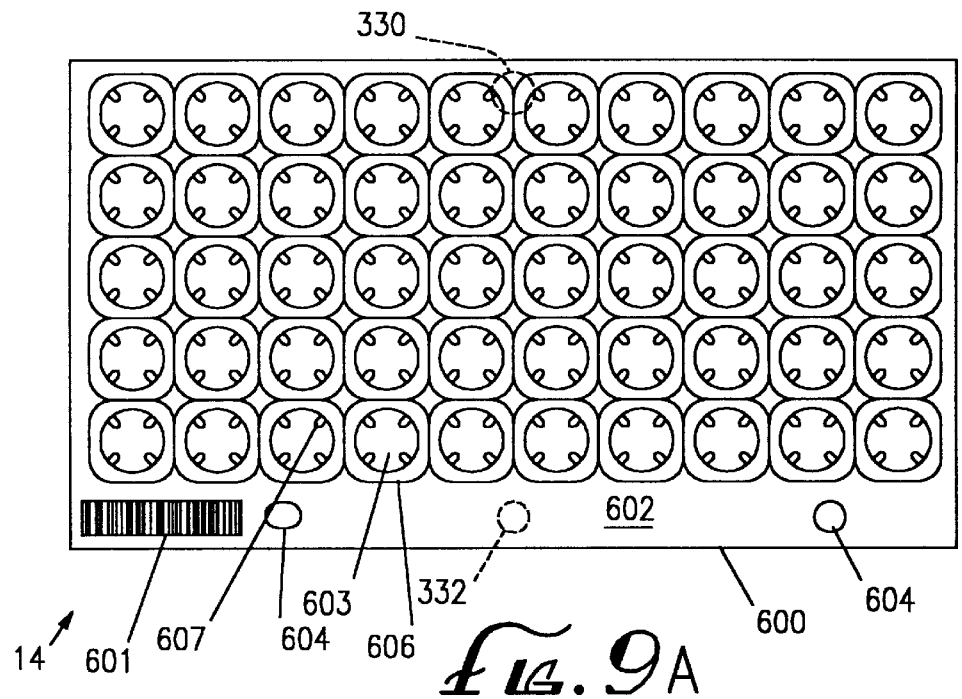
Figure 9B:
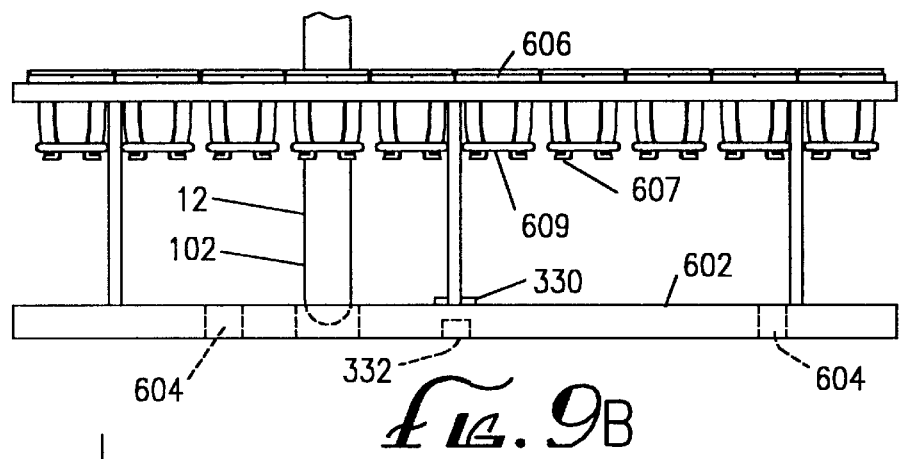
Figures 9C, 9D:
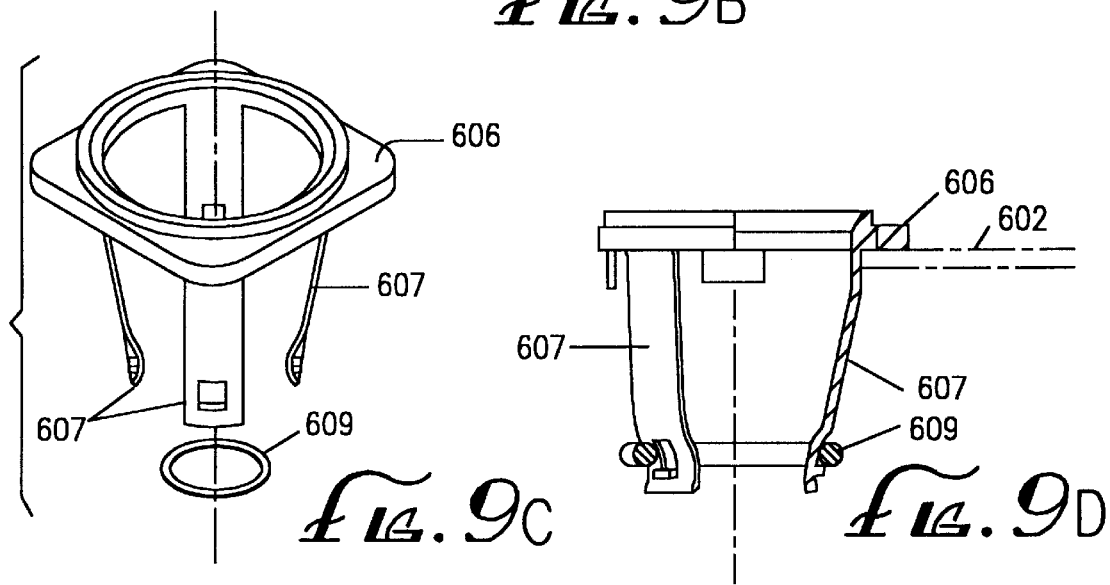
Figure 12A:
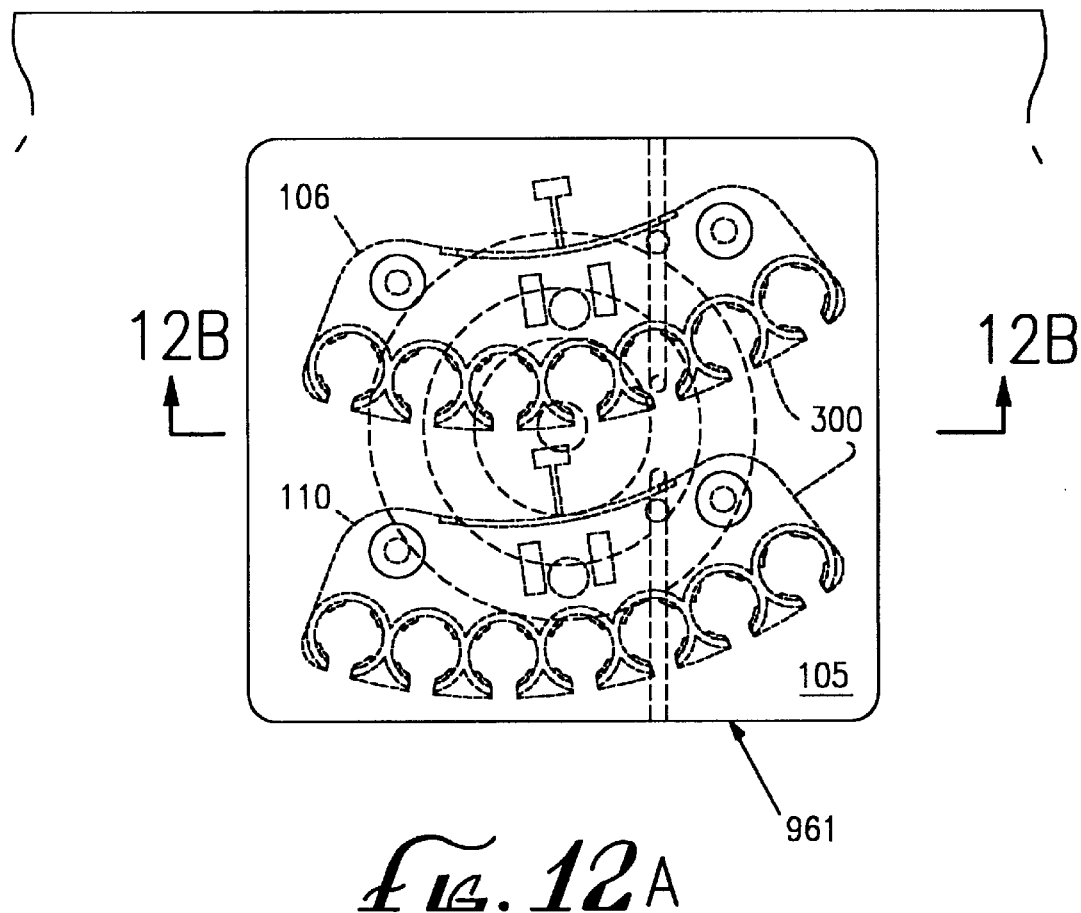
Figure 12B:
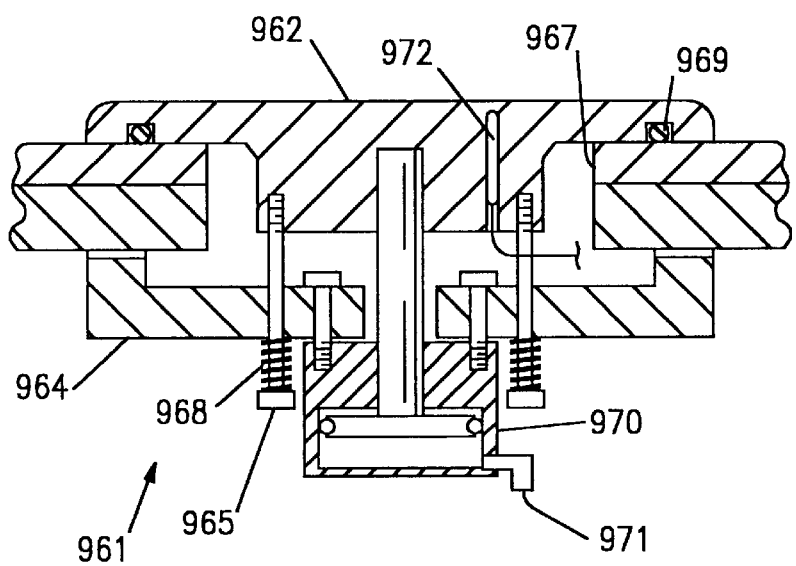
Figure 13A:
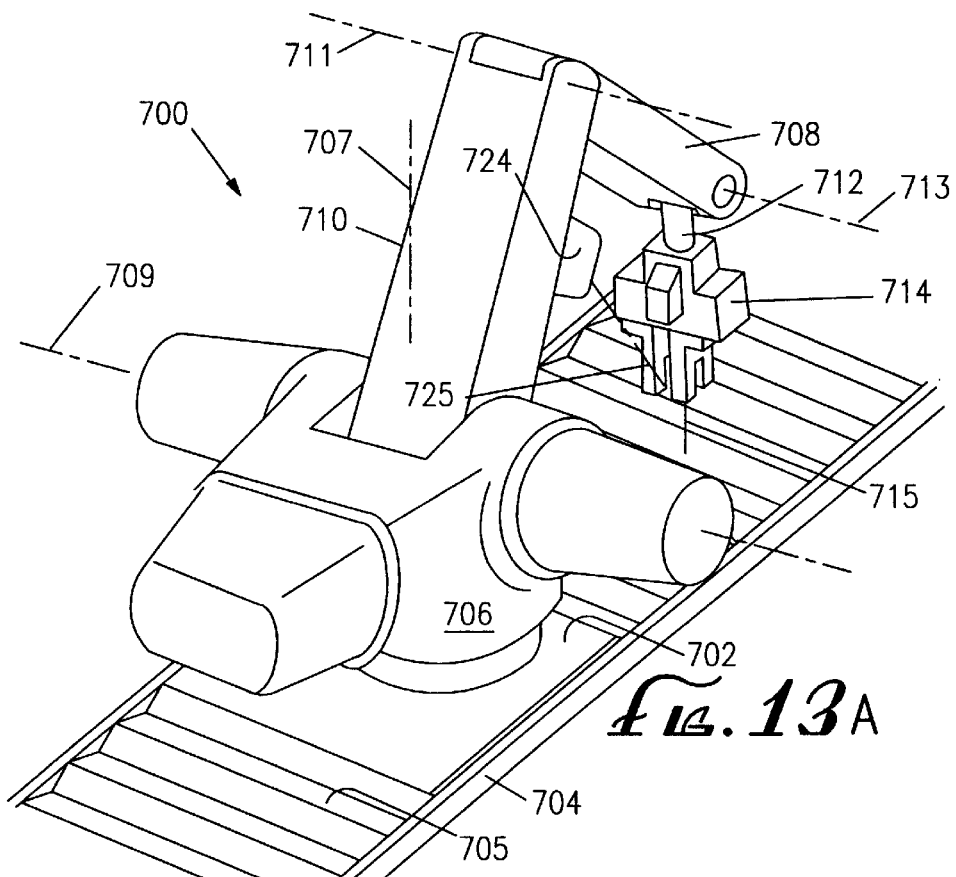
Figure 13B:
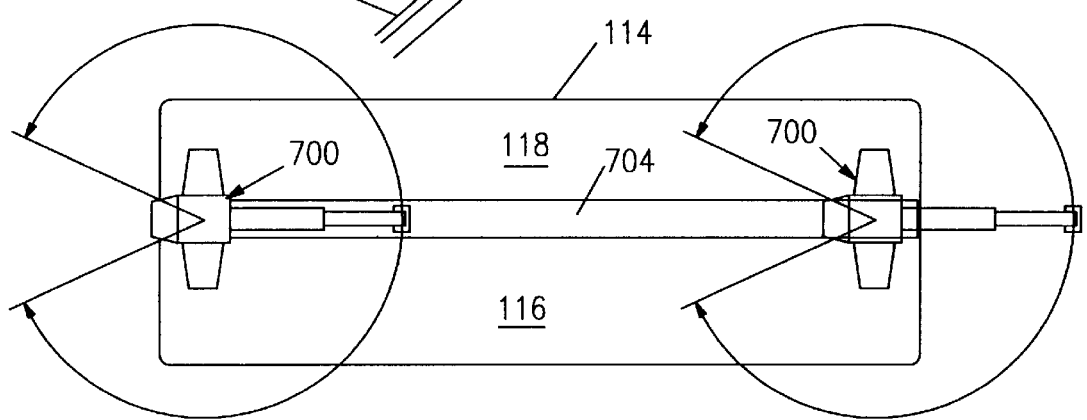
Figure 14B:
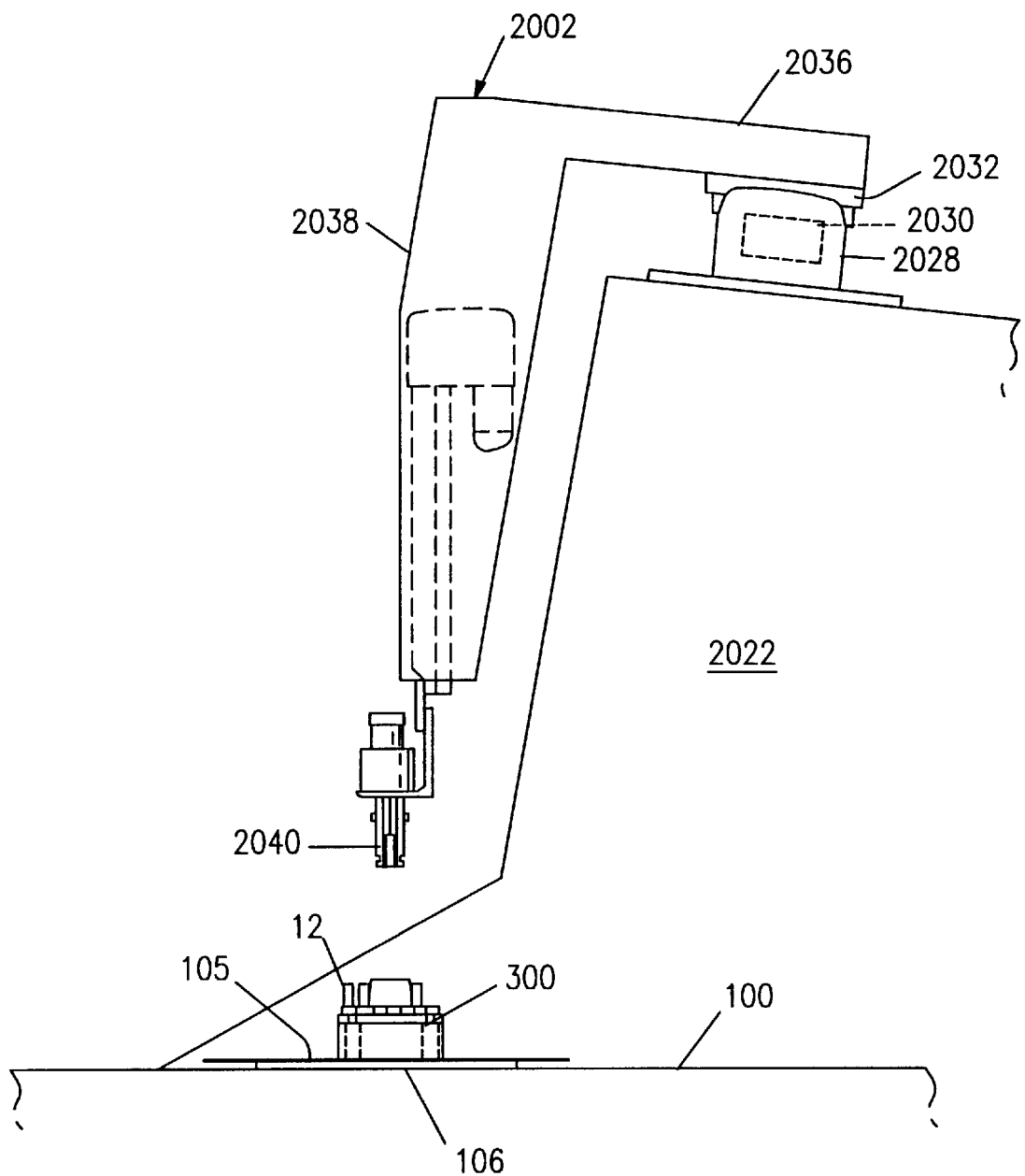
Figure 16A:
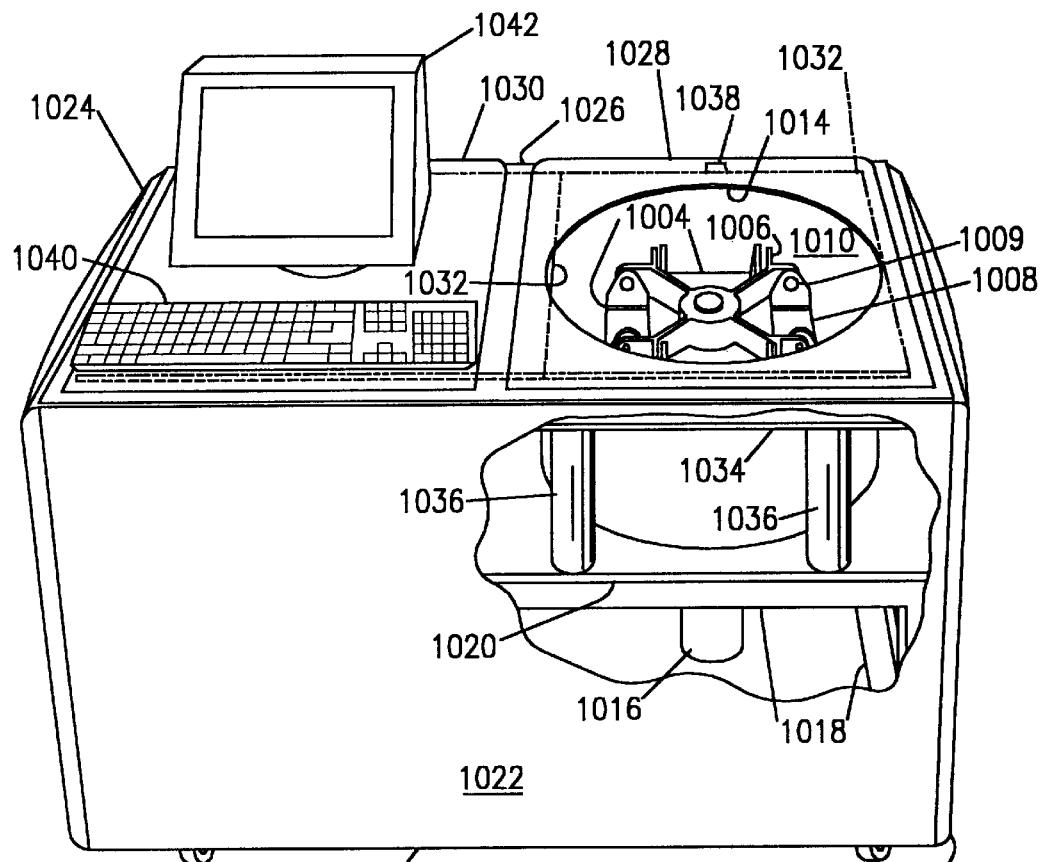
Figure 16B:
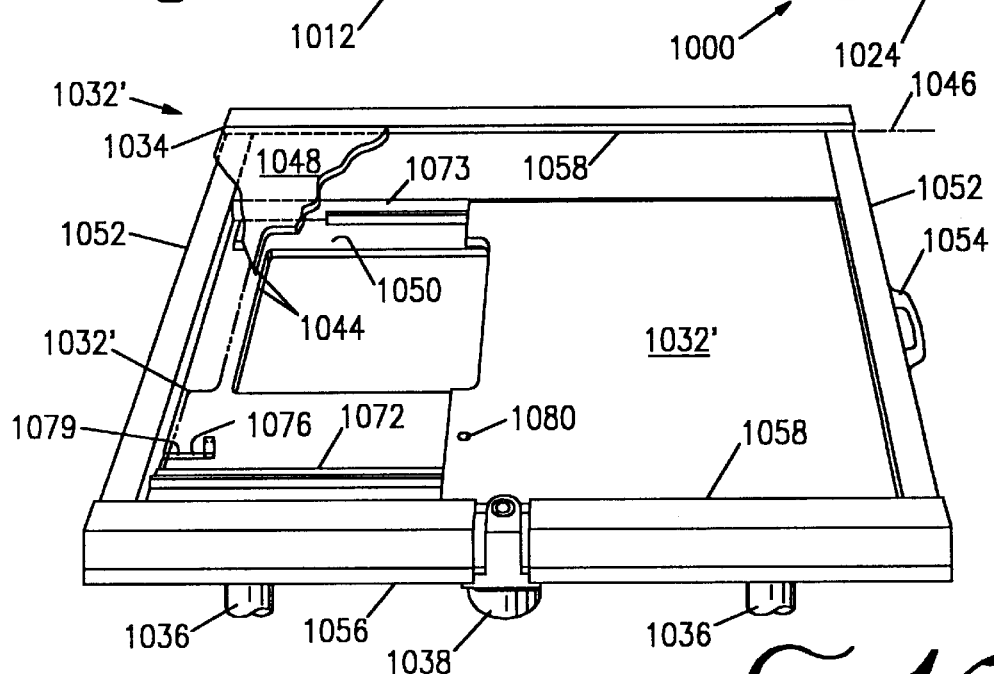
Figure 16C:
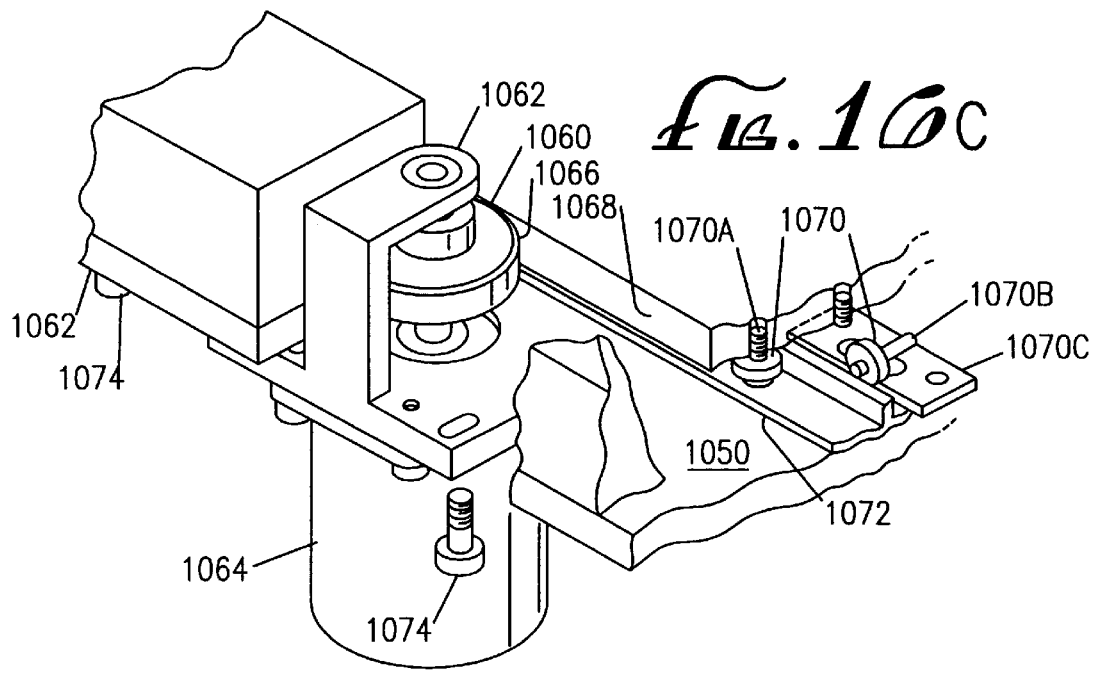
Figure 16D:
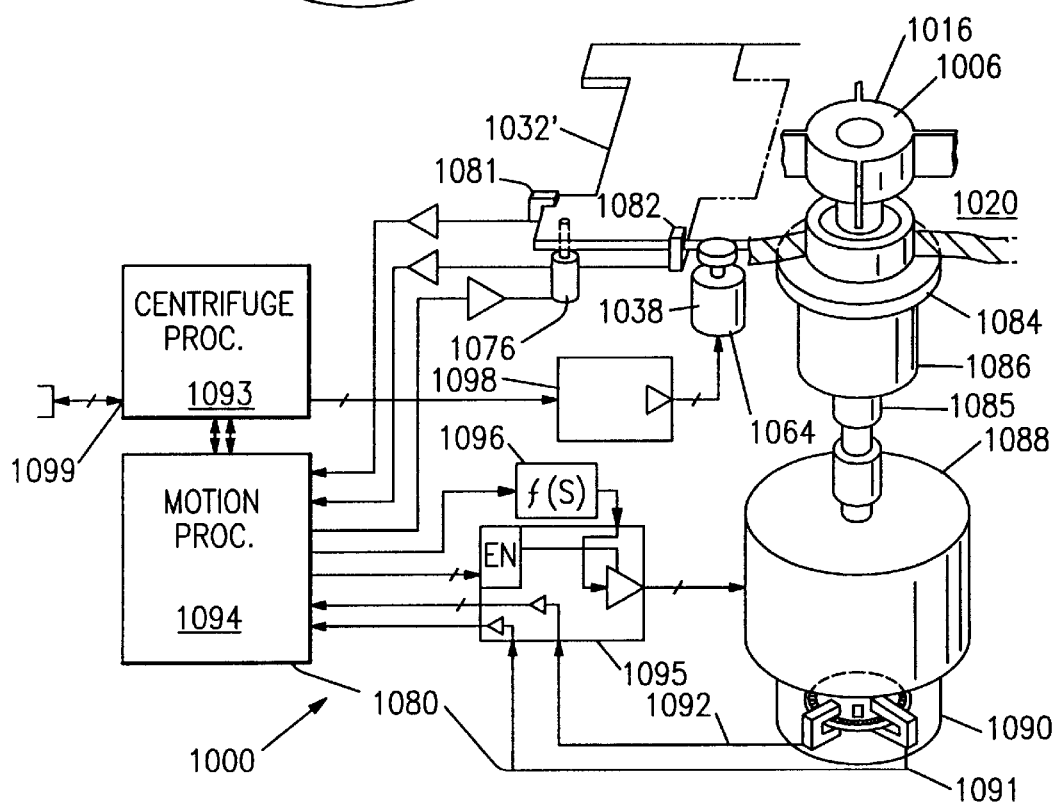
Figure 10E:
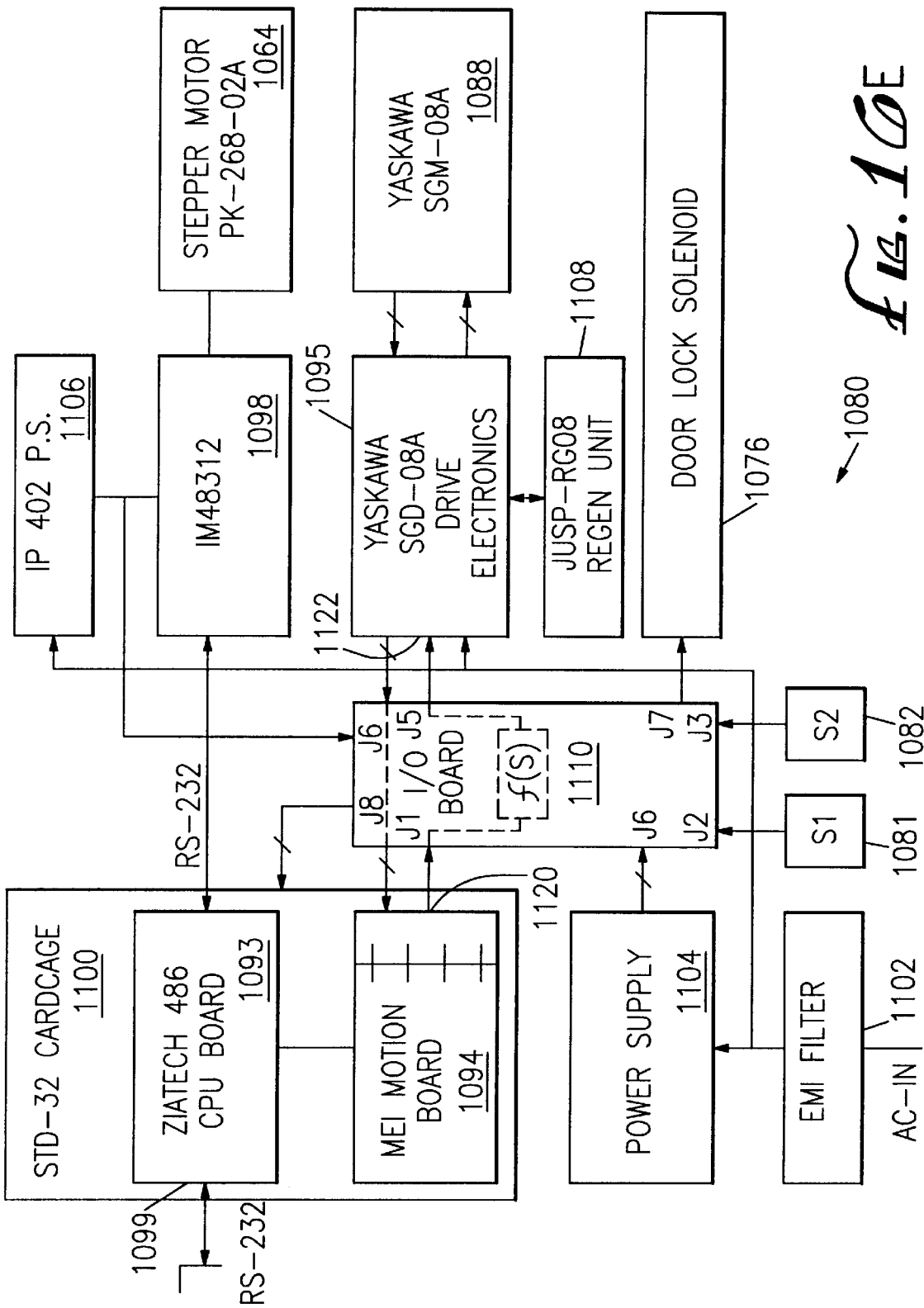
Figure 10F:
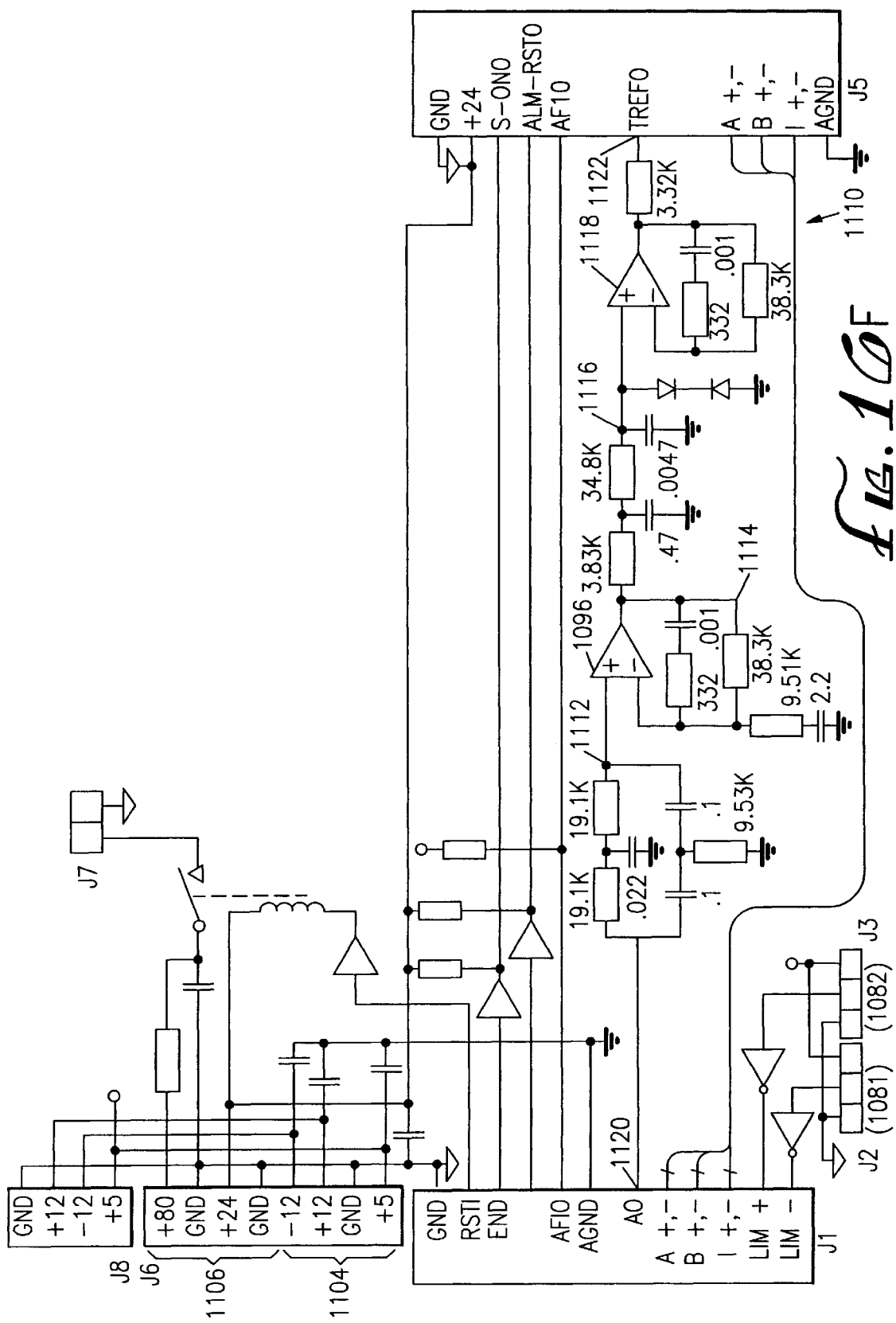
Figure 18F:
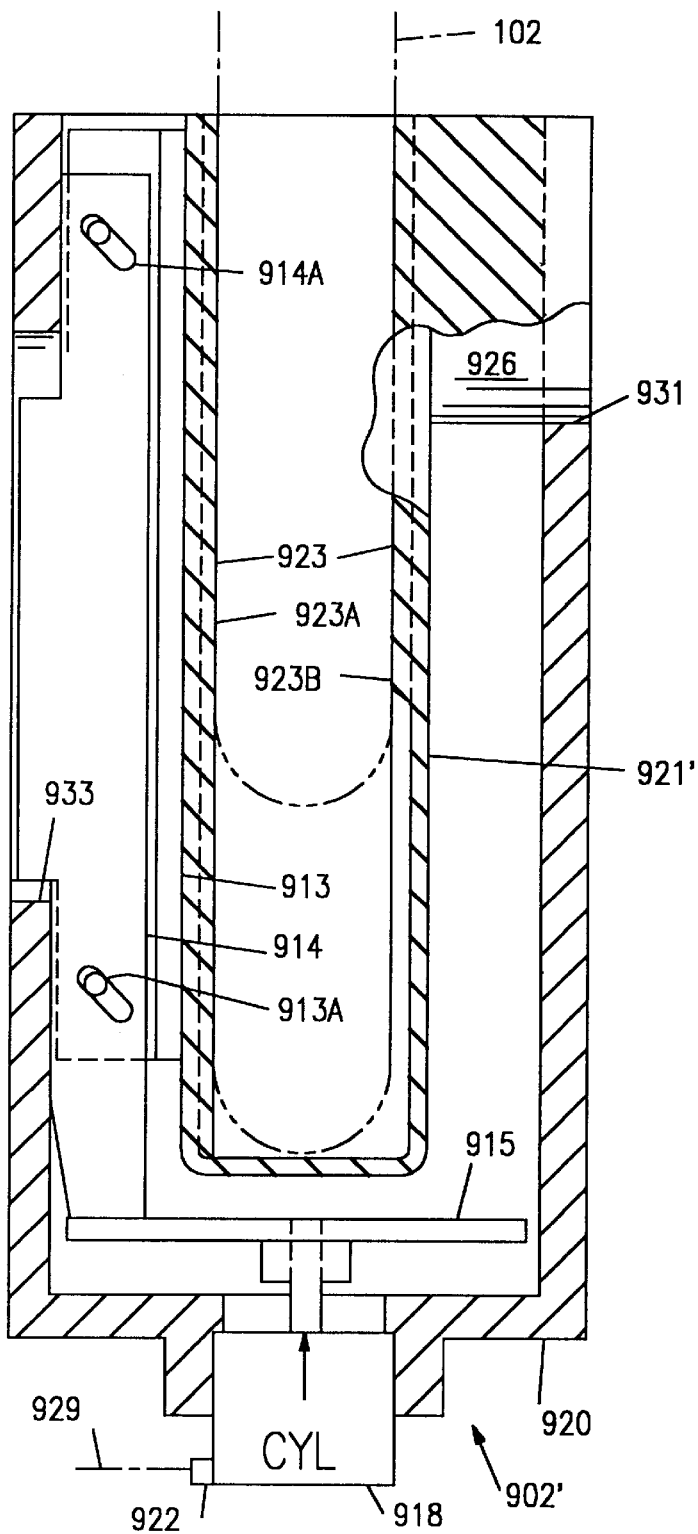

FIG. 2D schematically shows how the process controller of the system of FIG. 2A controls the workstation, analyzer, and centrifuge;

FIGS. 3A–3E are plan views of different layouts of a workstation, analyzers, and a centrifuge;

FIG. 3F is a plan view of a workstation and centrifuge according to the present invention, being used with a conveyor system;

FIG. 3G is a plan view of an analyzer according to the present invention being used with a conveyor system;

FIG. 4 is a schematic plan view of the work station of FIG. 1;

FIG. 5 is a view of the workstation of FIG. 1, similar to that of FIG. 4, showing the location of positioning pins used for locating holders, and the location of detectors for detecting holders;

FIGS. 6A–6C show different types of positioning pins used with the workstation of FIG. 5;

FIG. 7 is a partial sectional view of the workstation of FIG. 5, showing a detector for detecting the presence of a holder;

FIG. 8A is a perspective view of a sector for use with the system, and showing how positioning pins of the workstation interface with the sector;

FIGS. 8B and 8C are top and bottom plan views of the sector of FIG. 8A;

FIG. 8D is a partial perspective view showing an alternative configuration of the sector of FIG. 8A;

FIGS. 9A and 9B are a top plan view and a side elevation view, respectively of a rack for use in the system of the present invention;

FIGS. 9C and 9D are exploded perspective and fragmentary side sectional views of an insert portion of the rack of FIGS. 9A and 9B;

FIG. 10A is a top plan view of a bucket seated in a spindle head cradle of the centrifuge of the system of the present invention;

FIG. 10B is a side elevational view of the bucket of FIG. 10A;

FIG. 10C is a bottom elevational perspective view of the bucket of FIG. 10A, and showing an alternative configuration of the centrifuge cradle;

FIGS. 11A–11D show different loading patterns for the centrifuge buckets according to the present invention;

FIG. 12A is a top plan view of a delivery site adjustment mechanism of the workstation of FIG. 1;

FIG. 12B is a sectional view of the adjustment mechanism, taken on line 12B—12B of FIG. 12A;

FIGS. 13A—13D show details of the robotic arm of the workstation of FIG. 1, FIG. 13A being a perspective view; FIG. 13B being a schematic plan view showing a range of movement of the robotic arm relative to the workstation of FIG. 1; FIG. 13C being a perspective view, partly exploded, of a gripper head and an optical head sensor of the robotic arm; and FIG. 13D being a perspective view as in FIG. 13C, showing an alternative configuration of the optical sensor;

FIGS. 14A and 14B are front and side elevational views of one of the analyzers of the system of FIG. 1, FIG. 14B being taken on line 14B—14B in FIG. 14A;

FIGS. 15A—15G show details of a gripper portion of the robotic arm of the analyzer of FIG. 14A, FIGS. 15A and 15B being front and right side elevational views; FIG. 15C being a right side view as in FIG. 15B, with the gripper portion lowered into engagement with a sector; FIGS. 15D and 15E being sectional views on line 15D—15D of FIG. 15A, FIG. 15E showing engagement with a sector; and FIG. 15G is a perspective view showing an alternative configuration of the gripper portion;

FIG. 16A is a fragmentary front elevational perspective view of a centrifuge unit of the system of FIG. 1;

FIG. 16B is a fragmentary detail rear perspective view showing an alternative configuration of an access door portion of the centrifuge unit of FIG. 16A;

FIG. 16C is a detail perspective elevational view showing a drive mechanism for the access door of FIG. 16B;

FIGS. 16D and 16E are a pictorial block diagram and a circuit block diagram of the centrifuge unit of FIG. 16B;

FIG. 16F is a simplified circuit diagram of a circuit interface module of the centrifuge unit of FIG. 16B;

FIG. 16G is a flow chart for a computer program of the centrifuge unit of FIG. 16B;

FIGS. 17A and 17B are a top plan view and a side elevational view, respectively, of the balance subsystem of the system of FIG. 1;

FIG. 18A is a perspective view of the decapper subsystem of the system of FIG. 1;

FIG. 18B is a schematic view showing the decapper system of FIG. 18A on the workstation;

FIG. 18C is a perspective view showing an alternative configuration of a portion of the decapper system of FIG. 18A;

FIGS. 18D and 18E are side sectional elevational and bottom views of the decapper system portion of FIG. 18C;

FIG. 18F is a fragmentary side elevational view of an alternative receiver portion of the decapper system portion of FIG. 18A FIG. 19 is a diagram of a pneumatic subsystem of the system of FIG. 1;

FIGS. 20A and 20B are exploded perspective and side elevational views of a workstation table of the system of FIG. 1; and FIG. 21 is a fragmentary sectional elevational view of a door portion of a protective shield of the workstation.

DESCRIPTION

System Overview

With reference to FIGS. 1, 2, 4, 8A, 9A, and 10A, a system 10 according to the present invention comprises, as its main components, a workstation 100, a centrifuge unit 1000, and at least one analyzer 2000, and typically two analyzers, designated 2000A and 2000B. The workstation 100 is loaded with containers 12, such as test tubes 102 (see FIG. 8A) by an operator. The test tube 102 is provided with identification indicia, namely a bar code 104 and a cap 103. Typically the containers are held in a holder 14, such as a sector 300 (FIG. 8A) or a test tube rack 600 (FIG. 9A). For centrifugation, the containers 12 are typically transferred to receptacles or buckets 1200 (FIG. 10A).

As shown in FIG. 2A, a process supervisor 200 of the system 10 includes a detect input step 202 for detecting presence of containers 12 at an input location 16 (FIG. 4) of the workstation 100. In a container select step 204, detected containers 12 are then selected for processing. Processing is on a first-in, first-out basis, except for containers that need priority or "STAT" treatment. Those containers 12 are placed by the operator within a priority region 18 on the workstation 100 for priority processing.

After a container 12 is selected for processing, the container ID, i.e., the bar code 104, is read in a container ID read step 206, and main process components are defined in a process select step 208, based on processing specified for the container 12. The container is then processed in one or more of a centrifugation step 210, a decapping step 212, an analysis step 214, and an output sorting step 216.

For a specimen that is to undergo complete processing, the container is sent by the centrifugation step 210 to the centrifugation subsystem for centrifuging in the centrifuge unit 1000 (FIGS. 16A–16G). The centrifuged container is then processed in the decapping step 212 by a decapping subsystem 900 (FIGS. 18A and 18B). Decapped samples are then transported in the analysis step 214 for analysis on any available analyzer. Substantially any type of analysis that is effective for biological materials can be done, including analysis of urine, blood, and cerebrospinal fluid. Moreover, the system 10 of the present invention can be used for industrial analysis, and thus is not limited to biological substances.

After analysis on one or both analyzers 2000, the containers are returned to the workstation 100, and then subjected to output sorting in the output sorting step 216, wherein each container 12 is put into a specified holder 14. Some of the holders 14 are for containers that will undergo further analysis or processing; other holders being for containers whose processing is completed.

As further shown by FIG. 2A, containers 12 need not go through all of the processing steps 210, 212, 214, and 216. For example, the workstation 100 can be used just for output sorting. Alternatively, it can be used for containers that do not need centrifugation and/or decapping, the supervisor 200 using the results of the process select step 208 for determining subsequent ones of the processing steps. For example, appropriate ones of the containers 12 can be sent straight to analysis and then output sorting.

The centrifuge unit 1000, which is described in detail below, is designed for centrifuging containers that are loaded in receptacles or buckets 1200 (FIG. 10A). Each bucket 1200 holds multiple containers to be centrifuged, and the centrifuge 1000 is adapted for centrifuging multiple buckets 1200, typically four. It is important for the proper operation of the centrifuge and to avoid damage to the centrifuge, that buckets loaded across from each other in the centrifuge have substantially the same weight, within typically about 10 grams.

The centrifugation step 210 supervises the centrifugation subsystem generally as shown in FIG. 2B. In the centrifugation subsystem, the buckets 1200 are loaded in selected locations, and the location for each container in each bucket is stored in memory. The buckets are loaded in a predetermined order to be approximately balanced as well as reasonably permitted by the specific complement of containers 12 requiring centrifugation. Preferably the loading is monitored by a balance system 800 (FIGS. 17A, 17B) and the buckets 1200 are further balanced to comply with a predetermined tolerance. The balanced buckets are then loaded into the centrifuge 1000, centrifuged, and then unloaded. The individual containers 12 are then unloaded from the buckets 1200 for further processing.

The analysis step 214 supervises the analysis subsystem generally as shown in FIG. 2C, the containers 12 (typically the test tubes 102) being placed in sectors 300, and data corresponding to the particular sector in which the container is located is stored in the memory of a process controller 500. As shown in FIG. 1, a loaded sector 300 is placed at a delivery site 106 of the workstation 100 by a robotic arm 700 of the workstation 100, there being a delivery site 106 for each of the analyzers. An analyzer robotic arm 2002 picks up the sector from the delivery site 106 and delivers it to an analyzer transfer site 2004. The analyzer 2000 then proceeds to analyze the specimen according to processing instructions from the process controller, and stores the results of the analysis in the memory of the process controller 500. Then the analyzer robotic arm 2002 picks up the sector 300 containing analyzed specimens from the analyzer transfer site 2004 and returns them to a workstation receiving site 110. The sector 300 at the workstation receiving site 110 is then picked up by the workstation robotic arm 700 for sorting.

FIG. 2D shows the data and operating instruction information flow between the various components of the system 10. The system includes the central process controller 500, which can be typically a computer system. Exemplary of the computer systems that can be used are industrial counterparts of commonly available 32-bit personal computers having read-write memory in the several megabyte range.

The controller 500 is provided a suitable input device such as a keyboard, touch screen, card reader, or another computer, for inputting processing instructions into memory for processing each of the containers 12 according to container identification indicia.

The process controller 500 provides instructions for mechanical control of the workstation 100, using feedback in the form of station status and sample identification data. The analyzers 2000 are provided with respective controllers 2008A and 2008B as well as a separate controllers 2010A and 2010B for the robotic arms 2002. The analyzer controllers 2008A and 2008B can be commercially available industrial microcomputers, or counterparts of the process controller 500. Each of the analyzer controllers 2008A and 2008B has an output interface for providing the central controller 500 information from each analyzer about availability, whether the analyzer can perform a particular test, and test results. In return, the process controller 500 provides test requests to each analyzer 2000 for each specimen, as well as operating instructions through an input interface of the corresponding controller 2008A or 2008B. Similarly, the process controller 500 provides to each of the analyzer robotic arm controllers 2010A and 2010B various load and unload instructions. Suitable devices for the analyzer robotic arm controllers 2010A and 2010B are available from a variety of industrial robot suppliers.

Based on the analyzer availability information provided by each analyzer output to the central controller 500, the central controller selectively determines which analyzer to use for each specimen. This can be effected by software loaded in the controller memory, where the software compares analyzer availability data against the tests required by the specimen. The analyzer availability data includes what tests each analyzer is capable of performing, and analyzer status information, such as whether reagents are loaded for particular tests and analyzer backlog.

The process controller 500 also provides mechanical control instructions to the centrifuge unit 1000, and receives status information from the centrifuge unit.

Optionally, the entire system can be interfaced with a host computer 502. The host computer 502 can be interfaced with multiple systems, each system containing a workstation, a centrifuge, and one or more analyzers. The host computer can be used for inputting instructions for each specimen to the process controller 500, and the test results can be reported by the central process controller 500 to the host computer 502.

The interfaces between the components of the system, i.e., output elements, output system elements, and input system, can be conventional data connections, such as RS 232 connectors with interconnecting cables, buses, and data transport mechanisms such as IR transfer or direct hard wiring.

Layout of System Components

As shown in FIG. 1, the workstation 100 comprises a table 112 having a table top 114. The workstation has a front or input section 116, a rear or analyzer section 118, and two opposed sides 120. The front has placement locations for placement of holders 14 for holding containers 12 that are to be processed, containers whose processing has been completed, and containers which have been partially processed. Down the middle of the table is a track 704 for the robotic arm 700.

The system is adapted to be used with many configurations of holders 14. For example, it can be used for sectors 300 as shown in FIGS. 8A, 8B, and 8C, which hold a small number of test tubes 102. Sectors 300 are particularly useful for containers which need to undergo identical processing. As detailed below, the workstation robotic arm 700 has grippers 726 adapted to grip not only individual containers 12 but also the sectors 300, so that a group of containers 12 can be transported for various processing steps simultaneously. The workstation 100 can also be used with racks 600, as shown in FIG. 9, which are capable of holding multiple containers. The containers 12, which typically are test tubes 102, are removed one by one from the rack 600 for processing. Preferably the racks 600 are placed closer to the robotic arm track 704 than the sectors 300, to help speed up and increase the throughput of the system. On the analyzer section 118 of the workstation 100, there are located sectors 300 containing containers for delivery to and to be received from the analyzers 2000.

As shown in FIG. 1, the workstation robotic arm 700 is preferably centrally located on the table 112 for easy access both to the front input section 116 and the analyzer section 118 of the table. Also, the centrifuge 1000 is preferably positioned at one of the sides 120 of the workstation 100, for permitting operator access to the full length of the front or input section 116 of the table 112, the rear or analyzer section 118 being reserved for access by the analyzers 2000.

In the layout of FIG. 1, the analyzers 2000 are positioned with their sides proximate to, and preferably abutting, the workstation 100, with the two analyzers 2000 being back-to-back. In the configuration of FIG. 1, the workstation 100 does not interfere with operation of either analyzer, and neither analyzer interferes with operation of the workstation. Moreover, the centrifuge 1000, being located at one of the ends of the workstation, is likewise out of the way of the analyzers and the workstation. The analyzers are substantially identical, differing in that one (2000A) is "right armed" with its robotic arm 2002A positioned to reach to the right to the workstation 100, and second analyzer 2000B is "left armed" with its robotic arm 2002B positioned to reach to the left to the workstation 100.

FIG. 3A is a top plan view of the layout of the system shown in FIG. 1. Alternative layouts are possible, such as shown in FIGS. 3B–3F. The layout of FIG. 3B is the same as that of FIG. 3A, except that the centrifuge 1000 is placed in a U-shaped space formed by the workstation 100 and the two analyzers 2000, up against the back 2020 of the base 2012 of both workstations.

In the version of the invention shown in FIG. 3C, the layout is the same as that shown in FIG. 3B, except that the second analyzer 2000B is placed against the end of the workstation 100 that is distal from the first analyzer.

In the layout of FIG. 3D, the two analyzers 2000 are placed on opposite sides of the workstation 100, thereby forming a "cross," with the right hand analyzer 2000A up against the rear 118 of the workstation and the left hand analyzer 2000B against the front 116 of the workstation 100. The centrifuge 1000 is at one of the ends of the workstation, as in the layout of FIG. 3A.

The layout of FIG. 3E is similar to that of FIG. 3D, except the two analyzers 2000 are positioned at the centrifuge end of the workstation 100 rather than in the middle of the workstation. The layout of FIG. 3E is advantageous compared to that of FIG. 3D in that the workstation input side is not obstructed by either analyzer.

As is evident from these various layouts, it is possible to position the workstation and centrifuge 1000 so that they do not obstruct access to either analyzer.

The workstation and centrifuge of the present invention are not limited to use in direct conjunction with analyzers as shown in FIGS. 3A–3E. Instead they can be used with the conveyor system that includes a conveyor 126, as shown in FIGS. 3F and 3G. In the version of FIG. 3E, the robotic arm 700 of the workstation picks up containers, generally in sectors, from the conveyor 126, processes the containers, and optionally the containers are centrifuged. Then processed containers are returned to the conveyor 126.

In the version of FIG. 3G the conveyor cooperates with the analyzer 2000 whose robotic arm 2002 picks up and delivers containers, and/or sectors, to the conveyor 126.

Analyzers

The analyzers 2000 shown in FIG. 1 are Synchron CX analyzer units available from Beckman Instruments of Fullerton, Calif., being modified or retrofitted to incorporate the robotic arms 2002 as described herein. As also shown in FIGS. 14A and 14B, each analyzer 2000 has a base 2012 having opposed sides 2014, a front 2016, a top 2018 and a back 2020. The top 2018 has the analyzer transfer site 2004 and analytical equipment thereon and is accessible from the front by a user. A pedestal 2022 is provided on the back portion of the top 2018 of the base 2012, the pedestal 2022 having a front work area 2024 and a roof 2026. On top of the roof 2026 is a transport mechanism including the robotic arm 2002, for automated transport of specimens from the workstation 100 to the analyzer 2000, and for transport of the analyzed specimens from the analyzer 2000 to the workstation 100. A path or track 2028 having a drive 2030 therein extends across the roof 2026 for moving the robotic arm 2002 along the path 2028. The robotic arm 2002 has a track engaging element 2032, and an extension arm 2034 extending from the track engaging element 2032 in the same direction the path 2028 extends. From the end of the extension arm 2034, there is a forwardly extending arm 2036, with a downwardly depending arm 2038 at the end of the forwardly extending arm 2036. At the bottom of the forwardly extending arm are grippers 2040.

Because of the extension arm 2034, the grippers 2040 can reach sectors 300 on top of the workbench 100. Moreover, in a "rest" position, the robotic arm 2002A of the first analyzer 2000A is out of the way with regard to the top 2018 of the base 2012 and the front work area of the pedestal, and thereby does not interfere with processing and operator access to the analyzers.

As further shown in FIGS. 15A–15F the grippers 2040 of each analyzer robotic arm 2002 are supported from a gripper actuator 2041, the actuator 2041 being mounted on a bracket 2042 that is rigidly attached to an elevator member 2043 of the robotic arm 2002. A crank member 2044 is movable about a vertical axis 2045 of the actuator 2041 between first and second positions through an angle of approximately 180° for selective opposite orientational placement and recovery of sectors 300 at the analyzer transfer site 2004 and at the workstation delivery site 106. A robotic clamp 2046 is mounted to an end extremity of the crank member 2044 for movably supporting an outwardly facing pair of hook-shaped gripper members 2048, each of the gripper members 2048 being insertable through a respective top wall slot 322 of the sector 300, the sectors 300 being described below in connection with FIGS. 8A–8C. After such insertion, hook-shaped end extremities 2049 of the gripper members 2048 engage the underside of a top wall 306 (having the slots 322 formed therein) upon activation of the clamp 2046 for separating the gripper members 2048. Also, each gripper member 2046 has an extractor member 2050 vertically slidably engaged therewith, a vertically oriented compression spring 2052 being interposed above the extractor member for biasingly contacting the top wall 306 between the slots 322 when the gripper members 2048 extend into the slots 322. One purpose of the extractor members 2050 is for insuring that the sector 300 remains in place undisturbed when being deposited at a site, the extractors holding the sector down during withdrawal of the gripper members 2048 during raising of the elevator member 2043. Another purpose of the extractor members 2050 is for stabilizing the sector 300 on the gripper members 2048 during manipulation by the analyzer gripper 2040.

A device suitable for the actuator 2042 is available as Model NCRB/BW30-180S rotary actuator, from SMC of Tustin, Calif. A device suitable for use as the robotic clamp 2046 is Model HGP-10-A gripper, available from Festo, of Hauppauge, N.Y. Devices suitable for use as the analyzer track 2028 and drive 2030 are available as Model IS-MX-20-200-400 robotic positioning system with Model SA-A vertical moving feature, from Intelligent Actuator of Torrance, Calif.

With further reference to FIG. 13G, a preferred alternative configuration of the gripper members 2048 for use with the sectors 300' includes one gripper member, designated 2048', for engaging the resilient block 334, and a complementary gripper member, designated 2048", for clamping against the back wall 305 of the sector 300'.

Workstation

A layout of a preferred workstation 100 or bench is shown in FIG. 4. This layout is particularly adapted for having the centrifuge 1000 on the right side of the workstation 100 as shown in FIGS. 1 and 4. On the input section 116 of the table 112, there are provided fifteen sort sites 128 labeled from left to right, as A–O, for sectors 300, and corresponding fifteen sort sites 130 A–O for racks for holding test tubes. The track 704 for the robotic arm 700 extends down the middle of the table, extending from end to end, dividing up the table into the input sections 116 and the analyzer section 118. The racks are closer to the track 704 than are the sectors, because there is more travel of the robotic arm associated with the racks, where the containers need to be loaded and unloaded one by one.

In a typical assignment of the sector and rack sites, the input locations 16 include rack sites 128 and sector sites 130 labeled A–J, where new containers to be processed are located (including the priority region 18 at site A, for "STAT" specimens); the output locations 17 include sites N and O, where sectors and racks having completed processing and awaiting removal from the workstation 100 are located; and the auxiliary region 19 include sites K–M, where sectors and racks having specimens ready for analysis are located, such as for a first analysis by one of the analyzers, or for specimens having already been analyzed by one analyzer and are ready for a second analysis process on a second analyzer. It will be understood that the particular division of functions for the locations on the input section 116 can vary depending on the throughput rates of the analyzers, the number of analyzers available, and other factors, and the assignments can differ as between the rack sites 128 and the sector sites 130.

The racks 600, which can be provided with a bar code identification 601, are used for storing and/or sorting test tubes, and as a way of removing and placing large quantities of test tubes on the workstation. The sectors 300, although having smaller capacity, can be picked up by the robotic arms 700 and 2002, being used not only for processing but also for sorting multiple test tubes simultaneously, thereby adding to the efficiency of the workstation 100.

The workbench of FIG. 4 is adapted for use with at least two analyzers. Thus, a "launch pad" 105 at each end of the analyzer section 118 has the delivery site 106 for pickup of sectors by the analyzer robotic arm 2002, and the receiving site 110 for delivery of sectors containing analyzed samples from the robotic arm 2002. Surrounding the launch pads are a plurality of sector locations 134 being used for empty sectors, or for locating loaded sectors at peak processing times when the input section is full.

In the middle of the analyzer side are buckets or receptacles 1200, and a scale 802 and an auxiliary rack site 804 of the balance system 800. FIG. 4 shows four buckets or receptacles 1200 on the scale 802 for balancing, the auxiliary site 804 having a rack 600 for dummy test tubes 806 that are used for balancing out the weight of the loaded buckets. To the right of the auxiliary rack site 804 is the decapping system 900, followed by four buckets 1200 either being unloaded after centrifuging, or being loaded with new test tubes for centrifuging.

With further reference to FIGS. 20A and 20B, a preferred configuration of the table 112 includes a base 20 having a parallel-spaced pair of beam members 22 that connect a spaced plurality of bulkheads 24, the bulkheads 24 having respective column portions 25 that support a rail member 26 of the track 704. Each of the bulkheads 24 also anchors a pair of column members 28 on the beam members 22 the input and analyzer sections 116 and 118 of the table 114 being separately fastened on top of respective rows of the column members 28. By this construction, the table 112 can be conveniently stored and transported as one compact package including the beam members 22, the rail member 26, and the sections 116 and 118, and another compact package including the bulkheads 24 having the column members 28 fastened thereto. There are five of the bulkheads 24, the spaces therebetween defining four bays for accommodating various power distribution and electronic components of the system 10 in a conventional manner. Under each end bulkhead 24 is mounted a pair of swivel casters 130 for rollably supporting the workstation 100, and an adjustable foot assembly 132 is spaced inwardly from each end and mounted under each beam member 22 for leveling and anchoring the table 112 in a conventional manner.

A typical workstation has a length of about 2.83 meters, and an overall width of about 980 mm, with the input section being about 540 mm wide, a track width of about 145 mm, and the analytical section being about 440 mm side.

As further shown in FIG. 1, the workstation 100 is preferably provided with a protective shield system 40 for blocking operator intrusion within space above the table top 114. The shield system 40 has a frame 42 on which are mounted a plurality of transparent panel members 44, being vertically oriented proximate the perimeter of the table top 114, the shield system 40 being interrupted along the rear section 118 for clearing the respective analyzer robotic arms 2002A and 2002B. The panel member proximate the centrifuge unit 1000, designated 44A, has a bubble extension 46 formed therein for inclusion of a path to the centrifuge unit 1000 within the shield system 40. Also, and with further reference to FIG. 21, the panel member along the front section 116, designated 44B, extends down only partway from the top of the frame 42, three transparent door panels 48 being supported for vertical movement in overlapping relation with respective portions of the panel 44B. Each of the door panels 48 is coupled to a piston rod 50 of a pneumatic actuator 52 by a handle clamp assembly 54, the actuator 52 being mounted to a top portion of the frame 42. A solenoid latch 56 is located within the table 114 in association with each door panel 48 for locking same in a closed position thereof. In an exemplary configuration as shown in FIG. 21, the solenoid latches 56 when deactivated engage discontinuities or slots 58 that are formed in lower extremities of the piston rods 50; activation of the latches 56 releases the rods 50. The door panels 48 are reinforced against excessive inward force by the handle clamp assemblies 54 having depending projections 60 thereon that extend proximately against an edge extremity of the table top 114 in the closed positions of the panels 48. A door button 62 is located under each handle clamp assembly 54 for signaling an associated door open request to the process controller 500. Subject to appropriate interlocks and process suspension, the corresponding latch 58 is activated, followed by activation of the corresponding pneumatic actuator 52, whereupon the door panel 48 is raised for operator access to the input section 116 of the workstation 100. The workstation 100 is preferably provided with two emergency stops 64, one proximate each end of the input section 116, for use by an operator.

With reference to FIG. 5, there are provided two sector registration posts or pins 142 for each sector 300. Similarly, two rack positioning pins 146 are provided for locating each rack 600 that is on the workstation 100. A table magnet 145 is mounted flush with the table top 114 in predetermined relationship with pairs of the pins 142 and 146 for attracting respective holder magnets 330 of the sectors 300 and the racks 600 as further described below. Also, there are two bucket locator pins 144 on the workstation 100 for each receptacle or bucket 1200 used for the centrifuge. FIGS. 6A–6C show a typical sector pin 142, rack pin 146, and bucket pin 144, respectively. The particular shape of the pins is selected so they cooperate with the respective devices they serve to locate. As shown in these figures, the three types of pins are different, to inhibit operators from mislocating the devices on the workstation. As further shown in FIGS. 6A–6C, the pins 142, 144, and 146 on the table 114 are located in shallow wells 156 for confining any inadvertent spillage from the containers 12. Counterparts of the wells 156 are also provided on the scale 802. Further, a perimeter trough 158 is formed in each of the front and rear sections 116 and 118 of the table 114 and surrounding the various sites for the holders 14, as shown in FIG. 6A.

The cooperation between the sector pin 142 and a sector 300 is shown in FIG. 8A; the cooperation between the rack a 600 and the rack locating pins 144 is shown in FIGS. 9A and 9B, and the relationship between a centrifuge bucket 1200 and the bucket location pins 146 is shown in FIG. 10C, which shows the pins 146 in an alternative configuration of the centrifuge 1000.

The workstation is provided with a detection system for detecting the presence of sectors and racks on the workstation. In a preferred version of the invention shown in FIG. 7, there is used a sensor or reed switch 150, which is recessed slightly below the top surface of the workstation. Each reed switch 150 is retained by a flush-fitting plug member 152 that is removable for facilitating servicing and/or replacement of the reed switch 150. Preferably, electrical circuits of the reed switches 150 are provided with suitable connectors (not shown) for facilitating replacement of the switches 150 without requiring access below the table top 114. The locations of the reed switches 150 are shown in FIG. 5. The reed switches can be activated by providing the sectors, racks, and buckets with magnets strong enough to activate the reed switch. Also, other detection systems can be used, including weight systems where the detector detects the presence of a sector or the like by its weight; or a detector system that relies on an electrical current, where the presence of a sector or rack closes a circuit so electrical current can be detected; or an optical interrupter, where the device interrupts a light path.

An exemplary sector 300 as shown in FIGS. 8A, 8B, and 8C includes a base 301 having a convex front wall 302, a concave back wall 304, a bottom wall 308, and side walls 310. A top 315 snap fits onto the base 301 and includes a a top wall 306 that extends rearwardly and outwardly from portions of the side walls 310 of the base (the side walls 310 being staggered for clearing the sector positioning pins 142 of the workstation 100, thereby forming an overhang 318, which has two holes 320 therein for the pins 142. Along the front wall 302 are tubular cavities 314 for test tubes 102, and in the version shown in the figures, there are seven such cavities. They extend from the top wall 306 and can drain through the bottom wall 308. Each cavity 314 has a slot 316 in the front so that a bar code reader can read the bar codes 104 on the front of the test tube 102. In the top wall 306 are two slots 322 which can be engaged by the gripper members or jaws 2048 of the analyzer robotic arm 2002 (FIGS. 15A–15F). The slots 316 extend partially in the base 301 and partially in the top 315.

Extending upwardly from the top wall 306 of the sector 300 is a counterpart of the back wall, designated 305, from which projects a T-shaped handle 324, the combination of the back wall 305 and the handle 324 being engageable by the gripper element 726 of the workstation robotic arm 700 (FIG. 13C).

The front wall 302 of the sector 300 is provided with a bar code 326 to identify, and allow the central controller 500 to track the sector and the test tubes therein. The base 301 is also provided with an internal bar code strip 327 which is visible when a test tube slot 316 is empty, but blocked when a test tube is in the slot. Thus a bar code scanner 724 (FIG. 13A) can signal the central processor 500 with the number and location of test tubes in each sector. A holder magnet 330 is mounted flush with the bottom wall 308 for stabilizing the sector 300 and holding the sector in place on the workstation 100 during removal of test tubes 102. The holder magnet 330 is located and oriented for attraction by respective ones of the table magnets 145 of the workstation 100. A sensor magnet 332 is likewise mounted flush with the bottom wall 308, for activation of respective reed switch sensors 150 of the workstation 100.

With further reference to FIG. 8D, an alternative and preferred configuration of the sector, designated 300', has the back wall 305 (and the handle 324) extended somewhat from the top wall 306 and having a rearwardly projecting lip portion 305', a triangularly shaped resilient block 334 being retained on the handle 324 proximately against the underside of the lip portion 305'. The resilient block 334 advantageously facilitates reliable engagement of the sector 300' by the gripper members 2048' and 2048" of the analyser robotic arms 2002 in the configuration of FIG. 13G, by permitting increased vertical (and horizontal) alignment tolerance as compared with the engagement configuration of FIG. 15E. The resilient block 334 also facilitates more effective gripping by the gripper members 726 of the workstation robotic arm 700 in the configuration of FIG. 13D, by resilient conformity of the block 334 with one of the gripper members 726, and by the combination of the block 334 and the back wall 305 having a non-circularly cylindrical shape, the engagement producing a centered and vertically aligned relationship between the sector 300' and the gripper axis 715 regardless of slight variations in vertical positioning of the gripper members.

Because laboratories typically process specimens from different sources, such as different hospitals, testing labs, and doctors' offices, the containers or test tubes 102 often have different diameters and different heights. To accommodate variations in diameters, the top 315 has four depending fingers 328 for each test tube slot 314, the fingers being biased radially inwardly. The sector 300' shown in the FIG. 8D is available from Beckman Instruments with the Synchron CX machine.

With reference to FIGS. 9A–9D, a test tube rack 600 suitable for use in the system 10 includes a frame 602 having the bar code identifier 601 applied thereto, and defining a 5 by 10 array of vertical cavities 603. The frame includes holes 604 for the positioning pins 146, and has counterparts of the holder and sensor magnets 330 and 332. Each of the cavities 603 is provided with an insert member 606 having spring fingers 607 to hold different size test tubes in the rack, the fingers being formed for retaining a resilient O-ring member 609 that augments frictional engagement of containers 12 being test tubes 102 by the fingers 607. Thus each rack 600 forms a holder 14 for the containers 12, the cavities 603 being typically spaced at a pitch of approximately 20 mm, the inserts 606 being sized for biasingly centering the containers 12 up to approximately 16 mm in diameter, the combination of the finger members 607 and the O-ring 609 being sufficiently resilient for effectively centering containers not larger than approximately 13 mm in diameter.

Although the present invention is described with regard to bar code and bar code readers for tracking test tubes and other components of the system, other detection systems can be used. For example, magnetic ink labels can be placed on test tubes and other components, to be read by a magnetic ink reader.

With reference to FIGS. 10A, 10B and 10C, the buckets or receptacles 1200 each have an array of cavities 1203 corresponding to the openings 603 of the racks 600, the cavities 1203 symmetrically surrounding a stem member 1204. An upper portion of the stem member 1204 is square in cross-section for engagement by the gripper members 726 (FIG. 13C) of the robotic arm 700 in any of four discrete orthogonal orientations, a spaced pair of resilient O-rings 1206 being retained on the stem member for augmenting frictional engagement by the gripper members 726. As shown in FIG. 10A, there are 16 of the cavities 1203 in each receptacle 1200, each cavity 1203 being defined by a counterpart of the insert 606 and having counterparts of the finger members 607. The receptacles 1200 are adapted for placement in respective cradles 1008 of the centrifuge unit 1000, having a pair of notches 1208 formed in opposite sides thereof for registration with respective bearing caps 1009 of each cradle 1008 as shown in FIG. 10A.

As shown in FIG. 10C, each receptacle 1200 is formed with a pair of holes 1210 for registration on corresponding bucket positioning pins 144, and a counterpart of the sensor magnet 330 for activation of the associated reed switch sensor 150 of the workstation table 114 (FIG. 5). Optionally and a further shown in FIG. 10C, a counterpart of the sensor 150 can be located in or under the cradle 1008 for sensing a seated condition of the receptacle 1200 in the centrifuge head 1006, and/or counterparts of the positioning pins 144 can be mounted on the cradle 1008 as an alternative to registration of the receptacle 1200 by the bearing caps 1009.

When loading buckets with test tubes for use in the centrifuge, it is important they be loaded in a systematic way to provide balance. FIGS. 11A–11D provide a top plan view of receptacles 1200 loaded into the centrifuge, showing satisfactory loading patterns. Empty test tube cavities 1203 are represented by unfilled circles, blackened circles representing cavities loaded with test tubes 102. The buckets are loaded to provide even weight on opposite sides of the center point of the centrifuge, as well as maintain each receptacle approximately balanced relative to the respective stem member 1004. Other suitable loading patterns are known to those of ordinary skill in the art.

With particular reference to FIGS. 13A, 13B, and 13C, an exemplary configuration of the robotic arm 700 includes a base carriage 702 that is positionable along the workstation track 704. The track 704 extends proximately between opposite ends of the workstation 600 approximately centered between opposite sides thereof, and having protective accordion covers 705. A panning head 706 is controllably rotatably supported on a vertical pan axis 707 of the base carriage 702, an upper arm 708 being likewise controllably rotatably supported on a horizontal shoulder axis 709 of the panning head 706. A lower arm 710 is likewise controllably rotatably supported on an elbow axis 711 of the upper arm 708, the elbow axis 711 being parallel-spaced from the shoulder axis 709 at an outer extremity of the upper arm 708. Similarly, a wrist head 712 is controllably rotatably supported on a wrist axis 713 of the lower arm 710, and having a gripper head 714 controllably rotatably supported therefrom on a gripper axis 715. The axes 713 and 715 are orthogonal, the wrist axis 713 being parallel-spaced from the elbow axis 711 at an outer extremity of the lower arm 710. The gripper head 714 has a gripper body 716, pair of gripper armatures 717 being controllably movable with tactile feedback toward and away from opposite sides of the gripper axis 715. The gripper head 714 also includes an optical head sensor 718 fixably supported relative to the gripper body 716, the head sensor 718 including a light source 719 having a source axis 720, and a light portion 721 having a receiver axis 722, the axes 720 and 722 converging proximate the gripper axis 715 from opposite sides thereof in spaced relation to the gripper body 716 and the gripper armatures 717. The robotic arm 700 also includes a robot control system (not shown) having suitable provisions for manipulating the gripper head 714 relative to the workstation track 704 for grasping and transporting objects in a manner known to those having skill in robotics. As so far described, the exemplary robotic arm 700 is a commercial device, available as Model 255 from CRS Robotics of Ontario, Canada.

As further shown in the drawings, the robotic arm 700 is provided with an indicia scanner 724, sometimes referred to herein as bar-code scanner 724, the scanner 724 having a scan axis 725 and being fixedly located on the upper arm 708 such that the scan axis normally intersects the gripper axis 715 distally from the intersection of the source and receiver axes 720 and 722. Thus the scanner 724 is advantageously oriented on the upper arm 708 for permitting effective scanning of both vertically and horizontally oriented indicia. Particularly, the container indicia 104 are normally vertically oriented, while the various indicia of the racks 600, receptacles 1200, and sectors 300 are normally horizontally oriented. Moreover, the gripper head 714 is provided with a pair of gripper members 726, the gripper members 726 being mountable on respective ones of the gripper armatures and being adapted for grasping containers, receptacles, and sectors as described herein, for transport thereof. Further, the head sensor 718, in combination with programmed movement of the gripper head 714, permits determinations of the heights of the containers 12 for effective engagement by the gripper members 726.

As further shown in FIG. 13B, the robotic arm 700 is movable about the pan axis 707 within an angle e that is symmetrical on opposite sides of the workstation track 704 and greater than 180°, being approximately 315°. This range of angular orientations about the pan axis 707, in combination with the base carriage being movable to proximate each end of the workstation 600, facilitates transport of containers 12, sectors 300, and other holders to virtually any location within the table 114, often without requiring movement of the base carriage 702 along the workstation track 704. Also, the gripper head 714 is advantageously locatable in overhanging relation to the table panel 114 for accessing the centrifuge unit 1000.

With further reference to FIG. 13D, an alternative configuration of the gripper head 714 has the head sensor 718 on one side only of the gripper body 716, a laser source 719' being substituted for the emitter 719 and mounted adjacent the light receiver 721. Thus the source and receiver axes 720 and 722 converge from the same side of the gripper axis 715; however, the laser source 719' more than compensates for any loss of effectiveness of the sensor 718 that would be attributable to the axes 720 and 722 being asymmetrical relative to the gripper axis 715.

Site Adjusters

The workstation delivery site 106 and receiving site preferably are provided with a site adjustment mechanism 961 for each of the analyzers 2000, each adjustment mechanism 961 facilitating exchanges of holders 300 between the workstation 100 and the corresponding analyzer 1200. As shown in FIGS. 12A and 12B, the delivery site adjuster 961 includes a platform member 962 and a clamp member 964 that are movably coupled on opposite sides of the table panel 112 of the workstation 100 by a plurality of threaded fasteners 965, the fasteners 965 and a boss portion 966 of the platform member 962 extending through a clearance opening 967 that is formed in the table 112. Each of the fasteners 965 carries a compression spring 968 for biasing the platform member 962 and the clamp member 964 into clamping engagement with the table panel 112, the platform member 962 also having an O-ring 969 partially recessed therein for frictionally gripping the table during the clamping. A pneumatic cylinder 970 is coupled between the clamp member 964 and the boss portion 966 of the platform member 962 for releasing the clamping in response to selective application of pressurized gas to a gas port 971 of the pneumatic cylinder 970 by a gas pressure system 850 (FIG. 19). Thus the platform member 962 is freely rotatable and laterally translatable while the pneumatic cylinder 970 is activated. The platform member 962 has two pairs of the locating pins 142 mounted thereon for locating and holding corresponding sectors 300 thereon, the sectors 300 being accessible by either the workstation robotic arm 700 or the corresponding analyzer robotic arm 2002. Also, the platform member 962 has sensors 150 imbedded therein for sensing corresponding sectors 300 being registered on the associated pair of pins 142, each sensor 150 being typically implemented as a conventional magnetic reed switch and coupled for signalling with the process controller 500.

Once each analyzer 2000 is set up in proximate alignment with the workstation 100, the associated alignment mechanism 961 is adjusted by first activating the pneumatic cylinder 970 for releasing the clamping, then manually positioning and orienting the platform member 962 for alignment of the sectors 300 with the analyzer gripper 2040 in corresponding workstation transfer positions of the analyzer robotic arm 2002. The pneumatic cylinder 970 is then released for clamping the platform member 962 in the aligned position, thereby effecting the adjustment. Finally, the position and orientation of the platform plate 962 is stored in memory of the process controller 500 by any suitable means, such as by scanning the sectors 300 in seated positions thereof on the platform member 962 using the optical head sensor 718 of the workstation robotic arm 700.

Balance System

As indicated above, and with particular reference to FIGS. 4, 17A, and 17B, the processing system 10 includes a balance system 800 for balancing containers 12 in receptacles or buckets 1200 prior to centrifugation, the balance system including the scale 802 and the auxiliary rack site 804 on the rear section 118 of the workstation 100. The scale 802 can be a conventional electronic platform scale to which is added counterparts of the bucket positioning pins 144 for locating the receptacles 1200. Buckets are moved between the scale 802, the centrifuge unit 1000, and other locations on the rear section 118 by the workstation robotic arm 700, which also transfers containers 12 to buckets 1200 on the scale 802 from a rack 600 at the auxiliary site 804 as well as from other locations on the workstation 100. The balance system 800 also includes a balance controller for selectively depositing containers in cavities of the receptacles while correlating incremental weight changes with the locations of each deposit for equalizing weight in pairs of the receptacles. The balance controller can be implemented as a balance program 808 within the central process controller 500, the balance program 808 maintaining a database 810 of container locations and associated weights, and directing the robotic arm 700 for depositing the containers 12 into the receptacles 1200 in response to weights measured by the scale platform 802, the weights being signaled in any suitable manner to the process controller 500.

Preferably the balance system also includes a supply of dummy loads 806 (which can be test tubes 102 that are loaded with predetermined weights) to be selectively deposited into the receptacles 1200. Accordingly, the balance controller is operative for moving dummy loads 806 to appropriate locations in particular receptacles 1200 for limiting weight variations between receptacles. Preferably the dummy loads 806 are progressively weighted for limiting the weight variations in pairs of the receptacles 1200 to not greater than 10 grams. The auxiliary rack site 804 is provided on the workstation 100 proximate the scale 802 for facilitating temporary storage of the dummy loads 806, the rack 600 at the site 804 also providing additional temporary storage for containers 12 to be further processed and/or sorted.

In the balance program 808, the scale database 810 is initially loaded in a select specimens step 812 with counterparts of container indicia 104, and with data for a common spin cycle 1002 associated therewith, the corresponding containers 12 being in a quantity appropriate for simultaneous centrifugation by the centrifuge unit 1000. Next, in a tare step 814, an appropriate complement of receptacles 1200 for holding the containers 12 is identified, and seated if necessary, at respective sites on the scale platform 802. A total load on the scale 802 is measured fallowing the depositing of each item on the scale 802, a difference between successive measurements representing each particular added load. Following the tare step 814 is a load step 816, wherein the containers 12 to be centrifuged are sequentially placed in respective ones of the receptacles 1200 according to an appropriate one of the patterns of FIGS. 11A–11D, depending on the number of the containers 12 to be centrifuged. The balance program 808 continues monitoring the loads added to the scale 802 during the load step 816. Thus the balance program 808 is operative for monitoring the total weight associated with each of the receptacles 1200. After the load step 818, appropriate ones of the dummy loads 806 are added in a correction step 820 as required to bring members of each pair of the receptacles 1200 to within the predetermined allowable variation.

Decapper System

With particular reference to FIGS. 18A and 18B, the decapper system 900 includes a receiver 902 for clampingly holding a container or test tube 102 having a cap 103 frictionally engaging the test tube 102 and extending laterally from opposite sides of a top portion of the test tube 102. The receiver 902 is mounted in depending relation to a decapper deck insert 903 of the workstation 100 as further described below. An important aspect of the present invention is that the decapper system 900 is operative with both threadingly engaged caps as described below, and with caps having frictional engagement only with the container 12 as described herein. A yoke member 904 having a cap slot 905 formed therein is movably mounted on an elevator 906 that projects above the deck insert 903, being supported thereby. The elevator 906 includes an actuator 908 and an elevator column 909 that is rigidly connected to the yoke member, the actuator 908 being coupled to a translation motor 910 through a translation belt 911 for rotational translation of the yoke member 104 concentric with the elevator column 909 between open and closed positions thereof. The elevator 906 is also coupled to an elevator motor 912 through an elevator belt 913 for raising and lowering the elevator column together with the yoke member 904. The yoke member 904 has an upwardly facing ledge portion 916 formed within the cap slot 905 for engaging the underside of an outwardly extending shoulder surface 917 of the cap 103 when the cap 103 is seated in the test tube 102, the tube 102 being held in the receiver 902, in the closed position of the yoke member 904.

With the ledge portion 916 extending under the shoulder surface 917 in the closed position of the yoke member 904, the elevator 906 is operative for raising the yoke member 904 relative to the receiver 902 to thereby remove the cap 103. The receiver 902 includes a bladder cage 920 for rigidly supporting a bladder 921, the bladder 921 having a gas port 922 for selective inflation from a suitable pressure source, described below, thereby to grip a test tube 102 being seated therein. Thus the receiver 902 is operative for holding the container 12 against axial forces exerted by the yoke member 904 as the cap 103 is being pulled from the container 12.

As mentioned above, a further important capability of the decapper system 900 is removal of threadingly engaged caps 103. Accordingly, the bladder cage 920 is rotatably mounted to the deck insert 903, being coupled to a rotation motor 924 through a rotation belt 925 for controllably turning the bladder 921 concentrically with the container 102, thereby to unscrew the container 12 from the cap 103. The cap 103 is prevented from rotation within the yoke member 904, being formed with a non-circular outer contour having an enlargement 927 formed thereon, the enlargement 927 of the cap 103 bearing against a portion of the cap slot 905 when torque is applied to the container 12 by the retainer 902. The gas port 922 is preferably configured to provide a rotary connection to the bladder 921, the port 922 being connected to a three-way control valve 928 through a cage line 929 for selective pressure activation in response to the central controller 500 to effect the above-described holding of the containers 12.

With further reference to FIG. 18F, a preferred alternative of the bladder cage, designated clamp cage 920', includes a resilient sleeve 921' in place of the bladder 921, the sleeve 921' having three outwardly projecting ears 926 that engage respective ear slots 929 of the cage 920' to insure rotational integrity of the sleeve 921' with the cage 920'. Three vertically oriented jaws 913 are spaced between the ears 926 together with corresponding cam bars 914, the bars 914 resting on a disk plate 915. An air cylinder 918 that is coupled by the fitting 922 to the control valve 928 through the cage line 929 drives the disk plate 915 and the bars 914 upwardly. The bars 914 have a spaced pair of cam slots 914A that engage corresponding pins 914A that project from the jaws 913, thereby driving the jaws 913 inwardly in response to the upward movement of the bars 914 for compressing the sleeve 921' against the test tube 102. The sleeve 921' is dosed at the bottom for confining debris in case a test tube 102 is fractured therein. Also, the sleeve 921' has ribs 923 formed therein for contacting the test tube 102, including three full-length clamp ribs 923A that are aligned with the jaws 913 and three foreshortened holder ribs 923B. Spaces between the ribs 923 contribute flexibility to the sleeve 921' for enhanced effectiveness of the jaws 913 in gripping the test tubes 102. Test tubes 102 that are 100 mm in length normally extend to proximate the bottom of the sleeve 921', while test tubes 102 having a length of 75 mm are normally inserted only partway into the sleeve 921' as indicated by broken lines in FIG. 18F, the holder ribs 923B being configured for retention of the shorter test tubes 102 partially inserted, without adding unnecessarily to the axial forces required for full insertion and withdrawal of the 100 mm test tubes 102.

Preferably the decapper system also includes a collector 930 for receiving caps 103 from the yoke member, and an unloader 932 for transferring removed caps from the yoke member 904 to the collector 930. An exemplary implementation of the unloader includes an upstanding unloader post 934 fixedly mounted to the deck insert 903 proximate the collector 930, in alignment with the cap slot 905 in the open position of the yoke member. A decapper program portion of the central controller 500 is operative for moving the yoke member 904, having a removed cap 103 therein, until the post 934 strips the cap 103 from the yoke member. Preferably, the collector 930 further includes a tube member 936 for directing the stripped caps 103 into the collector 930.

With further reference to FIGS. 18C–18E, an alternative and preferred configuration of the decapper system, designated 900', includes a yoke housing 938 having a bottom cover 939 as a counterpart of the yoke member 904, a clamp mechanism 940 being operative within the housing 938 for positively gripping the caps 103. As shown in FIG. 18E, the clamp mechanism 940 has an opposed pair of pivotally mounted jaws 942 that are operated by a pneumatic cylinder 944 having a wedge-shaped cam actuator 946 that extends from the cylinder 944 in response to applied gas pressure. The jaws 942 are each formed having a plurality of projections 943 therein for gripping opposite sides of the caps 103 when same are positioned within the cap slot 905. The yoke housing 938 is formed having a passage 948 therein from the cylinder 944 to a fitting 949 that projects below the cover 939 for connecting a flexible line 950, the line 950 extending below the deck insert 903 to a three-way valve 952. The valve 952, being connected by a decapper line 870 to the pneumatic system 850 (FIG. 19) as is the valve 928 described above, is operative for activating the pneumatic cylinder 944 in response to the central controller 500 to effect gripping of the caps 103. Thus the caps 103 are not required to have enlargements 927 or to otherwise have a rotationally interfering fit with the cap slot 905. Further, the caps 103 are not required to have the outwardly projecting shoulder surface 917 (FIG. 18A) in the preferred decapper 900'.

As further shown in FIGS. 18C and 18D, the decapper system 900' includes a counterpart of the unloader 932 on the yoke housing 938, in the form of a plunger assembly 954. The plunger assembly 954 includes a shouldered plunger 955 that is guided within an ejector support 956, the plunger 955 having an upwardly projecting stem 957 that slidingly engages the support 956, an ejector spring 958 being interposed on the stem 957 for downwardly biasing the plunger 955 against the yoke housing 938. A cap 103 being released from the jaws 942 by deactivation of the valve 952 is forcefully extracted from the cap slot 905 by axial movement of the plunger 955 into engagement with the yoke housing 948. Thus caps 103 are prevented from sticking to the projections 943 of the jaws 942 when the clamp mechanism 940 is opened, for reliable unloading into the collector 930.

The controller 500 is programmed for driving the elevator 906 sufficiently high for the plunger 955 to clear the cap 103 as the cap slot 905 is rotated into position over the cap 103, then lowering the yoke housing 938, thereby compressing the ejector spring 958 as the jaws 942 are lowered into a desired alignment with the cap 103, the cap 103 supporting the plunger 955. Next, the clamp mechanism 940 is closed by activation of the valve 952, the jaws 942 gripping the cap 103, and operation of the decapper 900' continues as described above in connection with the decapper system 900 of FIGS. 18A and 18B.

As further shown in FIG. 18B, the tube member 936 is provided with a cap detector 959 for signaling the controller 500 upon each passage of a cap 103 into the collector 930. Thus appropriate corrective action can be taken in the event that processing a capped container 12 by the decapper system 900' fails to result in detected passage of the cap 103 into the collector 930.

As shown in FIG. 19, the workstation 100 is provided with a pneumatic circuit or gas pressure system 850 having a plug connection 851 to a suitable source 852 of pressurized gas, the gas being fed through an inlet filter 853 to an accumulator reservoir 854 of approximately 22 liters capacity, a one-way inlet valve 855 being provided for maintaining pressure when the source 852 is inactive. A main solenoid valve 858 and a pressure transducer 859 are series-connected between the inlet filter 853 and the inlet valve 855, the transducer 859 signaling the normal presence of gas pressure at approximately 5 atmospheres. The rail 26 of the track 704 is utilized as the reservoir 854, the rail 26 advantageously providing large capacity and extending substantially the full length of the workstation 100 for enabling relatively short pneumatic connections.

A distribution manifold 860 is connected to the reservoir 854 for feeding pneumatic elements of the workstation 100 as described herein. In a bearing branch 861 from the manifold conduit 860, a moisture filter 862, a pressure regulator 863 having an oil filter 864 and a pressure indicator 865, and a pressure transducer 866 are series-connected for feeding air bearings of the track 704 of the workstation robot arm 700, the transducer 866 signaling a normal pressure of approximately 4.5 atmospheres. A brake branch 867 from the manifold 860 has a solenoid brake valve 868 connected therein for activating a track brake of the track 704. A counterpart of the pressure regulator, designated 869, is connected in a decapper branch 870 from the manifold conduit 860 for feeding the decapper system 900. A shield branch 871 from the manifold 860 having another regulator, designated 872, feeds a trio of door valves 873 for controlling the pneumatic actuators 52 of the shield system 40. A pair of adjuster valves 874 being mounted to the rail 26 of the track 704 for fluid connection to the reservoir 854 for selectively releasing the delivery site adjusters 961, the valves 874 being connected by respective adjuster lines 875 to corresponding gas ports 971 of the adjusters 961. Finally, a pair of side loader branches 876 of the manifold conduit 960 have corresponding counterparts of the valves 874, designated manually activated valves 878, therein for feeding pneumatic components of the analyzers 2000, including the analyzer robotic arms 2002.

Centrifuge Unit

As described above, the centrifuge unit 1000 receives the specimens in containers 120 that have been loaded into receptacles 1200, subjecting the specimens to a specified spin cycle 1002 prior to further processing in the analyzer 2000. With particular reference to FIG. 16A, the centrifuge unit 1000 provides a plurality of load stations 1004 on respective cradles 1008 of a rotatably driven spindle head 1006 for receiving a balanced complement of the receptacles 1200 within a spin chamber 1010 of the centrifuge unit 1000. As used herein, "receptacle" includes buckets 1200, but broadly means a device for holding a fluid specimen within a centrifuge and during transport of the specimen into and out of the centrifuge. Thus "receptacle" can stand for (1) a single test tube, vial or other container when the container is loadable directly into a centrifuge head cavity; or (2) a rack, sector, or other holder for one or more containers when the containers are in such holders during centrifugation.

An exemplary embodiment of the centrifuge unit 1000 includes a cabinet 1012 having a chamber opening 1014 for accessing the spin chamber 1010, a spindle unit 1016 being supported within the cabinet 1012 under the opening 1014 for driving the spindle head 1006, the cradles 1008 being pivotally mounted to the spindle head 1006 as indicated by pairs of bearing caps 1009. The cabinet 1012 includes a wheeled base frame 1018 having a base plate 1020 fastened thereon, a plurality of body panels including respective pairs of side panels 1022 and end panels 1024 surrounding the frame 1018 and extending upwardly from the base plate 1020, and a deck panel 1026, the deck panel 1026 extending between upper extremities of the body panels 1024 and 1026. A chamber bezel 1028 having the chamber opening 1014 formed therein covers a portion of the deck panel 1026, an access panel 1030 also covering a portion of the deck panel 1026, the deck panel 1026 having an opening (not shown) that corresponds to the chamber opening 1014, and another opening (not shown) under the access panel 1030 for service access to interior portions of the cabinet 1012.

According to the present invention, the centrifuge unit 1000 includes a horizontally oriented door member 1032 that is laterally movable under the chamber bezel 1028 between an open position as shown by solid lines in FIG. 16A, and a closed position as indicated by dashed lines. The open position of the door member 1032 provides access to the spin chamber 1010, the closed position blocking such access for protecting against accidental contact with the spindle head 1006 and contents thereof during operation of the centrifuge unit 1000. The door member is supported within a door frame 1034, the frame 1034 being rigidly spaced above the base plate 1020 on a plurality of column members 1036. The door member 1032 is driven between the open and closed positions by a frictionally coupled door actuator 1038 as further described below, the actuator 1038 advantageously protecting personnel from being injured in case of inadvertently reaching through the cavity opening 1014 while the door member 1032 is moving to the closed position, by limiting the application of actuating force to the door member 1032. As further shown in FIG. 16A, the centrifuge unit 1000 can include an input keyboard 1040 and a CRT display 1042 for interfacing with an operator of the unit 1000.

With further reference to FIGS. 16B–16E, a preferred alternative configuration of the centrifuge unit 1000 has a smaller counterpart of the cabinet (not shown) with counterparts of the door member, designated 1032', and the door frame, designated 1034', whereby access through the chamber opening 1014 to the spin chamber 1010 is normally through a reduced-size access opening 1044 for facilitating rapid opening and closing of the door member 1032'. As shown in FIG. 16B, the door panel 1032' is supported within a removable door module 1046 between an upper or outer tray member 1048 and a lower or inner tray member 1050, vertically aligned counterparts of the opening 1044 being formed in each of the tray members 1048 and 1050. The access opening 1044 is sufficiently large for passing one of the receptacles 1200 vertically therethrough into seating engagement with one of the load stations 1004 when that load station 1004 is indexed to a loading position as described below. More particularly, the tray members 1048 and 1050 of the door module 1046 are fastened to opposite sides of respective spacers 1052, a handle 1054 being mounted on one of the spacers 1052 for horizontally withdrawing the door module 1046 from the frame 1034', thereby to fully expose the spin chamber 1010 through the chamber opening 1014. It will be understood that access to the door module 1046 can be provided by any suitable means, such as removal of the associated end panel 1024.

As further shown in FIG. 16B, the door frame 1034' includes a support plate 1056 that extends between upper extremities of the column members 1036, a spaced pair of side rails 1058 being rigidly fastened along opposite sides of the support plate 1056 for laterally locating the door module 1046. As shown in FIG. 16C, the door actuator 1038 includes a friction drive wheel 1060 that is rotatably supported by a drive housing 1062, a stepper motor 1064 being coupled thereto. The drive wheel 1060 has a resilient ring member 1066 formed thereon for biasingly contacting an edge surface 1068 of the door member 1032' thereby to translate the door member 1032' between the open and closed positions thereof.

An important feature of the door actuator 1038 is that the drive wheel 1060 is not positively coupled to the door member 1032', making sliding contact therewith in case movement of the door member 1032' is blocked, for example, by laboratory personnel reaching into the spin chamber 1010 as the door member 1032' is being driven toward the closed position. The door member 1032' is movably supported within the door module 1046 by a plurality of guide rollers 1070 that engage a pair of tracks, designated primary track 1072 and secondary track 1073, the tracks 1072 and 1073 being fastened to the inner tray member 1050.

As further shown in FIG. 16C, the door member 1032' is supported both vertically and horizontally relative to the primary track 1072, horizontally oriented ones of the rollers 1070 being mounted by respective threaded fasteners 1070A to the door member 1032', vertically oriented ones of the rollers 1070 being supported on respective rods 1070B that are clamped to the door panel 1032' by corresponding retainer plates 1070C. The housing 1062 is adjustably mounted to the door frame 1034' by suitable fasteners 1074 for providing a desired degree of coupling between the drive wheel 1060 and the edge surface 1068.

As further shown in FIGS. 16B and 16D, a solenoid-operated latch 1076 is mounted to the door frame 1034' for locking the door member 1032' in the closed position thereof, the door member 1032' having an opening 1078 formed therein for engagement by the latch 1076. Also, a slot 1079 is formed in the inner tray member 1050 and one of the spacers 1052 for permitting withdrawal of the door module 1046 when the latch 1076 is retracted from the door member 1032'. It will be understood that the door actuator 38 as described above is suitable for driving the door member 1032 of FIG. 16A as well as the door member 1032' of FIG. 16B, counterparts of the guide rollers 1070 also being suitable for supporting of the door member 1032 of FIG. 16A.

As shown in FIG. 16D, the centrifuge unit 1000 includes a control circuit 1080 for operating the spindle unit 1016, the drive unit 1038, and the latch 1076, a pair of optical position sensors being located relative to the door frame 1034' for signaling the open and closed positions of the door member 1032', a first sensor 1081 signaling the closed position, a second sensor 1082 signaling the open position of the door member 1032'.

The spindle unit 1016 includes the spindle head 1006, a spindle assembly 1084 having a spindle shaft 1085 for rotatably supporting the spindle head 1006 within the spin chamber 1010, the spindle assembly 1084 also having a spindle housing 1086 that is supported from the base plate 1020. A spindle motor 1088 is coupled to the spindle shaft 1085 in a conventional manner, the motor 1088 being fixedly supported relative to the base plate 1020 by any suitable means.

An important feature of the present invention is that the spindle unit 1016 is capable of indexing each of the load stations 1004 into alignment with the access opening 1044 for receipt and delivery of the receptacles 1200, the spindle head 1006 coming directly and rapidly to a halt in a predetermined one of the indexed positions at the conclusion of any desired spin cycle. Accordingly, the spindle motor 1088 is provided with a position encoder 1090 for signaling angular positions of the spindle head 1006. In an exemplary and preferred configuration of the control circuit 1080 shown in FIGS. 16D and 16E, the spindle motor 1088 is a four-pole brushless AC servo motor, a motor of this type being Model SGM-00A3 Servomotor, available from Yaskawa Electric America, Inc., of Northbrook, Ill. The above-identified motor includes the encoder 1090 having a quadrature incremental count output 1091 of 2048 pulses/rev., and an index pulse output 1092. As also shown in FIG. 16D, the control system 1080 also includes a centrifuge processor 1093, a motion processor 1094, and a motor driver 1095, the motion processor 1094 being responsive to the encoder 1090 and position setpoint signals from the centrifuge processor 1093 for feeding acceleration control signals to the motor driver 1095, thereby driving the motor 1088 from an indexed initial rest position to a programmed spin velocity, holding that velocity for a programmed spin duration, then decelerating the motor 1088 to rest at a predetermined final rest position.

Suitable devices for use as the centrifuge processor 1093 are commercially available from a variety of sources, one such being a STD-32 486 CPU Board, available from Ziatech of San Luis Obispo, Calif. A device suitable for use as the motion processor 1094 is available as Model STD/DSP Motion Controller from Motion Engineering, Inc. Of Santa Barbara, Calif. This device processes the quadrature signals of the count output 1091 for feeding a position register with 8192 counts per revolution of the spindle motor 1088, the device also having a destination register that is loaded from the centrifuge processor 1093, and a digital to analog converter (DAC) that generates an analog output as a function of the difference between the position register and the destination register and other variables including maximum velocity and acceleration. It will be understood that the above-identified motor and motor driver would not ordinarily be considered suitable for use as the spindle motor 1088 and the motion processor 1094, in that the rated allowable load inertia is only 0.189 oz-in-sec$^2$ (0.836×10$^{-4}$), being a factor of approximately 250 below what is practically feasible in the centrifuge unit 1000 of the present invention. In accordance with the present invention, it has been discovered that the above-identified motor and motor driver are suitable for use in the centrifuge 1000, with a suitable compensating filter 1096 connected between the motion processor 1094 and the filter 1095. Primarily, the compensating filter 1095 provides a "notch" frequency response, the notch being centered at approximately 75 Hz.

As further shown in FIG. 16D, the control circuit 1080 also includes a stepper motor driver 1098 for operating the stepper motor 1064 of the door actuator 1038 in response to the centrifuge processor 1093. A device suitable for use as the stepper motor driver 1098 is available as Model 48312 Microstepping Driver from Intelligent Motion Systems, Inc. of Taftville Conn. The centrifuge processor 1093 also has a system interface 1099 for communication with the process controller 400. It will be understood that the keyboard 1040 and the display 1042 in the configuration of FIG. 16A have conventional interfaces (not shown) with the centrifuge processor 1093, those components not being required when the processor 1093 is interfaced with the process controller 400. The actual connections among the components of the control circuit 1080 are best shown in FIG. 16E, the circuit 1080 further including a conventional STD-32 cardcage 1100 for the centrifuge processor 1093 and the motion processor 1094, an EMI filter 1102 having means for connection to an external source of electrical power, a main power supply 1104 and a stepper power supply 1106 for the stepper motor controller 1098, the power supplies 1104 and 1106 being powered from the EMI filter 1102, a regeneration unit 1108 for the motor driver 1096, and an I/O board 1110 that provides principal interconnections between components of the control circuit 1080. The regeneration unit 1108 absorbs energy that is recovered from the spindle motor 1088 during deceleration, for limiting unwanted power dissipation by the motor drive 1095. A device suitable for use as the regeneration unit 1108 is available as Model JUSP-RG08 Regenerative unit, from Yaskawa Electric. The I/O board 1110 also incorporates the compensating filter 1096 and conventional buffer circuits for the sensors 1081 and 1082, and for the solenoid latch 1076, as shown in FIG. 16F. More particularly, the compensating filter 1096 includes a twin-T filter 1112, a low-pass operational amplifier 1114, a two-stage low-pass filter 1116, and a buffer amplifier 1118, these elements being series-connected between the previously introduced analog output, designated 1120, of the motion processor 1094 and a torque command input 1122 of the motor driver 1095.

FIG. 16G depicts a control program 1130 of the centrifuge processor 1093, the program 1130 having an initialization procedure 1131 wherein both program and data information is loaded into memory of the motion processor 1094, serial communications are established between the processor 1093 and the stepper motor drive 1098, default variable values are stored in variable memory of the processor 1093, and action flags are reset. The initialization procedure 1031 is followed by a main loop 1132 having a get command step 1133 for receiving commands and data from the process controller 400. In an exemplary implementation of the program 1130, the executable commands are listed in Table 1, below.

TABLE 1

Centrifuge Commands

| Command Code | Command Name |
|---|---|
| IM | Index Move |
| SA | Set Acceleration |
| SV | Set Velocity |
| ST | Set Time |
| BR | Begin Run |
| HD | Home Door |
| HM | Home Motor |
| ER | Stop |
| VS | Get Velocity Status |
| RS | Get Rotor Status |
| OD | Open Door |
| CD | Close Door |

In the following description, it will be understood that many details of the control program 1130 are within the skill of ordinary process control programmers. For example, the get command step 1133 appropriately stores data accompanying several of the commands, the commands being processed only when completely received, with control being passed from the command step during execution of time-consuming commands for continuous status monitoring by the control program 1130. The get command step 1133 is followed by an execute command step 1134 that initiates execution of the command, and sets appropriate flags and the like. Execution of the Home Motor command is performed in a spindle homing procedure 1135 wherein the spindle head 1006 is advanced to a home index station wherein the load station 1004A is aligned with the access opening 1044, as determined by activation of the index output 1092 of the encoder 1090. The spindle homing procedure 1135 includes an advance step 1136 wherein the spindle head 1006 is advanced at a moderate velocity until the head 1006 passes an index position at which the index output is activated; a reverse step 1137 wherein the spindle head 1006 is stopped, then reversed at a small fraction ($\frac{1}{25}$) of the moderate velocity of the advance step 1136; and an offset step 1138 wherein the spindle head 1006 is again stopped and then advanced beyond the index position by an offset distance. The index position is intentionally angularly displaced from the load station 1004A, for activation of the index output 1092 in the advance step 1133 preferably slightly prior to alignment of the load station 1004A. Thus the offset distance can be made advantageously small for rapid completion of the offset step 1138.

Execution of the Index Move command is performed by an index function 1140, wherein the load stations 1004A, 1004B, 1004C, and 1004D are addressed by corresponding digits 1, 2, 3, and 4, and the spindle head is advanced (algebraicly) by the difference between a presently indexed position and the addressed station, the difference being the number of encoder counts between stations times zero, one, two, or minus one.

Execution of the Begin Run command is performed in a begin run procedure 1142, wherein data of the spin cycle 1002 is used to calculate a destination distance as a sum of an acceleration distance and a constant velocity distance, the acceleration distance being the combination of both acceleration and deceleration distances. More particularly, the constant velocity distance, $D_v$ is the product of the velocity V and time T of the spin cycle 1002, and the acceleration distance is $V^2/A$, where A is a predetermined acceleration, A, V, and T having been previously defined by corresponding ones of the above-identified commands. These distances are summed, then offset by a distance corresponding to the presently indexed position relative to the home position, the result being signalled to the motion board 1094 for activation of the spindle motor 1088. Accordingly, the spindle head 1006 is accelerated at the commanded acceleration to the commanded spin velocity, the spin velocity being maintained for the commanded spin time, the spindle head 1006 being then decelerated at the commanded acceleration to rest at the home position.

Execution of the Home Door command is performed in a home door procedure 1144 having a check home step 1145 and a move home step 1146. The procedure 1144 is exited from the check home step if the first sensor is activated, signifying the door being closed; otherwise, the move home step 1146 is entered for activating the stepper motor driver 1098 to advance the stepper motor 1064 at a slow homing velocity (100 steps/sec.) toward the closed position.

Execution of the Open Door and Close Door commands is performed in a door function 1148, in corresponding opening and closing steps 1149 and 1150. In the closing step 1150, the stepper motor 1064 is caused to be driven 1200 steps toward the closed position at 1500 steps/sec., followed by further movement at 50 steps/sec. until the home (closed) position is sensed. In case door movement is hindered by blockage as described above, damage of the centrifuge unit 1000 and/or injury to laboratory personnel is prevented by the drive wheel 1060 slipping against the edge surface 1068 of the door member 1032' as described above. Similarly, the opening step 1149 operates with opposite activation of the stepper motor 1064, until the second sensor 1082 signals the open position of the door member 1032'.

System Software

A preferred software implementation of the process supervisor 200 and incorporating a graphical user interface (GUI) is based on the Lab-View™ software development package, available from National Instrumentation Corp. of Austin, Tex. In this implementation, maps of the system 10, including the workstation 100 and the centrifuge 1000, for example, are displayed, together with various status indicators and controls. Map displays show the locations of all of the holders 14, and by clicking on a particular holder, its identification is displayed and a map of the containers 12 therein is available. Conversely, the location of a particular container 12 can be searched by entering its identification. This implementation is available as AccelNet software from Beckman Instruments.

Although the present invention has been described in considerable detail with reference to certain preferred versions thereof, other versions are possible. For example, as an alternative to the shield system 40 or in addition thereto, the workstation 100 can be provided with detectors to detect presence of an operator in a portion of the workbench which can be dangerous to the operator, to automatically stop operations, as is typically used in industrial machinery. This can be a device such as light beam and a light beam detector, shutdown of the workstation being triggered by interruption of the light beam. Therefore, the scope of the appended claims should not be limited to the description of the preferred versions contained herein.

What is claimed is:

1. A system for automatically processing multiple containers containing specimens, at least some of the containers having a cap, each of the containers having container identification indicia thereon, the containers being held in a holder, the system comprising:

(a) a central controller comprising (i) memory storage and
  (ii) a data input element for inputting instructions for processing of each container according to the container identification indicia, the processing instructions being stored in memory;

(b) detectors for detecting the presence of a holder in the system, the detectors having an output element for signaling the presence of a holder to the central controller;

(c) an indicia reader for reading the container identification indicia, the reader having an output element for providing the container identification indicia to the central controller;

(d) a container sorting system comprising (i) a data input element in communication with the central controller for receiving instructions from the central controller for sorting containers for selective processing according to the processing instructions stored in the central controller memory storage, and (ii) a plurality of sort sites for placement of containers according to their processing instructions;

(e) a centrifugation system for centrifugation of selected specimens, the centrifugation system comprising:
  (i) receptacles for receiving multiple containers; and
  (ii) a centrifuge for simultaneously centrifuging multiple receptacles, the centrifuge having a motor, a centrifuge controller for stopping the centrifuge at selected positions for automated removal of receptacles from the centrifuge in response to signals from the central controller, a lid with a closed position and an open position, and a lid drive for opening and closing the lid in response to instructions from the central controller;

(f) a receptacle balance system selectively locating individual containers in the receptacles for balancing receptacle weight for the centrifuge;

(g) a decapper system for selectively decapping containers;

(h) at least one analyzer for selectively analyzing the specimens; and (i) a transport system for (i) transporting containers to and from the centrifuge receptacles, the analyzer, and the decapper system, (ii) transporting receptacles to and from the receptacle balance system and the centrifugation system, and (iii) transporting containers in the sorting system, the transport system having a controller in communication with the central controller so that the central controller can control the transport system.

2. The system of claim 1, wherein each container is processed by at least one of the following based on instructions in the central controller:
  (a) sorting only;
  (b) sorting and centrifugation;
  (c) sorting, centrifugation, and decapping;
  (d) sorting, centrifugation, decapping and analysis;
  (e) sorting, decapping and analysis; and
  (f) sorting and analysis.

3. The system of claim 2, further comprising a process supervisor having:
  (a) a programmed detect input step for determining introduction of containers at an input location on the workstation;
  (b) a container select step in which detected containers are selected for processing;
  (c) an identification step for defining process components for each selected container according to the container identification indicia, and
  (d) a process select step for initiating the defined process components being one or more of sorting, centrifugation, decapping, and analysis.

4. The system of claim 1 wherein each analyzer comprises:
  (a) a mechanism for selectively performing at least two different analyses on a specimen;
  (b) an analyzer controller in communication with the central controller so that the central controller can instruct the analyzer as to what analysis to perform for each specimen; and
  (c) an output system for providing analysis results to memory of the central controller.

5. The system of claim 1, comprising two analyzers.

6. The system of claim 5, wherein the output system of each analyzer has an output element for providing analyzer availability information to the central controller, and the central controller has means for selectively determining which analyzer each specimen that is to undergo analysis is analyzed by based on the availability information.

7. The system of claim 1, wherein the specimens are biological specimens.

8. The system of claim 1, wherein the specimens are human blood samples.

9. The system of claim 1, wherein the transport system comprises a first robotic arm for transporting containers to and from the analyzer, and a second robotic arm.

10. The system of claim 9, further comprising a shield system for selectively blocking operator access to the workstation, the shield system including a partition that encloses the top of the workstation and having an opening for passage of the analyzer robotic arm, an enlargement for passage of receptacles to the centrifuge, and an access door being operable in response to instruction from the central controller following operator input.

11. The system of claim 10, wherein the access door is a sash door having an actuator being responsive to the central controller, the shield system further comprising an operator input device for signaling access requests to the central controller, the controller being operative for appropriately inhibiting operation of the workstation robotic arm and then activating the actuator for opening the door.

12. The system of claim 11, wherein the actuator is a pneumatic actuator, the shield system further comprising a lock coupled to the access door, the lock being released in response to instruction from the central controller prior to activation of the actuator.

13. The system of claim 1, wherein the system includes multiple input locations for placement of the containers, each of the input locations having a detector, at least one of the locations being for priority containers, wherein the detector output element signals the presence of priority containers to the central processor, and wherein the central processor provides instructions for priority processing of priority containers.

14. The system of claim 1, wherein the container holders have holder identification indicia thereon, and wherein the indicia reader can read the holder identification indicia, the reader output element providing the holder identification indicia to the central controller for tracking containers according to their respective holders.

15. A system for automatically preparing multiple containers containing specimens, comprising:
  (a) a centrifugation system for centrifugation of selected specimens, the centrifugation system comprising:
    (i) receptacles for receiving multiple containers; and
    (ii) a centrifuge for simultaneously centrifuging multiple receptacles, the centrifuge having a motor, a centrifuge controller for stopping the centrifuge at selected positions for automated removal of receptacles from the centrifuge in response to signals from the central controller, a lid with a closed position and an open position, and a lid drive for opening and closing the lid in response to instructions from the central controller;

(b) a receptacle balance system selectively locating individual containers in the receptacles for balancing receptacle weight for the centrifuge; and (c) a transport system for (i) transporting containers to and from the centrifuge receptacles, and (ii) transporting receptacles to and from the receptacle balance system and the centrifugation system.

16. The system of claim 15, for containers including capped containers and further comprising, a decapper system for selectively decapping containers, wherein the transport system transports centrifuged containers from the centrifugation system to the decapper system.

17. The system of claim 15, wherein the receptacle balance system comprises a balance controller for selectively depositing containers in cavities of centrifuge receptacles, the balance controller being operative for selecting a loading pattern from a set of satisfactory loading patterns in response to a number of containers to be centrifuged in relation to a total container capacity of the centrifuge, and loading the containers into the receptacles in accordance with the selected pattern.

18. The system of claim 15, wherein the receptacle balance system comprises a scale for receiving receptacles to be loaded into the centrifuge, a balance controller for selectively depositing containers in cavities of centrifuge receptacles while correlating incremental weight changes as measured by the scale with the receptacles of each deposit for equalizing weight in pairs of the receptacles.

19. The system of claim 18, wherein the balance controller is additionally operative correlating incremental weight changes as measured by the scale with the locations of each deposit in the receptacles for symmetrically loading weight in each receptacle.

20. The system of claim 18, wherein the receptacle balance system further comprises a plurality of dummy loads, the balance controller being further operative for selectively depositing dummy loads in cavities of centrifuge receptacles while further correlating incremental weight changes as measured by the scale with the locations of each deposit for more accurately equalizing the weight in the pairs of the receptacles.

* * * * *